(12) United States Patent
Steinberg et al.

(10) Patent No.: US 8,781,193 B2
(45) Date of Patent: *Jul. 15, 2014

(54) AUTOMATIC QUANTITATIVE VESSEL ANALYSIS

(75) Inventors: Alexander Steinberg, Ra'anana (IL); Sagiv Philipp, Netanya (IL); David Tolkowsky, Tel Aviv (IL); Ran Cohen, Petah Tikva (IL)

(73) Assignee: Sync-RX, Ltd., Netanya (IL)

( * ) Notice: Subject to any disclaimer, the term of this patent is extended or adjusted under 35 U.S.C. 154(b) by 517 days.

This patent is subject to a terminal disclaimer.

(21) Appl. No.: 12/666,879

(22) PCT Filed: Nov. 18, 2009

(86) PCT No.: PCT/IL2009/001089
§ 371 (c)(1),
(2), (4) Date: Mar. 29, 2012

(87) PCT Pub. No.: WO2010/058398
PCT Pub. Date: May 27, 2010

(65) Prior Publication Data
US 2012/0230565 A1 Sep. 13, 2012

Related U.S. Application Data

(60) Provisional application No. 61/193,329, filed on Nov. 18, 2008, provisional application No. 61/193,915, filed on Jan. 8, 2009, provisional application No. 61/202,181, filed on Feb. 4, 2009, provisional application No. 61/202,451, filed on Mar. 2, 2009, provisional application No. 61/213,216, filed on May 18, 2009, provisional application No. 61/213,534, filed on Jun. 17, 2009, provisional application No. 61/272,210, filed on Sep. 1, 2009, provisional application No. 61/272,356, filed on Sep. 16, 2009.

(51) Int. Cl.
*G06K 9/00* (2006.01)
*A61B 5/02* (2006.01)

(52) U.S. Cl.
USPC ............................ 382/130; 382/199; 600/481

(58) Field of Classification Search
CPC ................ G06K 9/00; A61B 5/02; A61B 6/52
USPC ......... 382/100, 103, 128–134, 155, 162, 168, 382/173, 181, 189–192, 232, 254–258, 382/274–275, 291, 305, 312; 600/424, 513, 600/407, 481; 378/4, 21, 95
See application file for complete search history.

(56) References Cited

U.S. PATENT DOCUMENTS

| | | | |
|---|---|---|---|
| 3,871,360 | A | 3/1975 | Van Horn et al. |
| 3,954,098 | A | 5/1976 | Dick et al. |

(Continued)

FOREIGN PATENT DOCUMENTS

| | | |
|---|---|---|
| EP | 2 570 079 A1 | 3/2013 |
| WO | WO 94/10904 | 5/1994 |

(Continued)

OTHER PUBLICATIONS

Official Action dated Aug. 27, 2012, which issued during the prosecution U.S. Appl. No. 12/075,214.

Official Action dated Oct. 31, 2012, which issued during the prosecution U.S. Appl. No. 12/075,244.

Official Action dated Sep. 20, 2012, which issued during the prosecution of U.S. Appl. No. 12/649,955.

(Continued)

*Primary Examiner* — Seyed Azarian
(74) *Attorney, Agent, or Firm* — Sughrue Mion, PLLC

(57) ABSTRACT

Apparatus and methods are described for use with an image of blood vessels of a subject. In response to a user designating a single point on the image (a) a target portion of a blood vessel is automatically identified in the vicinity of the designated point, and (b) quantitative vessel analysis is performed on the target portion of the blood vessel. An output is generated based upon the quantitative vessel analysis. Other embodiments are also described.

18 Claims, 24 Drawing Sheets

(56) References Cited

U.S. PATENT DOCUMENTS

| | | | |
|---|---|---|---|
| 4,016,871 A | 4/1977 | Schiff | |
| 4,031,884 A | 6/1977 | Henzel | |
| 4,245,647 A | 1/1981 | Randall | |
| 4,270,143 A | 5/1981 | Morris | |
| 4,316,218 A | 2/1982 | Gay | |
| 4,382,184 A | 5/1983 | Wernikoff | |
| 4,545,390 A | 10/1985 | Leary | |
| 4,709,385 A | 11/1987 | Pfeiler | |
| 4,712,560 A | 12/1987 | Schaefer et al. | |
| 4,723,938 A | 2/1988 | Goodin et al. | |
| 4,758,223 A | 7/1988 | Rydell | |
| 4,849,906 A | 7/1989 | Chodos et al. | |
| 4,865,043 A * | 9/1989 | Shimoni | 600/513 |
| 4,878,115 A | 10/1989 | Elion | |
| 4,920,413 A | 4/1990 | Nakamura | |
| 4,991,589 A | 2/1991 | Hongo et al. | |
| 4,994,965 A * | 2/1991 | Crawford et al. | 378/95 |
| 5,020,516 A | 6/1991 | Biondi | |
| 5,054,045 A | 10/1991 | Whiting et al. | |
| 5,054,492 A | 10/1991 | Scribner | |
| 5,056,524 A | 10/1991 | Oe | |
| 5,062,056 A | 10/1991 | Lo et al. | |
| 5,176,619 A | 1/1993 | Segalowitz | |
| 5,177,796 A | 1/1993 | Feig et al. | |
| 5,293,574 A | 3/1994 | Roehm et al. | |
| 5,295,486 A | 3/1994 | Wollschlager et al. | |
| 5,330,496 A | 7/1994 | Alferness | |
| 5,357,550 A | 10/1994 | Asahina et al. | |
| 5,429,144 A | 7/1995 | Wilk | |
| 5,457,728 A | 10/1995 | Whiting et al. | |
| 5,457,754 A | 10/1995 | Han et al. | |
| 5,486,192 A | 1/1996 | Walinsky et al. | |
| 5,537,490 A | 7/1996 | Yukawa | |
| 5,538,494 A | 7/1996 | Matsuda | |
| 5,577,502 A | 11/1996 | Darrow et al. | |
| 5,586,201 A | 12/1996 | Whiting et al. | |
| 5,596,990 A | 1/1997 | Yock | |
| 5,613,492 A | 3/1997 | Feinberg | |
| 5,619,995 A | 4/1997 | Lobodzinski | |
| 5,630,414 A | 5/1997 | Horbaschek | |
| 5,674,217 A | 10/1997 | Walhstrom et al. | |
| 5,724,977 A | 3/1998 | Yock | |
| 5,764,723 A | 6/1998 | Weinberger | |
| 5,766,208 A | 6/1998 | McEwan | |
| 5,792,157 A | 8/1998 | Mische et al. | |
| 5,809,105 A | 9/1998 | Roehm et al. | |
| 5,822,391 A | 10/1998 | Whiting et al. | |
| 5,830,222 A | 11/1998 | Makower | |
| 5,879,305 A | 3/1999 | Yock | |
| 5,885,218 A | 3/1999 | Teo | |
| 5,885,244 A | 3/1999 | Leone et al. | |
| 5,916,194 A | 6/1999 | Jacobsen et al. | |
| 5,921,934 A | 7/1999 | Teo | |
| 5,971,976 A | 10/1999 | Wang et al. | |
| 6,088,488 A | 7/2000 | Hardy et al. | |
| 6,095,976 A | 8/2000 | Nachtomy | |
| 6,120,455 A | 9/2000 | Teo | |
| 6,126,608 A | 10/2000 | Kemme et al. | |
| 6,148,095 A | 11/2000 | Prause et al. | |
| 6,152,878 A | 11/2000 | Nachtomy | |
| 6,195,445 B1 | 2/2001 | Dubuisson-Jolly et al. | |
| 6,233,478 B1 | 5/2001 | Liu | |
| 6,246,898 B1 | 6/2001 | Vesely et al. | |
| 6,254,541 B1 | 7/2001 | Teo | |
| 6,267,727 B1 | 7/2001 | Teo | |
| 6,278,767 B1 | 8/2001 | Hsieh | |
| 6,331,181 B1 | 12/2001 | Tierney et al. | |
| 6,370,417 B1 | 4/2002 | Horbaschek et al. | |
| 6,377,011 B1 | 4/2002 | Ben-Ur | |
| 6,442,415 B1 | 8/2002 | Bis et al. | |
| 6,454,715 B2 | 9/2002 | Teo | |
| 6,454,776 B1 | 9/2002 | Tajima et al. | |
| 6,473,635 B1 | 10/2002 | Rasche | |
| 6,491,636 B2 | 12/2002 | Chenal | |
| 6,496,716 B1 | 12/2002 | Langer et al. | |
| 6,532,380 B1 | 3/2003 | Close et al. | |
| 6,538,634 B1 | 3/2003 | Chui et al. | |
| 6,546,271 B1 | 4/2003 | Reisfeld | |
| 6,576,007 B2 | 6/2003 | Dehdashtian et al. | |
| 6,589,176 B2 | 7/2003 | Jago | |
| 6,616,596 B1 | 9/2003 | Milbocker | |
| 6,643,533 B2 | 11/2003 | Knoplioch | |
| 6,659,953 B1 | 12/2003 | Sumanaweera et al. | |
| 6,666,863 B2 | 12/2003 | Wentzel et al. | |
| 6,704,593 B2 | 3/2004 | Stainsby | |
| 6,708,052 B1 | 3/2004 | Mao et al. | |
| 6,711,436 B1 | 3/2004 | Duhaylongsod | |
| 6,718,055 B1 | 4/2004 | Suri | |
| 6,726,675 B1 | 4/2004 | Beyar | |
| 6,728,566 B1 | 4/2004 | Subramanyan | |
| 6,731,973 B2 | 5/2004 | Voith | |
| 6,786,896 B1 | 9/2004 | Madhani et al. | |
| 6,788,827 B1 | 9/2004 | Makram-Ebeid | |
| 6,796,972 B1 | 9/2004 | Sinofsky et al. | |
| 6,835,177 B2 | 12/2004 | Fritz et al. | |
| 6,858,003 B2 | 2/2005 | Evans et al. | |
| 6,912,471 B2 | 6/2005 | Heigl | |
| 6,937,696 B1 | 8/2005 | Mostafavi | |
| 6,959,266 B1 | 10/2005 | Mostafavi | |
| 6,973,202 B2 | 12/2005 | Mostafavi | |
| 6,980,675 B2 | 12/2005 | Evron et al. | |
| 6,996,430 B1 | 2/2006 | Gilboa et al. | |
| 6,999,852 B2 | 2/2006 | Green | |
| 7,031,504 B1 | 4/2006 | Argiro et al. | |
| 7,070,555 B2 | 7/2006 | Siess | |
| 7,085,342 B2 | 8/2006 | Younis et al. | |
| 7,134,994 B2 | 11/2006 | Alpert | |
| 7,155,046 B2 | 12/2006 | Aben et al. | |
| 7,155,315 B2 | 12/2006 | Niemeyer et al. | |
| 7,180,976 B2 | 2/2007 | Wink et al. | |
| 7,191,100 B2 | 3/2007 | Mostafavi | |
| 7,209,779 B2 | 4/2007 | Kaufman | |
| 7,215,802 B2 | 5/2007 | Klingensmith | |
| 7,269,457 B2 | 9/2007 | Shafer | |
| 7,289,652 B2 * | 10/2007 | Florent et al. | 382/130 |
| 7,321,677 B2 | 1/2008 | Evron et al. | |
| 7,339,585 B2 | 3/2008 | Verstraelen et al. | |
| 7,343,032 B2 | 3/2008 | Oakley et al. | |
| 7,343,195 B2 | 3/2008 | Strommer et al. | |
| 7,359,554 B2 | 4/2008 | Klingensmith | |
| 7,369,691 B2 | 5/2008 | Kondo et al. | |
| 7,397,935 B2 | 7/2008 | Kimmel | |
| 7,517,318 B2 | 4/2009 | Altmann | |
| 7,546,154 B2 | 6/2009 | Hornegger et al. | |
| 7,587,074 B2 | 9/2009 | Zarkh et al. | |
| 7,599,730 B2 | 10/2009 | Hunter | |
| 7,604,601 B2 | 10/2009 | Altmann | |
| 7,668,362 B2 * | 2/2010 | Olson et al. | 382/133 |
| 7,693,349 B2 | 4/2010 | Gering | |
| 7,697,974 B2 | 4/2010 | Jenkins | |
| 7,713,210 B2 | 5/2010 | Byrd | |
| 7,729,743 B2 | 6/2010 | Sabczynski et al. | |
| 7,729,746 B2 | 6/2010 | Redel et al. | |
| 7,740,584 B2 | 6/2010 | Donaldson | |
| 7,773,787 B2 | 8/2010 | Tek et al. | |
| 7,773,792 B2 | 8/2010 | Kimmel | |
| 7,778,488 B2 | 8/2010 | Nord | |
| 7,778,688 B2 | 8/2010 | Strommer | |
| 7,822,291 B2 | 10/2010 | Guetter | |
| 7,831,076 B2 | 11/2010 | Altmann | |
| 7,848,553 B2 | 12/2010 | Hertel | |
| 7,877,132 B2 | 1/2011 | Rongen | |
| 7,916,912 B2 | 3/2011 | Abramov et al. | |
| 7,925,064 B2 | 4/2011 | Cloutier et al. | |
| 7,925,069 B2 * | 4/2011 | Ortyn et al. | 382/133 |
| 7,927,275 B2 | 4/2011 | Kuban | |
| 7,930,014 B2 * | 4/2011 | Huennekens et al. | 600/407 |
| 7,935,055 B2 | 5/2011 | Burckhardt | |
| 7,961,926 B2 | 6/2011 | Viswanathan | |
| 7,965,905 B2 | 6/2011 | Allon et al. | |
| 7,970,187 B2 | 6/2011 | Puts | |
| 7,978,916 B2 | 7/2011 | Klingensmith | |
| 7,992,100 B2 | 8/2011 | Lundstrom | |
| 8,029,447 B2 | 10/2011 | Kanz | |

(56) References Cited

U.S. PATENT DOCUMENTS

| | | | |
|---|---|---|---|
| 8,050,474 B2 | 11/2011 | Baumgart | |
| 8,052,605 B2 | 11/2011 | Muller | |
| 8,055,327 B2 | 11/2011 | Strommer et al. | |
| 8,077,939 B2 | 12/2011 | Le Nezet et al. | |
| 8,086,000 B2 | 12/2011 | Weijers | |
| 8,155,411 B2 | 4/2012 | Hof | |
| 8,157,742 B2 | 4/2012 | Taylor | |
| 8,165,361 B2 | 4/2012 | Li | |
| 8,172,763 B2 | 5/2012 | Nelson | |
| 8,189,886 B2 | 5/2012 | Huo et al. | |
| 8,199,981 B2 | 6/2012 | Koptenko et al. | |
| 8,200,040 B2 | 6/2012 | Pfister | |
| 8,213,676 B2 | 7/2012 | Bendall | |
| 8,233,718 B2 | 7/2012 | Klingensmith | |
| 8,271,068 B2 | 9/2012 | Khamene | |
| 8,275,201 B2 | 9/2012 | Rangawala et al. | |
| 8,289,284 B2 | 10/2012 | Glynn | |
| 8,298,147 B2 | 10/2012 | Huennekens | |
| 8,303,503 B2 | 11/2012 | Nair | |
| 8,364,242 B2 | 1/2013 | Li | |
| 8,396,276 B2 | 3/2013 | Gatta | |
| 8,409,098 B2 | 4/2013 | Olson | |
| 8,428,318 B2 | 4/2013 | Zhuo | |
| 8,428,691 B2 | 4/2013 | Byrd | |
| 8,433,115 B2 | 4/2013 | Chen | |
| 8,457,374 B2 | 6/2013 | Lendl | |
| 8,478,387 B2 | 7/2013 | Xu | |
| 8,483,488 B2 | 7/2013 | Richter | |
| 8,565,859 B2 | 10/2013 | Wang et al. | |
| 2001/0031919 A1 | 10/2001 | Strommer et al. | |
| 2002/0049375 A1 | 4/2002 | Strommer et al. | |
| 2002/0058869 A1 | 5/2002 | Axelsson et al. | |
| 2002/0090119 A1 | 7/2002 | Saito et al. | |
| 2002/0114497 A1* | 8/2002 | Wetzel et al. | 382/128 |
| 2002/0188307 A1 | 12/2002 | Pintor et al. | |
| 2003/0014100 A1 | 1/2003 | Maria Meens et al. | |
| 2003/0018251 A1 | 1/2003 | Solomon | |
| 2003/0023141 A1 | 1/2003 | Stelzer et al. | |
| 2003/0069499 A1 | 4/2003 | Lienard et al. | |
| 2003/0088179 A1 | 5/2003 | Seeley et al. | |
| 2003/0139772 A1 | 7/2003 | Fisher et al. | |
| 2003/0157073 A1 | 8/2003 | Perrit et al. | |
| 2004/0034380 A1 | 2/2004 | Woolfson et al. | |
| 2004/0077941 A1 | 4/2004 | Reddy et al. | |
| 2004/0097805 A1 | 5/2004 | Verard et al. | |
| 2004/0176681 A1 | 9/2004 | Mao et al. | |
| 2004/0249270 A1 | 12/2004 | Kondo et al. | |
| 2004/0254570 A1 | 12/2004 | Hadjicostis et al. | |
| 2004/0267113 A1 | 12/2004 | Thomson | |
| 2005/0004503 A1 | 1/2005 | Samson et al. | |
| 2005/0008210 A1 | 1/2005 | Evron et al. | |
| 2005/0031176 A1 | 2/2005 | Hertel | |
| 2005/0033199 A1 | 2/2005 | van der Steen | |
| 2005/0043614 A1 | 2/2005 | Huizenga et al. | |
| 2005/0054916 A1 | 3/2005 | Mostafavi | |
| 2005/0080336 A1 | 4/2005 | Byrd et al. | |
| 2005/0090737 A1 | 4/2005 | Burrel et al. | |
| 2005/0096589 A1 | 5/2005 | Shachar | |
| 2005/0107688 A1 | 5/2005 | Strommer | |
| 2005/0107808 A1 | 5/2005 | Evans et al. | |
| 2005/0111719 A1 | 5/2005 | Pescatore et al. | |
| 2005/0137661 A1 | 6/2005 | Sra | |
| 2005/0143777 A1 | 6/2005 | Sra | |
| 2005/0154281 A1 | 7/2005 | Xue et al. | |
| 2005/0197557 A1 | 9/2005 | Strommer et al. | |
| 2005/0197559 A1 | 9/2005 | Boese et al. | |
| 2005/0197566 A1 | 9/2005 | Strommer et al. | |
| 2005/0201510 A1 | 9/2005 | Mostafavi | |
| 2005/0228359 A1 | 10/2005 | Doyle | |
| 2005/0234331 A1 | 10/2005 | Sendai | |
| 2005/0273050 A1 | 12/2005 | Yokoyama et al. | |
| 2005/0288577 A1 | 12/2005 | Weese | |
| 2006/0058647 A1 | 3/2006 | Strommer et al. | |
| 2006/0074285 A1 | 4/2006 | Zarkh et al. | |
| 2006/0106318 A1 | 5/2006 | Davidson | |
| 2006/0120581 A1 | 6/2006 | Eck et al. | |
| 2006/0129142 A1 | 6/2006 | Reynolds | |
| 2006/0147897 A1 | 7/2006 | Grinvald | |
| 2006/0149134 A1 | 7/2006 | Soper et al. | |
| 2006/0165270 A1 | 7/2006 | Borgert et al. | |
| 2006/0173287 A1 | 8/2006 | Sabszynski et al. | |
| 2006/0184016 A1 | 8/2006 | Glossop | |
| 2006/0193505 A1 | 8/2006 | Glukhovsky et al. | |
| 2006/0224188 A1 | 10/2006 | Libbus et al. | |
| 2006/0241445 A1 | 10/2006 | Altmann | |
| 2006/0241465 A1 | 10/2006 | Huennekens et al. | |
| 2006/0241478 A1 | 10/2006 | Lewis | |
| 2006/0253024 A1 | 11/2006 | Altmann | |
| 2006/0253029 A1 | 11/2006 | Altmann | |
| 2006/0253031 A1 | 11/2006 | Altmann | |
| 2006/0257006 A1 | 11/2006 | Bredno et al. | |
| 2006/0259137 A1 | 11/2006 | Artof et al. | |
| 2006/0269108 A1 | 11/2006 | Viswanathan | |
| 2006/0287595 A1 | 12/2006 | Maschke | |
| 2007/0038061 A1 | 2/2007 | Huennekens et al. | |
| 2007/0038081 A1 | 2/2007 | Eck et al. | |
| 2007/0043292 A1 | 2/2007 | Camus | |
| 2007/0053558 A1 | 3/2007 | Puts et al. | |
| 2007/0055128 A1 | 3/2007 | Glossop | |
| 2007/0060798 A1 | 3/2007 | Krupnik et al. | |
| 2007/0088431 A1 | 4/2007 | Bourang et al. | |
| 2007/0106146 A1 | 5/2007 | Altmann et al. | |
| 2007/0116342 A1 | 5/2007 | Zarkh et al. | |
| 2007/0123771 A1 | 5/2007 | Redel et al. | |
| 2007/0142907 A1 | 6/2007 | Moaddeb et al. | |
| 2007/0173861 A1 | 7/2007 | Strommer | |
| 2007/0208388 A1 | 9/2007 | Jahns | |
| 2007/0219630 A1 | 9/2007 | Chu | |
| 2007/0232896 A1 | 10/2007 | Gilboa et al. | |
| 2007/0248253 A1 | 10/2007 | Manzke et al. | |
| 2007/0255139 A1 | 11/2007 | Deschinger | |
| 2007/0276216 A1 | 11/2007 | Beyar et al. | |
| 2008/0008366 A1 | 1/2008 | Desh | |
| 2008/0015677 A1 | 1/2008 | Glossop et al. | |
| 2008/0021331 A1 | 1/2008 | Grinvald | |
| 2008/0082049 A1 | 4/2008 | Evans et al. | |
| 2008/0089566 A1 | 4/2008 | Node-Langlois | |
| 2008/0119922 A1 | 5/2008 | Alkhatib | |
| 2008/0137935 A1 | 6/2008 | Spahn | |
| 2008/0146923 A1 | 6/2008 | Mejia | |
| 2008/0146942 A1 | 6/2008 | Dala-Krishna | |
| 2008/0177183 A1 | 7/2008 | Courtney | |
| 2008/0188739 A1 | 8/2008 | Rongen et al. | |
| 2008/0221439 A1 | 9/2008 | Iddan et al. | |
| 2008/0221440 A1* | 9/2008 | Iddan et al. | 600/424 |
| 2008/0221442 A1 | 9/2008 | Tolkowsky et al. | |
| 2008/0253686 A1 | 10/2008 | Bayer | |
| 2008/0267475 A1* | 10/2008 | Lendl | 382/130 |
| 2008/0300487 A1 | 12/2008 | Govari | |
| 2009/0016587 A1 | 1/2009 | Strobel et al. | |
| 2009/0074284 A1* | 3/2009 | Zeineh et al. | 382/133 |
| 2009/0093676 A1 | 4/2009 | Davidson | |
| 2009/0103682 A1 | 4/2009 | Chen et al. | |
| 2009/0105579 A1 | 4/2009 | Garibaldi | |
| 2009/0114238 A1 | 5/2009 | Hornbach et al. | |
| 2009/0171201 A1 | 7/2009 | Olson | |
| 2009/0177444 A1 | 7/2009 | Wiemker et al. | |
| 2009/0257631 A1 | 10/2009 | Baumgart | |
| 2009/0264753 A1 | 10/2009 | Von Schulthes | |
| 2009/0275831 A1 | 11/2009 | Hall | |
| 2009/0281418 A1 | 11/2009 | Ruijters et al. | |
| 2009/0299195 A1 | 12/2009 | Muller et al. | |
| 2009/0306547 A1 | 12/2009 | Iddan et al. | |
| 2010/0041949 A1 | 2/2010 | Tolkowsky | |
| 2010/0049034 A1 | 2/2010 | Eck et al. | |
| 2010/0054573 A1 | 3/2010 | Shekhara | |
| 2010/0067768 A1 | 3/2010 | Ionasec et al. | |
| 2010/0094124 A1 | 4/2010 | Schoonenberg et al. | |
| 2010/0094127 A1 | 4/2010 | Xu | |
| 2010/0099979 A1 | 4/2010 | Schoonenberg et al. | |
| 2010/0111396 A1* | 5/2010 | Boucheron | 382/133 |
| 2010/0114289 A1 | 5/2010 | Camus | |
| 2010/0123715 A1 | 5/2010 | Hansegard | |
| 2010/0134517 A1 | 6/2010 | Saikaly et al. | |

(56) References Cited

U.S. PATENT DOCUMENTS

| | | |
|---|---|---|
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |
| 2010/0191102 A1 | 7/2010 | Steinberg et al. |
| 2010/0198063 A1 | 8/2010 | Huber |
| 2010/0220917 A1 | 9/2010 | Steinberg et al. |
| 2010/0222671 A1 | 9/2010 | Cohen et al. |
| 2010/0228076 A1 | 9/2010 | Blank et al. |
| 2010/0246910 A1 | 9/2010 | Wiemker |
| 2010/0290693 A1 | 11/2010 | Cohen et al. |
| 2010/0310140 A1 | 12/2010 | Schneider |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmitt et al. |
| 2011/0075912 A1 | 3/2011 | Rieber et al. |
| 2011/0087104 A1 | 4/2011 | Moore |
| 2011/0118825 A1 | 5/2011 | Hunter et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1 | 1/2012 | Tolkowsky et al. |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0072190 A1 | 3/2012 | Sharma et al. |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0245460 A1 | 9/2012 | Slomka |
| 2013/0004044 A1 | 1/2013 | Ross |
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0120296 A1 | 5/2013 | Merrit |
| 2013/0120297 A1 | 5/2013 | Merrit |
| 2013/0123616 A1 | 5/2013 | Merrit |
| 2013/0329030 A1 | 12/2013 | Tolkowsky et al. |
| 2013/0329977 A1 | 12/2013 | Tolkowsky et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Klaiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |

FOREIGN PATENT DOCUMENTS

| | | |
|---|---|---|
| WO | 99/07354 A2 | 2/1999 |
| WO | 00/33755 A1 | 6/2000 |
| WO | 01/10313 A1 | 2/2001 |
| WO | WO 01/43642 | 6/2001 |
| WO | 03/043516 A2 | 5/2003 |
| WO | WO 03/096894 | 11/2003 |
| WO | WO 2005/026891 | 3/2005 |
| WO | 2005051452 A2 | 6/2005 |
| WO | WO 2005/124689 | 12/2005 |
| WO | 2006/027781 A2 | 3/2006 |
| WO | WO 2006/066122 | 6/2006 |
| WO | WO 2006/066124 | 6/2006 |
| WO | 2006/076409 A2 | 7/2006 |
| WO | 2006/114721 A2 | 11/2006 |
| WO | WO 2006/121984 | 11/2006 |
| WO | 2007/002685 A2 | 1/2007 |
| WO | 2007/014028 A1 | 2/2007 |
| WO | 2007/015199 A2 | 2/2007 |
| WO | 2008/007350 A1 | 1/2008 |
| WO | WO 2008/007350 | 1/2008 |
| WO | WO 2008/107905 | 9/2008 |
| WO | WO 2009/153794 | 12/2009 |
| WO | 2010/058398 A2 | 5/2010 |
| WO | WO 2010/058398 | 5/2010 |
| WO | 2011/046903 A2 | 4/2011 |
| WO | 2011/046904 A1 | 4/2011 |
| WO | 2011/145094 A2 | 11/2011 |
| WO | 2012/014212 A2 | 2/2012 |
| WO | 2012/028190 A1 | 3/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013/084345 A1 | 6/2013 |
| WO | 2013/169814 A1 | 11/2013 |
| WO | 2013/175472 A2 | 11/2013 |
| WO | 2014/002095 A2 | 1/2014 |

OTHER PUBLICATIONS

International Search Report dated Oct. 10, 2012, which issued during the prosecution of PCT/IL2012/000246.

Communication dated Sep. 5, 2012, which issued during the prosecution of EP Application 09 766329.8-1526.

Communication dated Oct. 29, 2012, which issued during the prosecution of EP Application 08 719941.0-1265/2129284.

Official Action dated Oct. 23, 2012, which issued during the prosecution of JP Application No. 2009-552328.

Computer translation of JP 2010-253017 to Takeshi.

W. Goodman et al., "Coronary-Artery Calcification in Young Adults With End-Stage Renal Disease Who Are Undergoing Dialysis," The New England Journal of Medicine, vol. 342 No. 20.

W. Santamore et al., "A microcomputer based automated quantative coronary angiographic analysis system," Annals of Biomedical Engineering, vol. 16, pp. 367-377, 1988.

I. Kompatsiaris et al., "Deformable Boundary Detection of Stents in Angiographic Images," IEEE Transactions on Medical Imaging, vol. 19, No. 6, Jun. 2000.

V. Duddalwar, "Multislice CT angiography: a practical guide to CT angiography in vascular imaging and intervention," The British Journal of Radiology, 77 (2004), S27-S38.

W. Leung et al., "Coronary Artery Quantitation and Data Management System for Paired Cineangiograms," Catheterization and Cardiovascular Diagnosis 24:121-134 (1991).

G. Mancini et al., "Automated quantitative coronary arteriography: morphologic and physiologic validation in vivo of a rapid digital angiographic method," Circulation 1987;75:452-460.

L. Yaneza et al., "Atherosclerotic Plaque Can Be Quantified Using Multifractal and Wavelet Decomposition Techniques," Abstracts—Angiography & Interventional Cardiology, JACC Mar. 3, 2004.

(56) References Cited

OTHER PUBLICATIONS

Official Action dated Nov. 23, 2012, which issued during the prosecution of U.S. Appl. No. 12/649,944.
U.S. Appl. No. 61/359,431.
A Notice of Allowance issued in Applicant's U.S. Appl. No. 13/965,893.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 25, 2013, which issued during the prosecution of Applicant's U.S. Appl. No. 12/781,366.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL2013/50549.
Correspondence from the International Searching Authority in Applicant's PCT/IL2013/050438.
A search report dated Nov. 23, 2012, which issued during the prosecution of Applicant's EP Application 09827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
Umeda, H. et al., "Promising efficacy of primary gradual and prolonged balloon angioplasty in small coronary arteries: A randomized comparison with cutting balloon angioplasty and conventional balloon angioplasty", American Heart Journal, vol. 147, No. 1 pp. 1-8, Jan. 2004.
Office Action dated May 22, 2012, issued in U.S. Appl. No. 12/075,244.
Office Action dated Mar. 15, 2012, issued in U.S. Appl. No. 12/650,152.
Office Action dated Mar. 15, 2012, issued in U.S. Appl. No. 12/649,944.
Office Action dated Mar. 14, 2012, issued in U.S. Appl. No. 12/075,214.
International Search Report dated Mar. 2, 2012, issued in PCT/IL11/00612.
An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
An Official Action dated May 6, 2013, which issued during the prosecution of Applicant's U.S. Appl. No. 12/487,315.
A Notice of Allowance dated Jun. 4, 2013, which issued in Applicant's U.S. Appl. No. 12/649,960.
Boyle et al., entitled "Assessment of a Novel Angiographic Image Stabilization System for Percutaneous Coronary Intervention" (Journal of Interventional Cardiology, vol. 20 No. 2, 2007.
Timinger et al., entitled "Motion compensated coronary interventional navigation by means of diaphragm tracking and elastic motion models" (Phys Med Biol. Feb. 7, 2005;50(3):491-503.
Timinger et al., entitled "Motion compensation for interventional navigation on 3D static roadmaps based on an affine model and gating" (Phys Med Biol. Mar. 7, 2004;49(5):719-32.
Turski et al., entitled "Digital Subtraction Angiography 'Road Map'" (American Journal of Roentgenology, 1982.
Iddan et al., entitled "3D imaging in the studio and elsewhere" (SPIE Proceedings vol. 4298, 2001.
"Catheter Insertion Simulation with Combined Visual and Haptic Feedback," by Zorcolo et al. (Center for Advanced Studies, Research and Development in Sardinia).
"4D-CT imaging of a volume influenced by respiratory motion on multi-slice CT Tinsu Pan," by Lee et al., (Medical Physics, Feb. 2004, vol. 31, Issue 2, pp. 333-340)—an abstract.
"New 4-D imaging for real-time intraoperative MRI: adaptive 4-D scan," by Tokuda et al. (Med Image Comput Assist Intery Int Conf. 2006;9(Pt 1):454-61) an abstract.
"Real-time interactive viewing of 4D kinematic MR joint studies," by Schulz et al. (Med Image Comput Assist Interv Int Conf. 2005;8(Pt 1):467-73.)—an abstract.
"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).
"Prospective motion correction of X-ray images for coronary interventions," by Shechter et al. (IEEE Trans Med Imaging. Apr. 2005;24(4):441-50).
"Cardiac Imaging: We Got the Beat!" by Elizabeth Morgan (Medical Imaging, Mar. 2005).
"Noninvasive Coronary Angiography by Retrospectively ECG-Gated Multislice Spiral CT," by Achenbach et al., (Circulation. Dec. 5, 2000;102(23):2823-8).
"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.
"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Soffie Mansson, et al., "Dosimetric verification of breathing adapted radiotherapy using polymer gel", Journal of Physics: Conference series 56 (200) 300-303.
"From 2D to 4D" AXIOM Innovations—Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik 1, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.
Brochure: At the TCT conference held in San Francisco, USA in Sep. 2009, Paieon Inc. demonstrated the IC-PRO Comprehensive Imaging Workstation for providing assistance in cardiac catheterization procedures.
An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.

(56) References Cited

OTHER PUBLICATIONS

An International Search Report dated May 19, 2010 issued during the prosecution of Applicant's PCT Patent Application No. PCT/IL2009/001089.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).
"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
U.S. Appl. No. 61/193,329, filed Nov. 18, 2008.
U.S. Appl. No. 61/193,915, filed Jan. 8, 2009.
U.S. Appl. No. 61/202,181, filed Feb. 4, 2009.
U.S. Appl. No. 61/202,451, filed Mar. 2, 2009.
U.S. Appl. No. 61/213,216, filed May 18, 2009.
U.S. Appl. No. 61/213,534, filed Jun. 17, 2009.
U.S. Appl. No. 61/272,210, filed Sep. 1, 2009.
U.S. Appl. No. 61/272,356, filed Sep. 16, 2009.
U.S. Appl. No. 12/487,315, filed Jun. 18, 2009.
U.S. Appl. No. 60/996,746, filed Dec. 4, 2007.
U.S. Appl. No. 60/935,914, filed Sep. 6, 2007.
U.S. Appl. No. 60/929,165, filed Jun. 15, 2007.
U.S. Appl. No. 60/924,609, filed May 22, 2007.
U.S. Appl. No. 60/906,091, filed Mar. 8, 2007.
U.S. Appl. No. 12/075,214, filed Mar. 10, 2008.
U.S. Appl. No. 12/075,252, filed Mar. 10, 2008.
U.S. Appl. No. 61/129,331, filed Jun. 19, 2008.
U.S. Appl. No. 12/075,244, filed Mar. 10, 2008.
"Geometrically Correct 3-D Reconstruction of Intravascular Ultrasound Images by Fusion with Biplane Angiography—Methods and Validation," Andreas Wahle, IEEE Transactions on Medical Imaging, Final Manuscript #187/98, Jun. 30, 1999.
An International Search Report dated Jan. 6, 2012, which issued during the prosecution of Applicant's PCT Application No. PCT/IL11/00391.
An Official Action dated Nov. 28, 2011, which issued during the prosecution of Applicant's U.S. Appl. No. 12/075,252.
An Official Action dated Dec. 8, 2011, which issued during the prosecution of Applicant's U.S. Appl. No. 12/075,244.
U.S. Appl. No. 60/845,347 to Strommer et al., filed Sep. 2006.
An Official Action dated Sep. 6, 2013, which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave-Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
Office Action dated Jan. 7, 2014, issued by the U.S. Patent and Trademark Office in corresponding U.S. Appl. No. 12/075,244.
Office Action dated Dec. 31, 2013, issued by the U.S. Patent and Trademark Office in corresponding U.S. Appl. No. 12/075,252.
Office Action dated Feb. 12, 2014, issued by the U.S. Patent and Trademark Office in corresponding U.S. Appl. No. 12/781,260.
Notice of Allowance dated Jan. 3, 2014, issued by the U.S. Patent and Trademark Office in corresponding U.S. Appl. No. 13/965,872.
International Search Report (PCT/ISA/220, PCT/ISA/210, & PCT/ISA/237) dated Dec. 2, 2013, issued by the International Searching Authority in corresponding Application No. PCT/IL2013/050438.
International Search Report (PCT/ISA/220, PCT/ISA/210, & PCT/ISA/237) dated Jan. 22, 2014, issued by the International Searching Authority in corresponding Application No. PCT/IL13/50549.
Office Action, dated Mar. 21, 2014, issued by the United States Patent and Trademark Office, in counterpart U.S. Appl. No. 12/648,913.
Office Action, dated Apr. 3, 2014, issued by the United States Patent and Trademark Office, in counterpart U.S. Appl. No. 12/649,955.
Office Action, dated May 6, 2014, issued by the United States Patent and Trademark Office, in counterpart U.S. Appl. No. 12/075,252.
Office Action, dated Mar. 14, 2014, issued by the United States Patent and Trademark Office, in counterpart U.S. Appl. No. 12/650,605.
Office Action, dated Apr. 25, 2014, issued by the United States Patent and Trademark Office, in counterpart U.S. Appl. No. 12/650,121.
Office Action, dated Feb. 20, 2014, issued by the United States Patent and Trademark Office, in counterpart U.S. Appl. No. 12/075,214.
Office Action, dated Apr. 24, 2014, issued by the United States Patent and Trademark Office, in counterpart U.S. Appl. No. 12/781,366.
Office Action, dated Apr. 28, 2014, issued by the United States Patent and Trademark Office, in counterpart U.S. Appl. No. 13/228,185.
Office Action, dated Apr. 17, 2014, issued by the United States Patent and Trademark Office, in counterpart U.S. Appl. No. 13/228,211.
Office Action, dated May 5, 2014, issued by the United States Patent and Trademark Office, in counterpart U.S. Appl. No. 14/096,968.
Office Action, dated Feb. 14, 2014, issued by the United States Patent and Trademark Office, in counterpart U.S. Appl. No. 14/098,140.
Tu, et al., "Fusion of 3D QCA and IVUS/OCT", Int. J Cardiovasc Imaging (2011), 27: p. 197-207, DOI 10.1007/s10554-011-9809-2.
Tu, et al., "In vivo comparison of arterial lumen dimensions assessed by co-registered three dimensional (3D) quantitative coronary angiography, intravascular ultrasound and optical coherence

(56) References Cited

OTHER PUBLICATIONS tomography", Int. J Cardiovasc Imaging (2012) 28: p. 1315-1327, DOI 10.1007/s10554-012-0016-6.

Pyxaras, et al., "Quantitative Angiography and Optical Coherence Tomography for the Functional Assessment of Nonobstructive Coronary Stenoses", Comparison With Fractional Flow Reserve, Am Heart J. 2013; 166(6): p. 1010-1018, Medscape Oct. 2013.

* cited by examiner

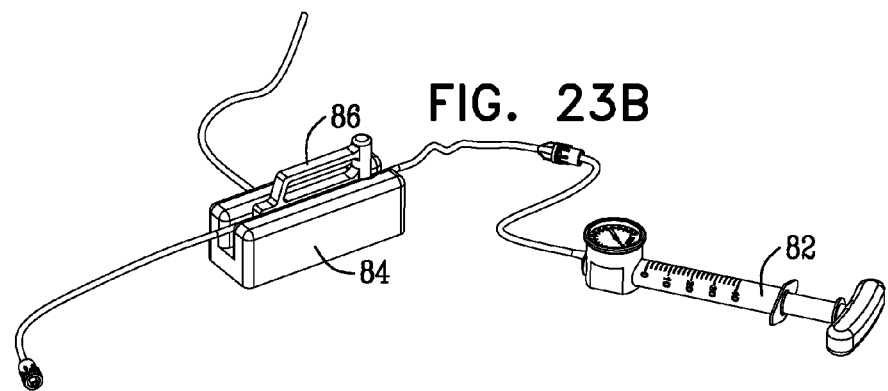
FIG. 23B
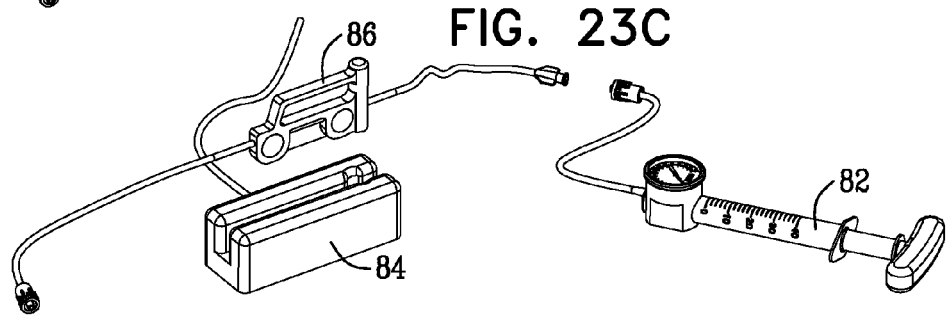
FIG. 23C
FIG. 24
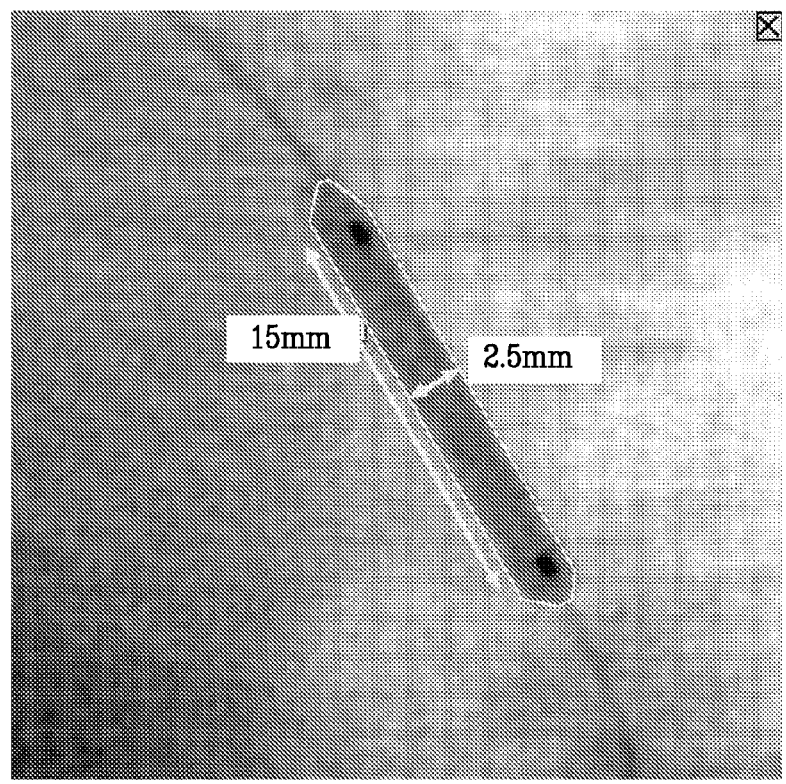

ved as US 2009/0306547), filed Jun. 18, 2009, entitled

AUTOMATIC QUANTITATIVE VESSEL ANALYSIS

CROSS REFERENCES TO RELATED APPLICATIONS

The present application is a U.S. national phase of PCT Application no. PCT/IL2009/001089 to Cohen et al. (published as WO 10/058398), filed Nov. 18, 2009, which claims priority from the following patent applications, all of which are incorporated herein by reference:

U.S. Provisional Patent Application 61/193,329, entitled "Apparatuses and methods for the automatic generation of a road map from angiographic images of a cyclically-moving organ," to Steinberg et al., filed Nov. 18, 2008.

U.S. Provisional Patent Application 61/193,915, entitled "Image processing and tool actuation for medical procedures," to Steinberg et al., filed Jan. 8, 2009.

U.S. Provisional Patent Application 61/202,181, entitled "Image processing and tool actuation for medical procedures," to Steinberg et al., filed Feb. 4, 2009.

U.S. Provisional Patent Application 61/202,451, entitled "Image processing and tool actuation for medical procedures," to Steinberg et al., filed Mar. 2, 2009.

U.S. Provisional Patent Application 61/213,216, entitled "Image processing and tool actuation for medical procedures," to Steinberg et al., filed May 18, 2009.

U.S. Provisional Patent Application 61/213,534, entitled "Image Processing and Tool Actuation for Medical Procedures," to Steinberg et al., filed Jun. 17, 2009.

U.S. Provisional Patent Application 61/272,210, entitled "Image processing and tool actuation for medical procedures," to Steinberg et al., filed Sep. 1, 2009.

U.S. Provisional Patent Application 61/272,356, entitled "Image Processing and Tool Actuation for Medical Procedures" to Steinberg et al., filed Sep. 16, 2009.

The present application is related to the following patent applications, all of which are incorporated herein by reference:

PCT Application PCT/IL2008/000316 to Iddan (published as WO 08/107905), filed on Mar. 9, 2008, entitled "Imaging and tools for use with moving organs"

U.S. patent application Ser. No. 12/075,244 to Tolkowsky (published as US 2008/0221442), filed Mar. 10, 2008, entitled "Imaging for use with moving organs"

U.S. patent application Ser. No. 12/075,214 to Iddan (published as 2008/0221439), filed Mar. 10, 2008, entitled "Tools for use with moving organs" and U.S. patent application Ser. No. 12/075,252 to Iddan (published as US 2008/0221440), filed Mar. 10, 2008, entitled "Imaging and tools for use with moving organs,"

all of which claim the benefit of U.S. Provisional Patent Application Nos.:

60/906,091 filed on Mar. 8, 2007,
60/924,609 filed on May 22, 2007,
60/929,165 filed on Jun. 15, 2007,
60/935,914 filed on Sep. 6, 2007, and
60/996,746 filed on Dec. 4, 2007, all entitled "Apparatuses and methods for performing medical procedures on cyclically-moving body organs," and all of which US Provisional patent applications are incorporated herein by reference.

The present application is related to the following patent applications, both of which are incorporated herein by reference:

PCT Application PCT/IL2009/00610 to Iddan (published as WO 09/153794), filed on Jun. 18, 2009, entitled "Stepwise advancement of a medical tool"

U.S. patent application Ser. No. 12/487,315 to Iddan (published as US 2009/0306547), filed Jun. 18, 2009, entitled "Stepwise advancement of a medical tool,"

both of which claim the benefit of U.S. Provisional Patent Application No. 61/129,331 to Iddan, filed on Jun. 19, 2008, entitled "Stepwise advancement of a medical tool."

FIELD OF EMBODIMENTS OF THE INVENTION

Applications of the present invention generally relate to medical imaging. Specifically, applications of the present invention relate to image processing and tool actuation during medical procedures.

BACKGROUND

In the process of angiography, a contrast agent is typically administered to designated vasculature, and is then imaged by means of a medical imaging modality (such as fluoroscopy). The resulting angiographic images are also known as angiograms. Such angiograms may then be used for constructing a road map of the vasculature, and/or for performing measurements.

WO 08/107,905 to Iddan describes apparatus for use with a portion of a subject's body that moves as a result of cyclic activity of a body system. An imaging device acquires a plurality of image frames of the portion. A sensor senses a phase of the cyclic activity. A medical tool performs a function with respect to the portion. A control unit generates a stabilized set of image frames of the medical tool disposed within the portion, actuates the tool to perform the function or move, in response to the sensor sensing that the cyclic activity is at a given phase thereof, and inhibits the tool from performing the action or moving in response to the sensor sensing that the cyclic activity is not at the given phase. A display facilitates use of the tool by displaying the stabilized set of image frames.

An article by Turski et al., entitled "Digital Subtraction Angiography 'Road Map'" (American Journal of Roentgenology, 1982) describes a technique called roadmapping.

U.S. Pat. No. 4,878,115 to Elion describes a method in which a dynamic coronary roadmap of the coronary artery system is produced by recording and storing a visual image of the heart creating a mask sequence, recording and storing another dynamic visual image of the heart after injection of a contrast medium thereby creating a contrast sequence, matching the different durations of two sequences and subtracting the contrast sequence from the mask sequence producing a roadmap sequence. The roadmap sequence is then replayed and added to live fluoroscopic images of the beating heart. Replay of the roadmap sequence is triggered by receipt of an ECG R-wave. The result is described as a dynamically moving coronary roadmap image which moves in precise synchronization with the live incoming fluoroscopic image of the beating heart.

U.S. Pat. No. 4,709,385 to Pfeiler describes an x-ray diagnostics installation for subtraction angiography, which has an image memory connected to an output of an x-ray image intensifier video chain which has a number of addresses for storing individual x-ray video signals obtained during a dynamic body cycle of a patient under observation. A differencing unit receives stored signals from the image memory as well as current video signals and subtracts those signals to form a superimposed image. Entry and readout of signals to and from the image memory is under the command of a control unit which is connected to the patient through, for example, an EKG circuit for identifying selected occurrences in the body cycle under observation. Entry and readout of data from the image memory is described as thereby being controlled in synchronization with the selected occurrences in the cycle.

U.S. Pat. Nos. 5,054,045, 5,457,728, 5,586,201 and 5,822,391 to Whiting et al. generally describe a method of displaying details of a coronary artery lesion in a cineangiogram, by digitally adjusting each frame of the cineangiogram so that the lesion is continually displayed at a fixed location on a display screen. The remaining cardiac anatomy is described as appearing to move, in background, past a stationary arterial segment, thus making the displayed arterial segment easier to identify and to examine by medical personnel. Cineangiographic image frames are digitized and processed by an image processor and the image frames are digitally shifted to place the arterial segment in substantially the same viewing location in each frame. Sequential image frames may be presented to the viewer as a stereoscopic pair, to produce pseudostereopsis. The arterial segment is described as appearing to the viewer in foreground, as if it was floating in front of the remaining cardiac anatomy. Image frames may be further processed to aid examination by medical personnel. Frames are described as being averaged to reduce quantum noise and to blur any structure noise. Frame averaging is described as being used to make numerical measurements of arterial cross-section.

U.S. Pat. No. 5,293,574 to Roehm et al. describes an x-ray fluorographic system which produces a cineangiogram and enables a feature in the image to be identified with a cursor and automatically tracked in subsequent images. The identified feature, such as a suspected lesion in a coronary artery, is located in each x-ray frame of the cineangiogram and the data is described as being displayed such that the feature remains motionless in the center of each successive image.

U.S. Pat. No. 5,809,105 to Roehm et al. describes an x-ray fluorographic system which produces frame images at a low dose rate for both on-line and off-line use. Background noise is filtered by first producing a mask which defines the boundaries of the structural features of interest. The mask is used to select the background pixels for filtering, while enabling the structural pixels to pass unfiltered to the display.

U.S. Pat. No. 6,088,488 to Hardy et al. describes a reference image R that is selected and a region of interest (ROI) that is interactively selected encompassing a desired structure from a sequence of images of a moving structure. This ROI is cross-correlated with other real-time images by multiplication in the Fourier frequency domain, to determine if the desired structure is present in the image. If the structure is present, this image may be averaged with other images in which the structure is present to produce higher resolution adaptively averaged images. The technique is described as being particularly useful in imaging coronary vessels. An alternative embodiment is described according to which the offset of the desired structure is calculated in a series of images. The images are then described as being sorted by this offset, and played back in that order to provide a "movie-like" display of the desired structure moving with the periodic motion.

U.S. Pat. No. 6,195,445 to Dubuisson-Jolly et al. describes a technique of displaying a segment of a coronary artery in a stabilized cineangiogram. A computer system receives a sequence of images of a conventional cineangiogram. A user displays a first image on a monitor and selects a point on an arterial segment. The computer system invokes an image tracking procedure that employs active optimal polyline contours to locate the arterial segment and a fixed point in each of the image frames of the conventional cineangiogram. The computer system produces a stabilized cineangiogram by translating the images to place the arterial segment in substantially the same viewing location in each one of the image frames.

U.S. Pat. No. 6,788,827 to Makram-Ebeid describes an image processing method for processing the images of an image sequence comprising steps of determining image data related to first points of an Object of Interest observed in a first image, said Object of Interest having possible movements, and image data related to correlated points found in a second image of the sequence, and based on said image data, of estimating parameters of sets of transformation functions, which transformation functions transform said first points into said correlated points and, from said parameters, of determining one Warping Law that automatically transforms said given Object of Interest of the first image into the same object in the second image of the sequence for following and locating said Object of Interest in said second image of the sequence. The method is described as being applicable to medical imaging, and X-ray examination apparatus.

U.S. Pat. No. 7,289,652 to Florent et al. describes a medical viewing system for displaying a sequence of images of a medical intervention that comprises moving and/or positioning a tool in a body organ, which tool is carried by a support to which at least one marker is attached at a predetermined location with respect to the tool, comprising means for acquiring the sequence of images, and for processing said images during the medical intervention, wherein: extracting means for automatically extracting at least one marker that is attached to the tool support and that neither belongs to the tool nor to the body organ, and yielding the marker location information; computing means for automatically deriving the tool location information from the marker location information, and enhancing means for improving the visibility of the tool and/or the body organ in order to check whether the medical intervention stages are successfully carried out.

An article by Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137) describes the examination of a multiscale second order local structure of an image (Hessian), with the purpose of developing a vessel enhancement filter. A vesselness measure is obtained on the basis of all eigenvalues of the Hessian. This measure is tested on two dimensional DSA and three dimensional aortoiliac and cerebral MRA data. Its clinical utility is shown by the simultaneous noise and background suppression and vessel enhancement in maximum intensity projections and volumetric displays.

An article by Dijkstra, entitled "A Note on Two Problems in Connexion with Graphs" (Numerische Mathematik 1, 269-271, 1959), describes the consideration of n points (nodes), some or all pairs of which are connected by a branch, wherein the length of each branch is given. The discussion is restricted to the case where at least one path exists between any two nodes. A first problem considered is the construction of a tree of minimum total length between the n nodes. A second problem considered is finding the path of minimum total length between two given nodes.

An article by Timinger et al., entitled "Motion compensated coronary interventional navigation by means of diaphragm tracking and elastic motion models" (Phys Med Biol. 2005 Feb. 7; 50(3):491-503) presents a method for compensating the location of an interventional device measured by a magnetic tracking system for organ motion and thus registering it dynamically to a 3D virtual roadmap. The motion compensation is accomplished by using an elastic motion model which is driven by the ECG signal and a respiratory sensor signal derived from ultrasonic diaphragm tracking.

An article by Timinger et al., entitled "Motion compensation for interventional navigation on 3D static roadmaps based on an affine model and gating" (Phys Med Biol. 2004 Mar. 7; 49(5):719-32), describes a method for enabling cardiac interventional navigation on motion-compensated 3D static roadmaps.

An article by Zarkh et al., entitled "Guide wire navigation and therapeutic device localization for catheterization procedure" (International Congress Series 1281 (2005) 311-316), describes research into the development of a system for precise real-time localization of a guide wire tip and therapeutic device, in order to provide assistance in guide wire navigation and accurate device deployment within the coronary arteries with minimal contrast material injection. The goal is described as being achieved by real time monitoring of the guide wire tip and therapeutic device in a sequence of fluoroscopic images, and automatic registration to the 3D model of the artery.

WO 08/007,350 to Sazbon et al. describes a tool for real-time registration between a tubular organ and a device, and a method that utilizes the proposed tool for presenting the device within a reference model of the tubular organ. The proposed tool or markers attached thereto, and the device are shown by one imaging modality and the tubular organ is shown by a different imaging modality, but no imaging modality shows both. Due to the usage of the proposed tool, the registration between the device and the tubular organ is significantly simplified and is described as thus, increasing both speed and accuracy.

At the Transvascular Cardiovascular Therapeutics (TCT) conference held in Washington D.C., USA in October 2008, Paieon Inc. demonstrated the CardiOp-THV system for real-time navigation and positioning of a trans-catheter heart valve.

At the TCT conference held in San Francisco, USA in September 2009, Paieon Inc. demonstrated the IC-PRO Comprehensive Imaging Workstation for providing assistance in cardiac catheterization procedures. The Workstation was described as providing the following functionalities: 3D reconstruction and analysis and left ventricle analysis; Virtual planning of single-stent, multiple-stent, or bifurcation procedures; Device visualization during positioning of single or multiple stenting and post-deployment inflation; Device enhancement, post-deployment analysis and fusion of stent- and vessel images; and PACS/CVIS connectivity.

Direct Flow Medical Inc. (Santa Rosa, Calif., USA) manufactures the Direct Flow valve.

The following references may be of interest:

U.S. Pat. No. 3,871,360 to Van Horn et al., U.S. Pat. No. 3,954,098 to Dick et al., U.S. Pat. No. 4,016,871 to Schiff, U.S. Pat. No. 4,031,884 to Henzel, U.S. Pat. No. 4,245,647 to Randall, U.S. Pat. No. 4,270,143 to Morris, U.S. Pat. No. 4,316,218 to Gay, U.S. Pat. No. 4,382,184 to Wernikoff, U.S. Pat. No. 4,545,390 to Leary, U.S. Pat. No. 4,723,938 to Goodin et al., U.S. Pat. No. 4,758,223 to Rydell, U.S. Pat. No. 4,849,906 to Chodos et al., U.S. Pat. No. 4,865,043 to Shimoni, U.S. Pat. No. 4,920,413 to Nakamura, U.S. Pat. No. 4,991,589 to Hongo et al., U.S. Pat. No. 4,994,965 to Crawford et al., U.S. Pat. No. 5,020,516 to Biondi, U.S. Pat. No. 5,062,056 to Lo et al., U.S. Pat. No. 5,176,619 to Segalowitz, U.S. Pat. No. 5,295,486 to Wollschlager, U.S. Pat. No. 5,486, 192 to Walinsky, U.S. Pat. No. 5,538,494 to Matsuda, U.S. Pat. No. 5,619,995 to Lobodzinski, U.S. Pat. No. 5,630,414 to Horbaschek, U.S. Pat. No. 5,764,723 to Weinberger, U.S. Pat. No. 5,766,208 to McEwan, U.S. Pat. No. 5,830,222 to Makower, U.S. Pat. No. 5,971,976 to Wang et al., U.S. Pat. No. 6,126,608 to Kemme et al., U.S. Pat. No. 6,233,478 to Liu, U.S. Pat. No. 6,246,898 to Vesely et al., U.S. Pat. No. 6,331,181 to Tierney, U.S. Pat. No. 6,377,011 to Ben-Ur, U.S. Pat. No. 6,442,415 to Bis et al., U.S. Pat. No. 6,473,635 to Rasche, U.S. Pat. No. 6,496,716 to Langer et al., U.S. Pat. No. 6,532,380 to Close et al., U.S. Pat. No. 6,666,863 to Wentzel et al., U.S. Pat. No. 6,704,593 to Stainsby, U.S. Pat. No. 6,708,052 to Mao et al., U.S. Pat. No. 6,711,436 to Duhaylongsod, U.S. Pat. No. 6,728,566 to Subramanyan, U.S. Pat. No. 6,731,973 to Voith, U.S. Pat. No. 6,786,896 to Madhani et al., U.S. Pat. No. 6,858,003 to Evans et al., U.S. Pat. No. 6,937,696 to Mostafavi, U.S. Pat. No. 6,959,266 to Mostafavi, U.S. Pat. No. 6,973,202 to Mostafavi, U.S. Pat. No. 6,980,675 to Evron et al., U.S. Pat. No. 6,999,852 to Green, U.S. Pat. No. 7,085,342 to Younis et al., U.S. Pat. No. 7,155,046 to Aben et al., U.S. Pat. No. 7,155,315 to Niemeyer et al., U.S. Pat. No. 7,180,976 to Wink et al., U.S. Pat. No. 7,191,100 to Mostafavi, U.S. Pat. No. 7,209,779 to Kaufman, U.S. Pat. No. 7,269,457 to Shafer, U.S. Pat. No. 7,321,677 to Evron et al., U.S. Pat. No. 7,339,585 to Verstraelen et al., U.S. Pat. No. 7,587,074 to Zarkh et al.;

US 2002/0049375 to Strommer et al., US 2002/0188307 to Pintor, US 2003/0018251 to Solomon, US 2003/0023141 to Stelzer, US 2003/0157073 to Peritt, US 2004/0077941 to Reddy et al., US 2004/0097805 to Verard, US 2004/0176681 to Mao et al., US 2005/0008210 to Evron et al., US 2005/0054916 to Mostafavi, US 2005/0090737 to Burrel et al., US 2005/0107688 to Strommer, US 2005/0137661 to Sra, US 2005/0143777 to Sra, US 2006/0074285 to Zarkh et al., US 2006/0287595 to Maschke, US 2006/0058647 to Strommer et al., US 2007/0053558 to Puts et al., US 2007/0106146 to Altmann et al., US 2007/0142907 to Moaddeb et al., US 2007/0173861 to Strommer, US 2007/0208388 to Jahns, US 2007/0219630 to Chu;

WO 94/010904 to Nardella, WO 01/43642 to Heuscher, WO 03/096894 to Ho et al., WO 05/026891 to Mostafavi, WO 05/124689 to Manzke, WO 06/066122 to Sra, WO 06/066124 to Sra;

"3D imaging in the studio and elsewhere," by Iddan et al. (SPIE Proceedings Vol. 4298, 2001);

"4D smoothing of gated SPECT images using a left-ventricle shape model and a deformable mesh," by Brankov et al., (Nuclear Science Symposium Conference Record, 2004 IEEE, October 2004, Volume: 5, 2845-2848);

"4D-CT imaging of a volume influenced by respiratory motion on multi-slice CT Tinsu Pan," by Lee et al., (Medical Physics, February 2004, Volume 31, Issue 2, pp. 333-340);

"Assessment of a Novel Angiographic Image Stabilization System for Percutaneous Coronary Intervention" by Boyle et al. (Journal of Interventional Cardiology," Vol. 20 No. 2, 2007);

"Cardiac Imaging: We Got the Beat!" by Elizabeth Morgan (Medical Imaging, March 2005);

"Catheter Insertion Simulation with Combined Visual and Haptic Feedback," by Zorcolo et al. (Center for Advanced Studies, Research and Development in Sardinia);

"Full-scale clinical implementation of a video based respiratory gating system," by Ramsey et al., (Engineering in Medicine and Biology Society, 2000. Proceedings of the 22nd Annual International Conference of the IEEE, 2000, Volume: 3, 2141-2144);

"New 4-D imaging for real-time intraoperative MRI: adaptive 4-D scan," by Tokuda et al. (Med Image Comput Assist Interv Int Conf. 2006; 9 (Pt 1):454-61);

"Noninvasive Coronary Angiography by Retrospectively ECG-Gated Multislice Spiral CT," by Achenbach et al., (Circulation. 2000 Dec. 5; 102(23):2823-8);

"Prospective motion correction of X-ray images for coronary interventions," by Shechter et al. (IEEE Trans Med Imaging. 2005 April; 24(4):441-50);

"Real-time interactive viewing of 4D kinematic MR joint studies," by Schulz et al. (Med Image Comput Assist Interv Int Conf. 2005; 8(Pt 1):467-73.);

"Spatially-adaptive temporal smoothing for reconstruction of dynamic and gated image sequences," by Brankov et al., (Nuclear Science Symposium Conference Record, 2000 IEEE, 2000, Volume: 2, 15/146-15/150);

"Three-Dimensional Respiratory-Gated MR Angiography of the Coronary Arteries: Comparison with Conventional Coronary Angiography," by Post et al., (AJR, 1996; 166: 1399-1404).

SUMMARY OF EMBODIMENTS

For some applications of the present invention, apparatus and methods are provided for use in image processing and tool actuation in the course of a coronary angioplasty procedure. For example, apparatus and methods are provided for: automated generation of a road-map, the generation of automated measurements, automatic image stabilization, automatic image enhancement, tool positioning and tool deployment.

For some applications, a road map is displayed together with a stabilized image stream.

Typically, image processing as described in the present application is performed on-line. However, the scope of the present application includes performing the techniques described herein off line.

Although many of the applications of the present invention are described with reference to the diagnosis and treatment of the coronary arteries in the context of coronary angiography and/or angioplasty, the scope of the present invention includes applying the apparatus and methods described herein to other medical procedures. The scope of the present invention includes applying the techniques described herein to any bodily lumen or cavity on which diagnosis and/or treatment may be performed, including but not limited to the vascular system, chambers of the heart, the bronchial tract, the gastro-intestinal tract, or any combination thereof, and using any form of imaging and any applicable medical tool. For example, the scope of the present invention includes applying the apparatus and methods described herein to valve replacement or repair, closure of septal defects, ablation of cardiac tissue, or other medical interventions, as described in further detail hereinbelow.

For some applications, one or more of the procedures described herein is performed under guidance of an image stream that has been image tracked with respect to a portion of a tool that is used for the procedure. Typically, performing the procedure using such image guidance facilitates the performance of the procedure by a healthcare professional.

For some applications, a medical tool is actuated in synchronization with the cyclical motion of the organ being imaged. For some applications, in addition to the medical tool being actuated in synchronization with the cyclical motion of an organ, a stabilized image stream of the organ is displayed.

For some applications, the techniques described herein are performed in combination with techniques described in PCT Application PCT/IL2008/000316 to Iddan (published as WO 08/107,905), filed on Mar. 9, 2008, entitled "Imaging and tools for use with moving organs," which is incorporated herein by reference.

For some applications, the techniques described herein are performed in combination with techniques described in PCT Application PCT/IL2009/00610 to Iddan (published as WO 09/153794), filed on Jun. 18, 2009, entitled "Stepwise advancement of a medical tool," which is incorporated herein by reference.

For some applications, the techniques described herein are performed in combination with techniques described in PCT Application PCT/IL2009/00610 to Iddan (published as WO 09/153794), filed on Jun. 18, 2009, entitled "Stepwise advancement of a medical tool," which is incorporated herein by reference.

There is therefore provided, in accordance with some applications of the present invention, a method, including:
  receiving into at least one processor a set of images of blood vessels of a subject;
  generating a road map of the subject's blood vessels, by automatically:
    deriving at least one image from the set of images of the blood vessels, based upon visibility of at least a portion of the blood vessels in the set of images; and
    in the derived image, determining a location of edge lines of at least some of the portion of the blood vessels in the image; and
  generating an output by the processor, based on the road map.

For some applications, generating the output includes overlaying the edge lines on an image stream that is based upon the set of images.

For some applications, generating the output includes overlaying the edge lines on a single image that is derived from the set of images.

For some applications, generating the road map includes generating a road map that corresponds to a given phase of a motion cycle of the blood vessels, and generating the output includes overlaying the road map on an image stream of the blood vessels that is gated to the given phase.

For some applications, generating the road map includes generating the road map in real time.

For some applications, generating the road map includes generating the road map in near real time.

For some applications, the method further includes generating distance indicators along the edge lines.

For some applications, generating the road map further includes automatically enhancing the at least some of the portion of the blood vessels in the derived image.

For some applications, determining the location of the edge lines includes determining a location of discontinuous edge lines using image processing, and filling gaps in the discontinuous edge lines using a gap-filling algorithm.

For some applications, deriving the at least one image from the set of images includes selecting a single image from the set of images, based upon visibility of at least a portion of the blood vessels in the set of images.

For some applications, deriving the at least one image from the set of images includes selecting two or more images from the set of images, based upon visibility of at least a portion of the blood vessels in the set of images, and generating an image, based upon the two or more images.

For some applications, generating the image based upon the two or more images includes aggregating the two or more images.

For some applications, generating the road map includes, using image processing, automatically deriving lines that correspond to paths of the at least some of the portion of the blood vessels in the derived image, and determining the location of the edge lines includes determining the location of the edge lines based upon the lines that correspond to the paths.

For some applications, the lines that correspond to the paths are discontinuous and have end points at discontinuities in the lines, and the method further includes automatically generating continuous lines that correspond to the paths, by bridging the discontinuities in the discontinuous lines.

For some applications, determining the location of the edge lines includes using a penalty function that is based upon the lines that correspond to the paths.

There is further provided, in accordance with some applications of the present invention, apparatus, including:
an image-acquisition device configured to acquire a set of images of blood vessels of a subject;
a display; and
at least one processor, including:
image-receiving functionality configured to receive the set of images into the processor;
image-derivation functionality configured to automatically derive at least one image from the set of images of the blood vessels, based upon visibility of at least a portion of the blood vessels in the set of images; and
edge-line-determination functionality configured to automatically generate a road map by determining a location of edge lines of at least some of the portion of the blood vessels in the derived image; and
display-driving functionality configured to drive the display to display an output to a user based upon the road map.

For some applications, the processor further includes distance-indicating functionality configured to generate distance indicators along the edge lines, and the display-driving functionality is configured to drive the display to display the distance indicators along the edge lines.

For some applications, the processor further includes image-enhancement functionality configured to automatically enhance the at least some of the portion of the blood vessels in the derived image.

For some applications, the processor further includes line-derivation functionality configured, using image processing, to automatically derive lines that correspond to paths of at least the some of the portion of the blood vessels in the image, and the edge-line-determination functionality is configured to determine the location of the edge lines based upon the lines that correspond to the paths.

For some applications, the lines that correspond to the paths are continuous and have end points at discontinuities in the lines, and the processor further includes line-bridging functionality configured to, automatically, generate continuous lines that correspond to the paths of the portion of the blood vessels in the image, by bridging the discontinuities in the discontinuous lines.

There is additionally provided, in accordance with some applications of the present invention, a method, including:
receiving into at least one processor at least one image of blood vessels of a subject;
using image processing, automatically deriving discontinuous lines that correspond to paths of at least a portion of the blood vessels in the image, the lines having end points at discontinuities in the lines;
automatically generating continuous lines that correspond to the paths of the portion of the blood vessels in the image by bridging the discontinuities in the discontinuous lines; and
generating an output by the processor, based on the continuous lines.

For some applications, receiving the at least one image includes receiving into the processor a plurality of images of the blood vessels, and generating the output includes overlaying the lines on an image stream that is based upon the plurality of images.

For some applications, generating the output includes overlaying the lines on the image of the blood vessels.

For some applications, generating the output includes overlaying the lines on a current real time image stream of the blood vessels.

For some applications, generating the lines includes generating lines corresponding to the paths of the blood vessels during a given phase of a motion cycle of the blood vessels, and generating the output includes overlaying the lines on an image stream of the blood vessels that is gated to the given phase.

For some applications, generating the continuous lines includes generating the continuous lines in real time.

For some applications, generating the continuous lines includes generating the continuous lines in near real time. i For some applications, the method further includes automatically determining a location of edge lines of the portion of the blood vessels, based upon the lines that correspond to the paths.

For some applications, deriving the discontinuous lines includes deriving discontinuous lines that correspond to center lines, of the portion of the blood vessels.

For some applications, deriving the discontinuous lines includes deriving lines corresponding to paths of the blood vessels, based upon the lines having greater visibility than other lines corresponding to paths of the blood vessels in the at least one image.

For some applications, adjacent to at least one first end point of the end points, there are a plurality of second end points of the end points, and bridging the discontinuities includes determining to which of the second end points to bridge from the first end point.

For some applications, receiving the image includes receiving an image that was acquired in a presence of a contrast agent.

For some applications, bridging the discontinuities includes bridging the discontinuities based upon a shortest-path algorithm.

For some applications, brdging the discontinuities includes bridging the discontinuities based upon a known structure of the portion of the blood vessels.

There is further provided, in accordance with some applications of the present invention, apparatus, including:
an image-acquisition device configured to acquire at least one image of blood vessels of a subject;
a display; and
at least one processor, including:
image-receiving functionality configured to receive the at least one image into the processor;
line-derivation functionality configured, using image processing, to automatically derive discontinuous lines that correspond to paths of at least a portion of the blood vessels in the image, the lines having end points at discontinuities in the lines;
line-bridging functionality configured to, automatically, generate continuous lines that correspond to the paths of the portion of the blood vessels in the image, by bridging the discontinuities in the discontinuous lines; and display-driving functionality configured to drive the display to display an output to a user based on the continuous lines.

For some applications, the processor further includes edge-line-determination functionality configured to determine a location of edge lines of the portion of the blood vessels, based upon the lines that correspond to the paths.

There is additionally provided, in accordance with some applications of the present invention, a method for use with blood vessels of a subject that move cyclically, in accordance with a motion cycle, including:

receiving into at least one processor a set of images of the blood vessels;

automatically, deriving at least one image from the set of images of the blood vessels, based upon:
 (a) timing of acquisition of images from the set of images with respect to the motion cycle, and
 (b) visibility of at least a portion of the blood vessels in the set of images;

generating a road map based upon the derived image; and
generating an output based upon the road map.

For some applications, receiving the set of images includes receiving a set of angiographic images.

For some applications, deriving the at least one image from the set of images includes selecting a single image from the set of images, based upon the (a) timing of acquisition of images from the set of images with respect to the motion cycle, and (b) visibility of at least a portion of the blood vessels in the set of images.

For some applications, deriving the at least one image from the set of images includes:

selecting two or more images from the set of images, based upon the (a) timing of acquisition of images from the set of images with respect to the motion cycle, and (b) visibility of at least a portion of the blood vessels in the set of images; and generating an image, based upon the two or more images.

For some applications, generating the image based upon the two or more images includes aggregating the two or more images.

There is further provided, in accordance with some applications of the present invention, apparatus for use with blood vessels of a subject that move cyclically, in accordance with a motion cycle, including:

an image-acquisition device configured to acquire a set of images of the blood vessels;
a display; and
at least one processor, including:
 image-receiving functionality configured to receive the set of images into the processor;
 image-derivation functionality configured to automatically derive at least one image from the set of images of the blood vessels, based upon:
  (a) timing of acquisition of images from the set of images with respect to the motion cycle, and
  (b) visibility of at least a portion of the blood vessels in the set of images;
 road-map-generation functionality configured to generate a road map based upon the derived image; and
 display-driving functionality configured to drive the display to display an output to a user based upon the road map.

There is further provided, in accordance with some applications of the present invention, a method, including:

generating a road map of a blood vessel;
subsequently, inserting a tool into the blood vessel;
while the tool is inside the blood vessel, determining a position of the tool; and
modifying the road map to account for the determined position of the tool.

For some applications, the tool includes a wire, and inserting the tool into the blood vessel includes inserting the wire into the blood vessel.

For some applications, the tool includes a catheter, and inserting the tool into the blood vessel includes inserting the catheter into the blood vessel.

There is additionally provided, in accordance with some applications of the present invention, apparatus, including:

an image-acquisition device configured to acquire a set of images of blood vessels of a subject;
a tool configured to be placed inside one of the blood vessels;
a display; and
at least one processor, including:
 image-receiving functionality configured to receive the set of images into the processor;
 road-map-generation functionality configured to generate a road map of the blood vessels, based upon the set of images;
 tool-location functionality configured to determine a location of the tool subsequent to the generation of the road map; and
 road-map-modification functionality configured to modify the road map to account for the determined position of the tool; and
 display-driving functionality configured to drive the display to display an output to a user based on the modified road map.

There is further provided, in accordance with some applications of the present invention, a method for use with an image of blood vessels of a subject, including:

in response to a user designating a single point on the image:
 automatically identifying a target portion of a blood vessel in a vicinity of the designated point;
 performing quantitative vessel analysis on the target portion of the blood vessel; and
generating an output based upon the quantitative vessel analysis.

For some applications, the blood vessel includes a coronary artery, and performing the quantitative vessel analysis with respect to the blood vessel includes performing quantitative coronary angiography.

For some applications, identifying the target portion includes designating a longitudinal portion of the blood vessel having a proximal end that is at a first distance from the point in a proximal direction, and having a distal end that is at a second distance from the point in a distal direction.

For some applications, performing quantitative vessel analysis with respect to the longitudinal portion includes determining a minimum diameter of the blood vessel within the longitudinal portion.

For some applications, designating the longitudinal portion includes designating a longitudinal portion, the first and second distances of which are equal to each other.

For some applications, designating the longitudinal portion includes designating a longitudinal portion, the first and second distances of which are different from each other.

For some applications, designating the longitudinal portion includes designating a longitudinal portion, a sum of the first and second distances of which corresponds to a length of a given tool.

For some applications, identifying the target portion includes identifying a portion of the blood vessel that corresponds to a lesion.

For some applications, performing quantitative vessel analysis includes determining a minimum diameter of the lesion.

For some applications, performing quantitative vessel analysis includes determining a maximum diameter of the lesion.

For some applications, performing quantitative vessel analysis includes determining a length of the lesion.

For some applications, identifying the portion of the blood vessel that corresponds to the lesion includes identifying edge lines of the blood vessel.

For some applications, identifying the portion of the blood vessel that corresponds to the lesion includes identifying proximal and distal longitudinal locations of the blood vessel at which the lesion ends.

There is further provided, in accordance with some applications of the present invention, apparatus, including:
  a display configured to display an image of blood vessels of a subject;
  an input device; and
  at least one processor, including:
    target-identification functionality configured, in response to a user designating a single point on the image, using the input device, to automatically identify a target portion of a blood vessel in a vicinity of the designated point;
    quantitative-vessel-analysis functionality configured to perform quantitative vessel analysis on the target portion of the blood vessel; and
    display-driving functionality configured to drive the display to display an output in response to the quantitative vessel analysis.

There is additionally provided, in accordance with some applications of the present invention, a method for use with an image of blood vessels of a subject, including:
  in response to a user designating a single point on the image:
    automatically identifying a portion of a blood vessel in a vicinity of the designated point that corresponds to a lesion, by:
      automatically determining a location of edge lines of the blood vessel, and
      automatically determining longitudinal locations along the blood vessel that correspond to ends of the lesion; and
  generating an output in response to the identification of the portion that corresponds to the lesion.

For some applications, the method further includes performing quantitative vessel analysis with respect to the portion.

There is further provided, in accordance with some applications of the present invention, apparatus, including:
  a display configured to display an image of blood vessels of a subject;
  an input device; and
  at least one processor, including:
    lesion-identification functionality configured, in response to a user designating a single point on the image, using the input device, to identify a portion of a blood vessel in a vicinity of the designated point that corresponds to a lesion, by:
      automatically determining a location of edge lines of the blood vessel, and
      automatically determining longitudinal locations along the blood vessel that correspond to ends of the lesion; and
    display-driving functionality configured to drive the display to display an output in response to the identification of the portion that corresponds to the lesion.

For some applications, the processor further includes quantitative-vessel-analysis functionality configured to perform quantitative vessel analysis on the identified portion.

There is additionally provided, in accordance with some applications of the present invention, a method for use with an image of blood vessels of a subject, including:
  in response to a user designating a first longitudinal location of a blood vessel, and subsequently designating a plurality of additional longitudinal locations of the blood vessel,
  automatically determining a parameter of the blood vessel at each of the additional locations selected from the group consisting of:
    a diameter of the blood vessel associated with the additional location,
    a level of occlusion of the blood vessel associated with the additional location, and
    a longitudinal distance along the blood vessel associated with the additional location; and
  generating an output in response to the determined parameter at each of the locations.

For some applications, determining the selected parameter includes determining an average diameter of the blood vessel between the first longitudinal location and the additional location.

For some applications, determining the selected parameter includes determining a minimum diameter of the blood vessel between the first longitudinal location and the additional location.

For some applications, determining the selected parameter includes determining a diameter of the blood vessel at the additional location.

For some applications, determining the selected parameter includes determining a longitudinal distance from the first longitudinal location to the additional location.

For some applications, determining the selected parameter includes determining a longitudinal distance from an end of a lesion of the blood vessel to the additional location.

For some applications, determining the parameter includes determining a minimum lumen diameter associated with the additional location.

There is further provided, in accordance with some applications of the present invention, apparatus, including:
  a display configured to display an image of blood vessels of a subject;
  an input device; and
  at least one processor, including:
    parameter-determination functionality configured, in response to a user designating a first longitudinal location of a blood vessel, and subsequently designating a plurality of additional longitudinal locations of the blood vessel, to automatically determine a parameter of the blood vessel at each of the additional locations, the parameter selected from the group consisting of
      a diameter of the blood vessel associated with the additional location, a level of occlusion of the blood vessel associated with the additional location, and a longitudinal distance along the blood vessel associated with the additional location; and display-driving functionality configured to drive the display to display an output in response to the determined parameter.

There is additionally provided, in accordance with some applications of the present invention, a method for use with an image of blood vessels of a subject, including:

displaying a cursor in a vicinity of one of the blood vessels on the image; and in response to receiving an input from a user indicating that the cursor should be moved, only allowing movement of the cursor along a direction of paths of the blood vessels.

For some applications, only allowing movement of the cursor along the direction of the paths includes allowing movement of the cursor within the blood vessels along the direction of the paths.

For some applications, only allowing movement of the cursor along the direction of the paths includes allowing movement of the cursor alongside the blood vessels, along the direction of the paths.

There is further provided, in accordance with some applications of the present invention, apparatus, including:

a display;

an input device; and at least one processor, including:

display-driving functionality configured to drive the display to display a cursor in an image of blood vessels of a subject, in a vicinity of one of the blood vessels on the image; and cursor-control functionality configured (a) in response to receiving an input from a user, via the input device, indicating that the cursor should be moved, (b) only to allow movement of the cursor along a direction of paths of the blood vessels.

There is additionally provided, in accordance with some applications of the present invention, a method, including:

generating a sequence of endoluminal cross-sectional images of respective sections of a blood vessel of a subject;

generating an extraluminal image of the blood vessel;

determining that respective regions of the extraluminal image of the blood vessel correspond to the sections;

determining dimensions of at least some of the regions of the extraluminal image by performing quantitative vessel analysis with respect to the at least some of the regions of the extraluminal image; and displaying at least some of the endoluminal images of respective sections of the blood vessel together with the dimensions of the corresponding region.

For some applications, determining that respective regions of the extraluminal image of the blood vessel correspond to the sections includes registering the extraluminal image with the endoluminal images.

There is further provided, in accordance with some applications of the present invention, apparatus, including:

an endoluminal imaging device configured to acquire a sequence of endoluminal cross-sectional images of respective sections of a blood vessel of a subject;

an extraluminal imaging device configured to acquire at least one extraluminal image of the blood vessel;

a display; and at least one processor, including:

image-receiving functionality configured to receive the endoluminal and extraluminal images;

image-assigning functionality configured to determine that respective regions of the extraluminal image of the blood vessel correspond to the sections; and dimension-determining functionality configured to determine dimensions of at least some of the regions of the extraluminal image by performing quantitative vessel analysis with respect to the at least some of the regions of the extraluminal image; and display-driving functionality configured to drive the display to display at least some of the endoluminal images of respective sections of the blood vessel together with the dimensions of the corresponding region.

There is additionally provided, in accordance with some applications of the present invention, a method, including:

inserting a tool into a blood vessel;

while the tool is within the blood vessel, acquiring an extraluminal image of the blood vessel;

in the extraluminal image of the blood vessel, automatically detecting a location of a portion of the tool with respect to the blood vessel;

in response to detecting the location of the portion of the tool, automatically designating a target portion of the blood vessel that is in a vicinity of the portion of the tool; and using the extraluminal image, performing quantitative vessel analysis on the target portion of the blood vessel.

For some applications, the tool includes a balloon, and inserting the tool includes inserting the balloon.

For some applications, the tool includes a replacement valve, and inserting the tool includes inserting the replacement valve.

For some applications, the tool includes a stent, and inserting the tool includes inserting the stent.

For some applications, the tool includes a graft, and inserting the tool includes inserting the graft.

There is further provided, in accordance with some applications of the present invention, apparatus, including:

a tool configured to be placed inside a blood vessel of a subject;

an extraluminal image-acquisition device configured to acquire an image of the blood vessel, while the tool is inside the blood vessel;

a display; and at least one processor, including:

image-receiving functionality configured to receive the image into the processor;

tool-detection functionality configured to automatically detect a location of a portion of the tool, with respect to the blood vessel, in the image;

target-designation functionality configured, in response to detecting the location of the portion of the tool, to automatically designate a target portion of the blood vessel that is in a vicinity of the portion of the tool;

quantitative-vessel-analysis functionality configured to perform quantitative vessel analysis on the target portion of the blood vessel, using the image; and display-driving functionality configured to drive the display to display an output in response to the quantitative vessel analysis.

There is additionally provided, in accordance with some applications of the present invention, a method for imaging a tool inside a portion of a subject's body that undergoes motion, the method including:

acquiring a plurality of image frames of the portion of the subject's body;

image tracking the image frames by:

automatically identifying at least a feature of the tool in at least a portion of the image frames, and aligning the tool in image frames of the portion of the image frames, based on the automatic identifying; and displaying, as an image stream, the image-tracked image frames of the portion of the subject's body.

For some applications, aligning the tool includes translating at least one of the image frames.

For some applications, aligning the tool includes rotating at least one of the image frames.

For some applications, aligning the tool includes scaling at least one of the image frames.

For some applications, the tool includes a balloon, and automatically identifying at least the feature of the tool includes automatically identifying at least a feature of the balloon.

For some applications, the tool includes a stent, and automatically identifying at least the feature of the tool includes automatically identifying at least a feature of the stent.

For some applications, the tool includes a graft, and automatically identifying at least the feature of the tool includes automatically identifying at least a feature of the graft.

For some applications, the tool includes a replacement valve, and automatically identifying at least the feature of the tool includes automatically identifying at least a feature of the replacement valve.

For some applications, the tool includes a hole-closing tool for closing a hole in a septal wall, and automatically identifying at least the feature of the tool includes automatically identifying at least a feature of the hole-closing tool.

For some applications, the tool includes a valve-placement tool for facilitating placement of a replacement valve, and automatically identifying at least the feature of the tool includes automatically identifying at least a feature of the valve-placement tool.

For some applications, the tool includes a tool selected from the group consisting of: a catheter, an energy-application tool, a percutaneous-myocardial-revascularization tool, a substance-delivery tool, a tissue-repair tool, a trans-thoracic-needle, and a trans-bronchial needle, and automatically identifying at least the feature of the tool includes automatically identifying at least a feature of the selected tool.

For some applications, the tool includes a valve-repair tool, and automatically identifying at least the feature of the tool includes automatically identifying at least a feature of the valve-repair tool.

For some applications, the tool includes a valve-suturing tool for suturing a valve, and automatically identifying at least the feature of the tool includes automatically identifying at least a feature of the valve-suturing tool.

For some applications, the tool includes a valve-leaflet-clipping tool for clipping a valve, and automatically identifying at least the feature of the tool includes automatically identifying at least a feature of the valve-leaflet-clipping tool.

For some applications, displaying the image-tracked image frames includes displaying an image stream in which motion of the tool relative to the portion of the subject's body is visible, but motion of the tool that is the same as motion of the portion of the subject's body is not visible.

For some applications, displaying the image-tracked image frames includes displaying an image stream in which motion of the tool relative to the portion of the subject's body over a cycle of cyclical motion of the portion of the subject's body is shown.

For some applications, the method further includes designating at least one image frame as not providing sufficient visibility of the feature of the tool, and, in response to designating the image frame, not displaying the designated image frame in the image stream.

For some applications, the method further includes blending into each other a frame that was acquired immediately before acquisition of the designated image frame, and a frame that was acquired immediately after the acquisition of the designated image frame.

For some applications, identifying the feature of the tool includes deriving a feature of the tool from at least one portion of the tool that is generally visible in the image frames.

For some applications, deriving the feature includes deriving a virtual line that connects radiopaque portions of the tool.

For some applications, deriving the feature includes deriving an average location of radiopaque portions of the tool.

For some applications, identifying the feature of the tool includes identifying at least one radiopaque marker of the tool.

For some applications, identifying the marker includes distinguishing between the marker and contrast agent.

For some applications, identifying the marker includes distinguishing between the marker and overlap of a set of two portions of an image frame of the portion of the image frames, the set being selected from the group consisting of two blood vessels, two tool portions, a blood vessel and a tool portion, a blood vessel and a rib, and a tool portion and a rib.

For some applications, identifying the marker includes identifying the marker by accounting for blurring of the marker in a dynamic image stream that is based on the plurality of image frames.

There is further provided, in accordance with some applications of the present invention, apparatus for use with a portion of a subject's body that undergoes motion, the apparatus including:

a tool configured to be placed inside the portion;

an image-acquisition device configured to acquire a plurality of image frames of the portion of the subject's body;

a display; and at least one processor configured to image track the image frames, the processor including:

image-receiving functionality configured to receive the image frames into the processor;

tool-identifying functionality configured to automatically identify at least a feature of the tool in at least a portion of the image frames; and frame-aligning functionality configured to align the tool in image frames of the portion of the image frames, based on the automatic identifying; and display-driving functionality configured to drive the display to display, as an image stream, the image-tracked image frames of the portion of the subject's body.

There is further provided, in accordance with some applications of the present invention, apparatus including:

a sensor for sensing a phase of the cyclic activity;

a tool configured to be deployed within a blood vessel of a subject;

a balloon having a central portion disposed inside the tool and overhanging portions that are disposed outside the tool, the balloon configured to couple the tool to the blood vessel, by the balloon being inflated inside the tool while the balloon and the tool are inside the blood vessel; and a control unit configured, while the balloon and the tool are inside the blood vessel, to inflate the balloon such that at least one of the overhanging portions of the balloon becomes appositioned to an inner surface of the blood vessel, in response to the sensor sensing that the cyclic activity is at a given phase thereof.

For some applications, the control unit is configured to inflate the balloon continuously during at least one period selected from the group consisting of: a period before the balloon becomes appositioned to the surface, and a period after the balloon becomes appositioned to the surface.

For some applications, the tool includes a tool selected from the group consisting of a stent, a replacement valve, and a graft.

There is additionally provided, in accordance with some applications of the present invention, a method for imaging a portion of a body of a subject that undergoes motion, the method including:
  acquiring a plurality of image frames of the portion of the subject's body; and
  generating a stream of image frames in which a vicinity of a given feature of the image frames is enhanced, by:
    automatically identifying the given feature in each of the image frames,
    aligning the given feature in two or more image frames of the plurality of image frames,
    averaging sets of two or more of the aligned frames to generate a plurality of averaged image frames, and
    displaying as a stream of image frames the plurality of averaged image frames.

For some applications,
acquiring the plurality of image frames includes acquiring, sequentially, first and second image frames of the portion of the subject's body, and
generating the stream of image frames in which the vicinity of the given feature of the image frames is enhanced includes:
  generating a first moving average image frame using frames of the portion of the subject's body acquired prior to the acquisition of the first and second image frames;
  aligning the given feature in the first image frame with the given feature in the first moving-average image frame;
  when the given feature is aligned in the first image frame and the first moving-average image frame, averaging the first image frame and the first moving-average image frame to generate a second moving-average image frame;
  aligning the given feature in the second moving-average image frame and the second image frame;
  when the given feature is aligned in the second moving-average image frame and the second image frame, averaging the second image frame with the second moving-average image frame to generate a third moving-average image frame; and
  displaying, in an image stream, the first, second, and third moving-average image frames.

There is further provided, in accordance with some applications of the present invention, apparatus for use with a portion of a body of a subject that undergoes motion, the apparatus including:
  an image-acquisition device configured to acquire a plurality of image frames of the portion of the subject's body;
  a display; and
  at least one processor configured to generate a stream of image frames in which a vicinity of a given feature of the image frames is enhanced, the processor including:
    image-receiving functionality configured to receive the plurality of image frames into the processor,
    feature-identifying functionality configured to automatically identify the given feature in each of the image frames,
    image-alignment functionality configured to align the given feature in two or more image frames of the plurality of image frames, and
    image-averaging functionality configured to average sets of two or more of the aligned frames to generate a plurality of averaged image frames; and
    display-driving functionality configured to drive the display to display, as a stream of image frames, the plurality of averaged image frames.

There is further provided, in accordance with some applications of the present invention, a method for actuating a tool to perform a function on a body of a subject at a given phase of a motion cycle of the subject's body, the method including:
  determining a duration of the motion cycle;
  in a first motion cycle of the subject, detecting the given phase of the subject's motion cycle; and
  actuating the tool to perform the function at a given time after detecting the given phase of the first motion cycle, the given time being determined by subtracting a correction factor from the duration of the motion cycle.

For some applications, determining the duration of the cycle includes determining an average duration of a plurality of motion cycles of the subject.

For some applications, determining the duration of the cycle includes determining a duration of a single previous motion cycle of the subject.

For some applications, the tool includes a valve-placement tool for facilitating placement of a replacement valve, and actuating the tool to perform the function includes actuating the tool to facilitate placement of the valve.

For some applications, the tool includes a valve-repair tool for repairing a valve, and actuating the tool to perform the function includes actuating the tool to repair the valve.

For some applications, the tool includes a balloon, and actuating the tool to perform the function includes actuating the balloon to become inflated.

For some applications, the tool includes a stent, and actuating the tool to perform the function includes actuating the stent to become deployed.

For some applications, the tool includes a graft, and actuating the tool to perform the function includes actuating the graft to become deployed.

For some applications, the correction factor includes a detection-delay correction factor that is associated with a delay between an occurrence of the given phase and detection of the given phase, and actuating the tool to perform the function includes actuating the tool to perform the function at a given time after detecting the given phase of the first motion cycle, the given time being determined by subtracting the detection-delay correction factor from the duration of the motion cycle.

For some applications, the correction factor includes a mechanical-delay correction factor that is associated with a delay between generating a signal to actuate the tool to perform the function and performance of the function by the tool, and actuating the tool to perform the function includes actuating the tool to perform the function at a given time after detecting the given phase of the first motion cycle, the given time being determined by subtracting the mechanical-delay correction factor from the duration of the motion cycle.

There is further provided, in accordance with some applications of the present invention, apparatus for use with a portion of a subject's body that undergoes a motion cycle, including:
  a tool configured to perform a function on the portion of the subject's body; and
  at least one processor, including:
    cycle-measuring functionality configured to determine a duration of the motion cycle;
    phase-detection functionality configured, in a first motion cycle of the subject, to detect the given phase of the subject's motion cycle; and
    tool-actuation functionality configured to actuate the tool to perform the function at a given time after the detection of the given phase of the first motion cycle, the given time being determined by subtracting a correction factor from the duration of the motion cycle.

There is additionally provided, in accordance with some applications of the present invention, a method for imaging a portion of a body of a subject that undergoes a motion cycle, the method including:
  acquiring a plurality of image frames of the portion of the subject's body; and
  enhancing the image frames with respect to a first given feature of the image frames, by:
    image tracking the image frames with respect to the first given feature;
    identifying a second given feature in each of the image frames;
    in response to the identifying, reducing visibility of the second given feature in the image frames; and
    displaying, as a stream of image frames, the image frames that (a) have been image tracked with respect to the first given feature, and (b) have had reduced therein the visibility of the second given feature.

For some applications, reducing the visibility of the second feature includes reducing the visibility by a reduction factor that is a function of a distance of the second feature from the first feature.

For some applications, reducing visibility of the second given feature includes eliminating visibility of the second given feature.

For some applications, as a result of the motion cycle of the portion of the subject's body, the first given feature moves by an amount that is different from an amount of movement of the second given feature as a result of the motion cycle of the portion of the subject's body, and identifying the second feature includes identifying the second feature using a filter selected from the group consisting of a spatial filter and a temporal filter.

There is further provided, in accordance with some applications of the present invention, apparatus for use with a portion of a body of a subject that undergoes a motion cycle, the apparatus including:
  an image-acquisition device configured to acquire a plurality of image frames of the portion of the subject's body;
  a display; and
  at least one processor configured to enhance the image frames with respect to a first given feature of the image frames, the processor including:
    image-tracking functionality configured to image track the image frames with respect to the first given feature;
    feature-identifying functionality configured to identify a second given feature in each of the image frames;
    image-processing functionality configured, in response to the identifying, to reduce visibility of the second given feature in the image frames; and
    display-driving functionality configured to drive the display to display, as a stream of image frames, the image frames that (a) have been image tracked with respect to the first given feature, and (b) have had reduced therein the visibility of the second given feature.

There is additionally provided, in accordance with some applications of the present invention, a method for imaging a portion of a body of a subject that undergoes a motion cycle, the method including:
  acquiring a plurality of image frames of the portion of the subject's body;
  reducing visibility of a given feature within the image frames by masking the given feature in each of the image frames; and
  displaying, as a stream of image frames, the image frames in which the given feature has reduced visibility.

For some applications:
  masking the given feature in each of the image frames includes generating a plurality of masks, respective masks corresponding to given phases of the motion cycle, and
  applying the mask to the image frames includes applying to frames of the image stream that were acquired during respective phases of the motion cycle, a corresponding mask.

For some applications:
  acquiring the plurality of image frames includes gating the image frames with respect to a given phase of the motion cycle,
  masking the given feature in each of the image frames includes generating a mask based on an image frame that is gated with respect to the given phase of the motion cycle, and applying the mask to the gated image frames, and
  displaying the image frames includes displaying the gated, masked image frames.

For some applications, reducing the visibility of the given feature includes reducing the visibility in each of the image frames by a reduction factor that is a function of a distance of the given feature from a given portion of the image frame.

There is further provided, in accordance with some applications of the present invention, apparatus for use with a portion of a body of a subject that undergoes a motion cycle, the apparatus including:
  an image acquisition device configured to acquire a plurality of image frames of the portion of the subject's body;
  a display; and
  at least one processor including:
    image-receiving functionality configured to receive the image frames into the processor, and
    masking functionality that is configured to reduce visibility of a given feature within the image frames by masking the given feature in each of the image frames; and
    display-driving functionality configured to drive the display to display, as a stream of image frames, the image frames in which the given feature has reduced visibility.

For some applications:
  the processor includes gating functionality configured to gate the image frames with respect to a given phase of the motion cycle,
  the masking functionality is configured to generate a mask based on an image frame that is gated with respect to the given phase of the motion cycle, and to apply the mask to the gated image frames, and the display-driving functionality is configured to drive the display to display the gated, masked image frames.

There is additionally provided, in accordance with some applications of the present invention, a method, including:

generating a road map of a blood vessel in a portion of a body of a subject;

identifying, in the road map, a given feature that is within the portion of the subject's body, the given feature being visible even in images of the portion the generation of which does not include use of a contrast agent;

inserting a tool into the blood vessel;

determining a current location of at least a portion of the tool with respect to the given feature, by imaging the tool and the feature;

in response to the determined current location, determining a current position of the tool within the road map; and in response to determining the current position of the tool within the road map, displaying the current position of the tool with respect to the road map.

For some applications, the tool includes a balloon, and inserting the tool includes inserting the balloon.

For some applications, the tool includes a replacement valve, and inserting the tool includes inserting the replacement valve.

For some applications, the tool includes a stent, and inserting the tool includes inserting the stent.

For some applications, the tool includes a wire, and inserting the tool includes inserting the wire.

For some applications, the tool includes a catheter, and inserting the tool includes inserting the catheter.

For some applications, generating the road map includes generating a road map based upon a given phase of a motion cycle of the blood vessel, and determining the current location of the portion of the tool includes determining the current location of the portion of the tool during the given phase.

There is further provided, in accordance with some applications of the present invention, apparatus, including:

a tool configured to be inserted into a blood vessel of a portion of a body of a subject;

a display; and at least one processor, including:

road-map-generation functionality configured to generate a road map of the blood vessel in the portion of the subject's body;

feature-identifying functionality configured to identify, in the road map, a given feature that is within the portion of the subject's body, the given feature being visible even in images of the portion the generation of which does not include use of a contrast agent;

tool-location functionality configured to determine a current location of at least a portion of the tool with respect to the given feature, based on a current image of the tool and the feature;

tool-positioning functionality configured, in response to the determined current location of the tool, to determine a current position of the tool within the road map; and display-driving functionality configured, in response to determining the current position of the tool within the road map, to drive the display to display the current position of the tool with respect to the road map.

There is additionally provided, in accordance with some applications of the present invention, a method, including:

generating a road map of a blood vessel in a portion of a body of a subject;

identifying, in the road map, a given feature that is within the portion of the subject's body, the given feature being visible even in images of the portion the generation of which does not include use of a contrast agent;

generating an image stream of the blood vessel;

identifying the given feature in the image stream;

registering the road map to the image stream using the identified feature; and in response to the registration of the road map to the image stream, overlaying the road map on the image stream.

There is further provided, in accordance with some applications of the present invention, apparatus, including:

a tool configured to be inserted into a blood vessel of a portion of a body of a subject;

an image-acquisition device configured to acquire an image stream of the blood vessel;

a display; and at least one processor, including:

image-receiving functionality configured to receive the image stream into the processor;

road-map-generation functionality configured to generate a road map of the blood vessel in the portion of the subject's body;

road-map-feature-identifying functionality configured to identify, in the road map, a given feature that is within the portion of the subject's body, the given feature being visible even in images of the portion the generation of which does not include use of a contrast agent;

image-stream-feature-identifying functionality configured to identify the feature in the image stream;

registration-functionality configured to register the road map to the image stream using the identified feature; and display-driving functionality configured, in response to the registration of the road map to the image stream, to drive the display to overlay the road map on the image stream.

There is additionally provided, in accordance with some applications of the present invention, a method for use with a portion of a subject's body that assumes a plurality of different shapes, during respective phases of a motion cycle of the portion, the method including:

acquiring a plurality of image frames of the portion of the subject's body during the respective phases of the motion cycle of the portion;

designating at least one of the image frames as a baseline image frame, a shape of the portion in the baseline image frame being designated as a baseline shape of the portion;

identifying a non-baseline image frame of the plurality of image frames, by identifying an image frame in which the portion is not shaped in the baseline shape; and deforming the shape of the portion in the non-baseline image frame, such that the shape of the portion becomes more similar to the baseline shape of the portion than when the portion in the non-baseline image frame is not deformed; and subsequently to deforming the shape of the portion in the non-baseline image frame, displaying the baseline image frame and the non-baseline image frame in an image stream.

There is further provided, in accordance with some applications of the present invention, apparatus for use with a portion of a subject's body that assumes a plurality of different shapes, during respective phases of a motion cycle of the portion, the apparatus including:

an image-acquisition device configured to acquire a plurality of image frames of the portion of the subject's body during the respective phases of the motion cycle of the portion;
a display; and
at least one processor, including:
image-receiving functionality configured to receive the image frames into the processor,
baseline-designation functionality configured to designate at least one of the image frames as a baseline image frame, a shape of the portion in the baseline image frame being designated as a baseline shape of the portion;
non-baseline identification functionality configured to identify a non-baseline image frame of the plurality of image frames, by identifying an image frame in which the portion is not shaped in the baseline shape; and
shape-deformation functionality configured to deform the shape of the portion in the non-baseline image frame, such that the shape of the portion becomes more similar to the baseline shape of the portion than when the portion in the non-baseline image frame is not deformed; and
display-driving functionality configured, subsequently to the deforming of the shape of the portion in the non-baseline image frame, to drive the display to display the baseline image frame and the non-baseline image frame in an image stream.

There is additionally provided, in accordance with some applications of the present invention, a method for deploying an implantable tool at an implantation location of a blood vessel of a subject, including:
placing the tool at the implantation location, while the tool is in a non-deployed configuration;
while the tool in the non-deployed configuration is disposed at the implantation location, acquiring a plurality of image frames of the tool, during respective phases of a motion cycle of the blood vessel;
generating a stabilized image stream of the tool in the non-deployed configuration, by stabilizing the plurality of image frames;
determining from the stabilized image stream that, during the motion cycle of the blood vessel, the tool moves from the implantation location by a given distance in a first direction; and
accounting for the movement of the tool by the given distance, by deploying the tool at a deployment location that is distant from the implantation location in a second direction, the second direction being an opposite direction to the first direction.

For some applications, accounting for the movement of the tool by the given distance includes deploying the tool at a deployment location that is at the given distance from the implantation location in the second direction.

For some applications, accounting for the movement of the tool by the given distance includes deploying the tool at a deployment location that is at a distance from the implantation location in the second direction that is greater than the given distance.

For some applications, accounting for the movement of the tool by the given distance includes deploying the tool at a deployment location that is at a distance from the implantation location in the second direction that is less than the given distance.

For some applications, the tool includes a tool selected from the group consisting of a stent, a replacement valve, and a graft, and placing the tool at the implantation location includes placing the selected tool at the implantation location.

There is further provided, in accordance with some applications of the present invention, apparatus for deploying, including:
an implantable tool configured to be placed at an implantation location of a blood vessel of a subject, while the tool is in a non-deployed configuration;
an image acquisition device configured, while the tool is disposed at the implantation location in a non-deployed configuration, to acquire a plurality of image frames of the tool, during respective phases of a motion cycle of the blood vessel;
a display; and
at least one processor, including:
image-stabilization functionality configured to generate a stabilized image stream of the tool in the non-deployed configuration, by stabilizing the plurality of image frames;
motion-determination functionality configured to determine based on the stabilized image stream that, during the motion cycle of the blood vessel, the tool moves from the implantation location by a given distance in a first direction; and
deployment-location functionality configured to determine a deployment location for the tool that is distant from the implantation location in a second direction, by accounting for the movement of the tool by the given distance, the second direction being an opposite direction to the first direction; and
display-driving functionality configured to drive the display to display an output indicating the deployment location.

The present invention will be more fully understood from the following detailed description of embodiments thereof, taken together with the drawings, in which:

BRIEF DESCRIPTION OF THE DRAWINGS

FIGS. 23B-C show apparatus for facilitating synchronized inflation of a balloon, in accordance with some applications of the present invention;

FIG. 24 shows an image of an inflated coronary balloon that is enhanced, in accordance with some applications of the present invention;

DETAILED DESCRIPTION OF EMBODIMENTS

Terminology

Figure 1:
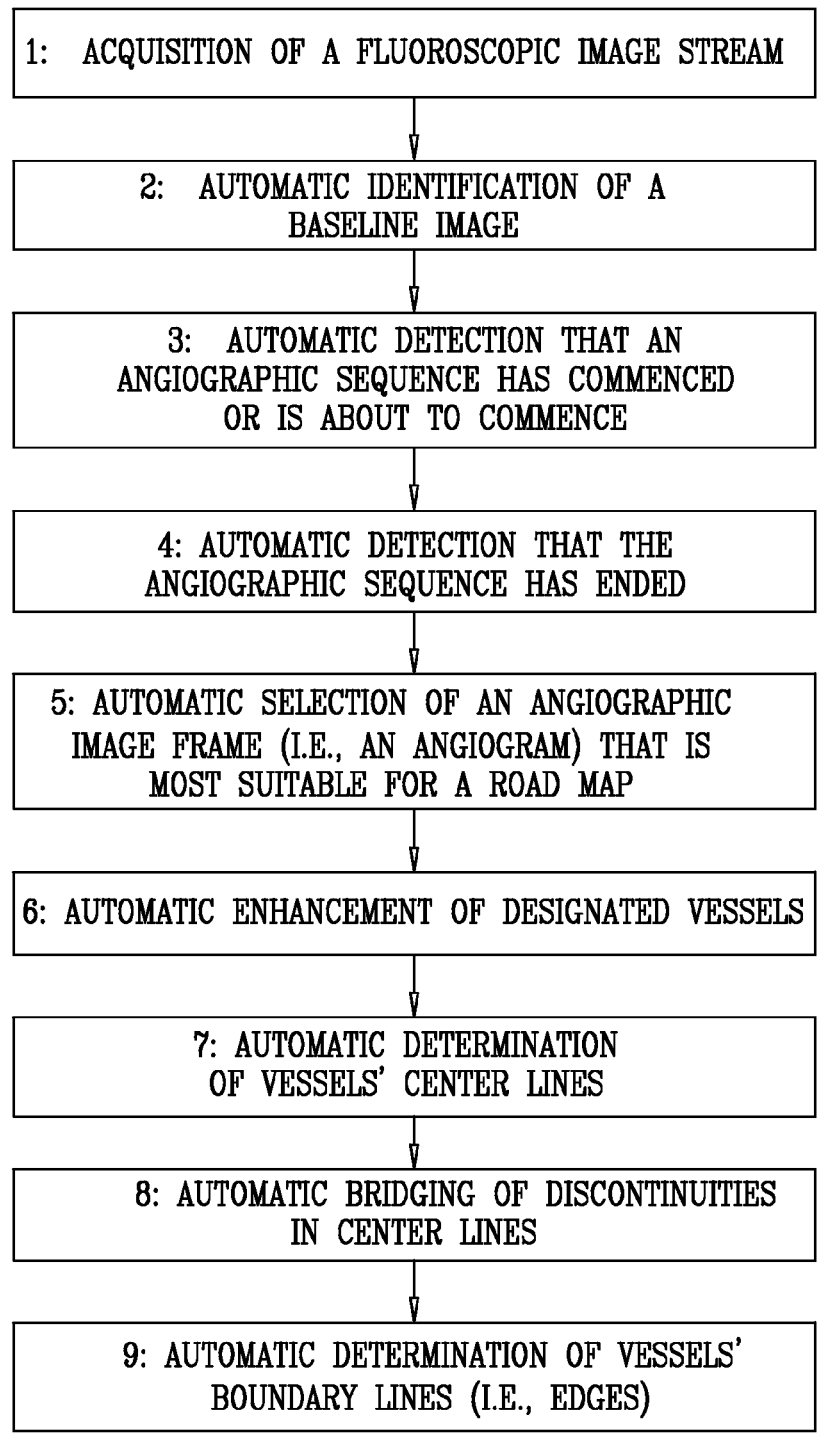
FIG. 1 is a flow chart, at least some of the steps of which are used to automatically generate a road map, in accordance with some applications of the present invention.

As used herein:

The term "physiological signal or process" refers to any physiological signal or process of the subject's body including, but not limited to, ECG (also known as EKG), blood pressure (e.g., systolic and diastolic), Peripheral Arterial Tone (PAT), EEG, respiration, the shifting/expansion/contraction/displacement of an organ, acquired images in which any of the above signals or processes may be observed, or any combination, derivation, extrapolation or manipulation thereof.

(Typically, a physiological signal or process as described herein is cyclical.)

The terms "medical tool," "tool", "device," and "probe" refer to any type of a diagnostic or therapeutic or other functional tool including, but not limited to, a cardiovascular catheter, a stent delivery and/or placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, or any combination thereof.

The terms "image" and "imaging" refer to any type of medical imaging, typically presented as a sequence of images and including, but not limited to, imaging using ionizing radiation, imaging using non-ionizing radiation, video, fluoroscopy, angiography, ultrasound, CT, MRI, PET, PET-CT, CT angiography, SPECT, Gamma camera imaging, Optical Coherence Tomography (OCT), Near-Infra-Red Spectroscopy (NIRS), Vibration Response Imaging (VRI), Optical Imaging, infrared imaging, electrical mapping imaging, other forms of Functional Imaging, or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof The terms "synchronization" and "gating," and derivations thereof, when used in reference to an image stream, describe the identification and selection of individual image frames from such image stream, wherein such frames are acquired at a same selected phase in a plurality of occurrences of a cyclical physiological signal or process.

The terms "gating" and "synchronization," and derivations thereof, when used in the context of synchronizing between an image display and one or more physiological signals or processes, or between the activation of a medical tool and one or more physiological signals or processes, are interchangeable. (The term "coherence" and derivations thereof are also used in the art to describe such techniques.)

The terms "gating" and "synchronization," and derivations thereof, when used in reference to a medical tool, describes the movement and/or application of the tool at a given phase of a cyclical physiological signal or process.

The terms "image tracking" or "tracking," and derivations thereof, are used to describe a process by which images (including images acquired at different phases in the motion of an organ) are at least partially aligned with one another by means of aligning among such images one or more features, that are observable in most or all of the images. Such features may be anatomical features, such as a segment of a vessel. Such features may also be physical features, such as a tool or a segment of a tool. For some applications, the alignment of the image frames is achieved by aligning a virtual feature or region that is derived from a manipulation (such as an average, a weighted average, a translation, a rotation, and/or a scaling) of the locations of one or more observable features or regions of the image frames. The term should be construed to be synonymous with the terms "video tracking," "frame tracking," and "object tracking." Tracking may be applied for the purpose of image stabilization, image enhancement, or a combination thereof.

The term "automatic," when used for describing the generation and utilization of the road map, means "without necessitating user intervention or interaction." (Such interaction or intervention may still however be optional in some cases.)

The term "real time" means without a noticeable delay.

The term "near real time" means with a short noticeable delay (such as approximately one or two motion cycles of the applicable organ, and, in the case of procedures relating to organs or vessels the motion of which are primarily as a result of the cardiac cycle, less than two seconds).

The term "on-line," when used in reference to image processing, or to measurements being made on images, means that the image processing is performed, and/or the measurements are made, intra-procedurally, in real time or near real time.

The term "stepwise," when used in reference to the actuation of a tool, should be interpreted as "in two or more steps which are separated in time."

The term "image stream" should be interpreted to mean the display of at least five image frames at a frame rate such that the image frames in effect show a movie of a portion of a subject's body undergoing at least one entire motion cycle. An image stream of a portion of a subject's body undergoing a motion cycle typically has a frame rate of at least 1 frame per motion cycle. In the case of a cardiac motion cycle, therefore, the image stream typically has a frame rate of at least 0.5 Hz (for a slow heart rate). In the case of cardiac and non-cardiac motion cycles, the frame rate is typically 1-10 frames per motion cycle, or higher.

Identification of Vessel Boundaries and the Generation of a Road Map

Reference is now made to FIG. 1, which is a flow chart, at least some of the steps of which are used to automatically generate a road map, in accordance with some applications of the present invention. The automatic generation of a road map is described with reference to coronary angiography, by way of example. The scope of the present invention includes the automatic generation of a road map using a different imaging modality.

In Phase 1 of the automatic road map generation, a fluoroscopic image stream of the coronary arteries is acquired. Typically, during the acquisition of the image stream, a contrast agent is administered to the subject. Optionally, the image stream is gated, tracked, and/or stabilized by other means. For example, selected image frames corresponding to a given phase in the motion cycle of the heart may be identified by means of a physiological signal. For some applications, the physiological signal applied is the subject's ECG and the image frames are selected by means of gating to the ECG and/or by other means of gating as described in WO 08/107,905 to Iddan, which is incorporated herein by reference. It is noted that stabilization of the image stream is optional and, for some applications, a road map is automatically generated on a native (non-stabilized) fluoroscopic image stream.

For some applications, the ECG signal is received from an ECG monitor. Alternatively or additionally, the ECG signal is received from a Cardiac Rhythm Management (CRM) device such as a pacer, or a defibrillator. For some applications, a processor that performs the automatic generation of the road map, or a dedicated processor, identifies the selected phase of the ECG signal. (In general, in the present application, when references are made to the functionalities of a processor, the functionalities may be performed by a single processor, or by several processors, which act, effectively, like a single processor with several functionalities.) Alternatively, the selected phase (e.g., the R wave of the ECG signal) is identified by the ECG monitor. Further alternatively, the selected phase (e.g., the R wave of the ECG signal) is identified by the CRM device.

For some applications, image tracking is applied to the native image stream, with respect to a guiding catheter or with respect to a segment of the guiding catheter, as described in further detail hereinbelow. For example, the native image stream may be image tracked with respect to the distal tip of the guiding catheter, e.g., a curved portion of the guiding catheter. Alternatively or additional, image tracking is performed with respect to one or more radiopaque (or otherwise visible) markers or segments of a tool. For some applications, image tracking, or alternative techniques for stabilizing the image stream, is performed with respect to a virtual feature or region of image frames of the native image stream. Such virtual features are typically derived from a manipulation (such as an average, a weighted average, a translation, a rotation, and/or a scaling) of the location of one or more observable features of the image. For example, the virtual feature may be the average location of two radiopaque markers of a balloon.

In Phase 2 of the automatic road map generation, a baseline fluoroscopic image frame is identified, typically automatically, the baseline image frame having been acquired prior to the contrast agent having been administered to the subject. (For some applications, the baseline frame is selected manually by the user.) For some applications, the baseline image frame is gated to a given phase of the subject's cardiac cycle (i.e., it selected based on its having been acquired at the given phase of the subject's cardiac cycle). Typically, the baseline image is an image frame that is generated immediately before the contrast agent was (or is about to be) administered to the subject (as described in further detail hereinbelow).

For some applications, the baseline image frame is used a reference image frame, to which to compare subsequent image frames, in order to determine when an angiographic sequence has commenced, as described hereinbelow. Alternatively or additionally, techniques such as the techniques described hereinbelow are used for determining the commencement or the end of an angiographic sequence, not by comparing image frames to the baseline image frame, but by detecting rapid changes in parameters of image frames of the image stream. For example, in order to determine when an angiographic sequence has commenced, a vesselness descriptor may be calculated for each image in the image stream. The vesselness descriptor is typically calculated in accordance with the techniques described hereinbelow. For example, the vesselness descriptor may be calculated by counting a number of possible centerline points of a vessel in each of the images that are located near to possible edge lines of the vessel. Commencement of an angiographic sequence is determined by detecting a rapid increase in the vesselness descriptor. The end of an angiographic sequence is determined by detecting a rapid decrease in the vesselness descriptor.

For some applications, the baseline image frame is analyzed such that the degree of "vesselness" (i.e., the extent to which a given pixel is likely to be an element of an image of a vessel) in applicable areas of the image frame is determined. For example, vesselness may be determined by means of a filter, such as the filter described in the article by Frangi (a "Frangi filter"), cited hereinabove, which is incorporated herein by reference, and/or by means of a filter that performs enhancement and/or detection and/or segmentation of curvilinear structures. For some applications, a filter is used that is similar to a Frangi filter, but that differs from a Frangi filter ("a Frangi-like filter") (a) in that vesselness is a homogeneous function, and/or (b) in the multipliers employed for the normalization of scales.

Figure 2:
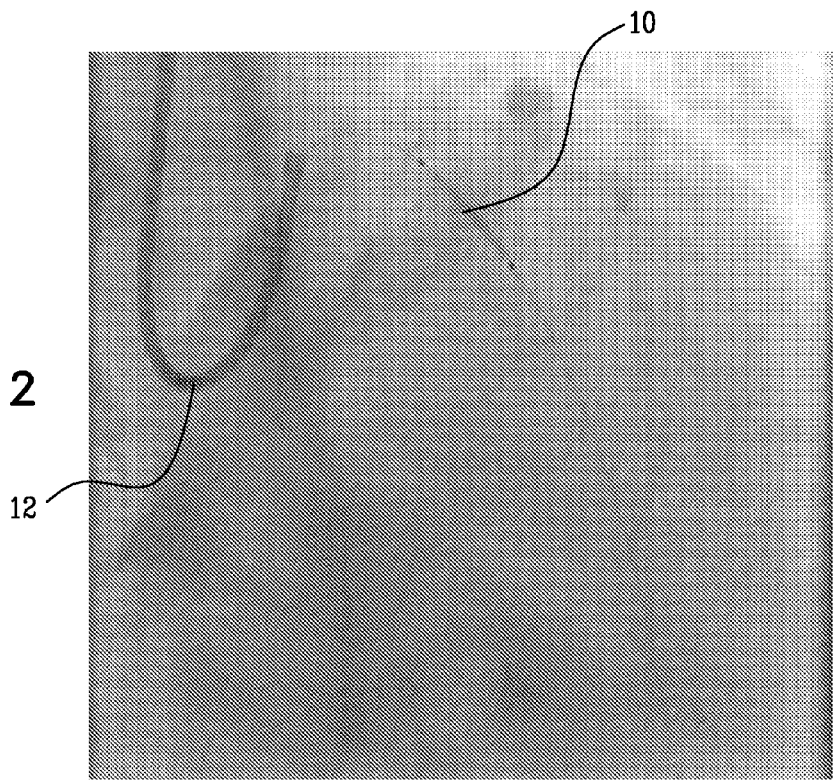
FIG. 2 shows a baseline image that was used in the automatic generation of a road map, in accordance with some applications of the present invention.

Reference is now made to FIG. 2, which shows a baseline image that was used in the automatic generation of a road map, in accordance with some applications of the present invention. A guiding catheter 12, through which a catheter of a non-inflated balloon 10 is inserted, may be observed.

In Phase 3 of the automatic road map generation, an identification or detection is typically provided that angiography has commenced or is about to commence. For example, commencement of the angiography may be detected by detecting the injection of contrast agent, and/or by detecting the activation of a special imaging mode such as cine. For some applications, several angiographic sequences are acquired and the commencement of each of the angiographic sequences is detected, in order to separate the angiographic sequences from one another. Typically, the angiographic sequences are separated from each other such that the most suitable image frame for generating a new road map is selected only from among the frames belonging to the most recent angiographic sequence.

For some applications, the identification that angiography has commenced, or is about to commence, is provided automatically by the apparatus for injecting the contrast agent. Alternatively or additionally, the identification that angiography has commenced, or is about to commence, is provided manually by the operator of the apparatus injecting the contrast agent. Further alternatively or additionally, the identification that angiography has commenced is provided automatically by identifying that in the acquired image frames there is an increased portion or count of vessel-like pixels. For example, such automatic identification may be provided by means of a filter that performs enhancement and/or detection and/or segmentation of curvilinear structures, a Frangi filter, and/or a Frangi-like filter. For some applications, the commencement of an angiographic sequence is detected by detecting the appearance of temporarily-appearing vessel-like features. Typically, the detection of temporarily-appearing vessel-like features indicates a new angiographic sequence.

For some applications, the identification that angiography has commenced is provided automatically by means of image processing, as described in WO 08/107,905 to Iddan, which is incorporated herein by reference. Suitable image processing techniques include the analysis of changes in the current image, and/or, specifically, changes in the image region at the distal end of the catheter from which the contrast agent enters the subject's vasculature (such as a guiding catheter in the case of coronary road mapping). For example, changes in the image may include a relatively abrupt change in the color and/or grayscale level (i.e., darkness) of a relatively large number and/or portion of image pixels, or the appearance of vessel-like features in the image, or any combination thereof. It is noted that by assessing a change in the darkness level to identify the time of injection of the contrast agent, the automatic road map generation processor may identify a darker area of the image or a lighter area of the image, depending on whether the contrast agent is represented as dark or light.

For some applications, the identification that angiography has commenced is performed by comparing a current image frame to the baseline image frame. Alternatively, the identification that angiography has commenced is performed not by comparing image frames to the baseline image frame, but by detecting rapid changes in parameters of image frames of the image stream.

For some applications, the identification that angiography has commenced is accelerated by reducing the resolution of the image frames, and applying image processing techniques to the reduced-resolution image frames.

It is noted that whereas specifically assessing the region at the distal end of the catheter typically enhances signal to noise (because this region is most likely to show an abrupt change), the scope of the present invention includes assessing most or all of the acquired image data to identify the injection of the contrast agent.

Figure 3:
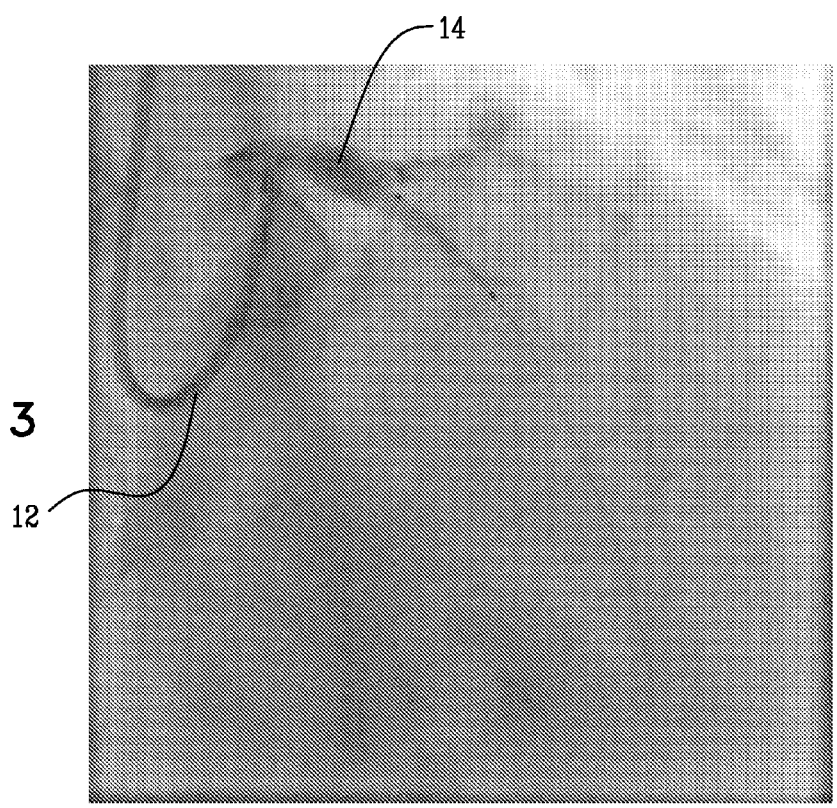
FIG. 3 shows an image frame during the commencement of an angiographic sequence that was used in the automatic generation of a road map, in accordance with some applications of the present invention.

Reference is now made to FIG. 3, which shows an image frame during the commencement of an angiographic sequence that was used in the automatic generation of a road map, in accordance with some applications of the present invention. A cloud 14 of contrast agent may be observed in the vicinity of the distal tip of guiding catheter 12.

In Phase 4 of the automatic road map generation, an identification or detection is typically provided that the acquisition of image frames in the presence of contrast agent has ended or subsided. That is to say, the contrast agent injected into the coronary arteries has dissipated (or mostly dissipated) such that it is generally no longer visible in the fluoroscopic images. For some applications, such identification is provided automatically by apparatus that injects the contrast agent, and/or is provided manually by the operator of the apparatus injecting the contrast agent. For some applications, such identification or detection is provided by identifying decreased vesselness, for example, by means of a filter that performs enhancement and/or detection and/or segmentation of curvilinear structures, a Frangi filter, and/or a Frangi-like filter. Alternatively or additionally, such identification or detection is provided automatically by image processing techniques similar to those described with reference to Phase 3 above.

For some applications, and as an alternative to Phase 4, the end of a sequence of angiographic images is assumed after a certain period of time has elapsed since the commencement of the angiographic sequence. The period of time typically corresponds to the typical duration of an angiographic sequence.

In Phase 5 of the automatic generation of the road map, the angiographic image frames (also known as angiograms) corresponding to a given angiographic sequence are automatically analyzed, such that an angiogram is derived (e.g., selected) from the set of angiograms, based upon visibility of at least a portion of the blood vessels in the angiograms. For some applications, the angiogram with the greatest visibility of coronary arteries is selected, with such selection typically being automatic. The greatest visibility is typically determined based upon the greatest total number of arteries observed, the greatest number of image pixels attributed to an artery, and/or the greatest image contrast in the appearance of specific arteries. Such an angiogram with the greatest visibility of coronary arteries is typically the most suitable for serving as the basis for the most informative road map in situations wherein the greatest amount of vasculature should be observed.

For some applications, an aggregated image of two or more angiograms is derived from the sequence of angiograms. For example, two or more angiograms that provide the greatest visibility of the coronary arteries are added to each other. Alternatively, a portion of a first angiogram that provides good visibility of a first portion of the coronary arteries is aggregated with a portion of a second angiogram that provides good visibility of a second portion of the coronary arteries.

For some applications, an angiogram having the greatest visibility of the coronary arteries is identified by means of vesselness of image pixels. Alternatively or additionally, such vesselness is determined by means of a filter, such as a filter that performs enhancement and/or detection and/or segmentation of curvilinear structures, a Frangi filter, and/or a Frangi-like filter. For some applications, the determination of vesselness of image pixels is made with reference to known anatomical structures, and/or with reference to known anatomy of the specific subject. For some applications, the determination of vesselness of image pixels is made while accounting for the specific viewing angle at which the images are generated.

For some applications, only angiograms belonging to the angiographic sequence that are gated to a given phase of the cardiac cycle are analyzed. An angiographic image frame is derived (e.g., selected) from the gated angiograms, based upon visibility of at least a portion of the blood vessels in the angiograms. For example, the gated angiogram with the greatest visibility of coronary arteries may be selected. For some applications, the given cardiac phase is an end-diastolic phase, at which certain coronary vessels are typically the most spread apart.

For some applications, the end-diastolic phase is identified by means of image processing (and not, or not exclusively, by means of gating to the ECG signal). For example, an image in which distances between coronary vessels are largest may be identified, and/or a degree of vesselness within a region of interest may be analyzed. For some applications, an image frame in which motion of coronary blood vessels is at a minimum, as would typically be expected during end-diastole, is identified.

For some applications, limiting the derivation of the angiogram to only among angiograms gated to a specific cardiac phase is suitable when the operator's interest is focused on the specific phase. Typically, for such applications, the operator will designate the phase with respect to which the angiograms are gated via an input device. For some applications, only angiograms sampled at a defined time interval (e.g., every 100 ms, or between the 700th ms and 1000th ms of every second), and/or at a defined sequential interval (e.g., every fifth frame, or between the 10th and 15th of every 15 frames), are analyzed. For some applications, frames sampled within the time interval are gated, and/or frame(s) with the highest vesselness are identified from among frames sampled within the time interval.

Figure 4:
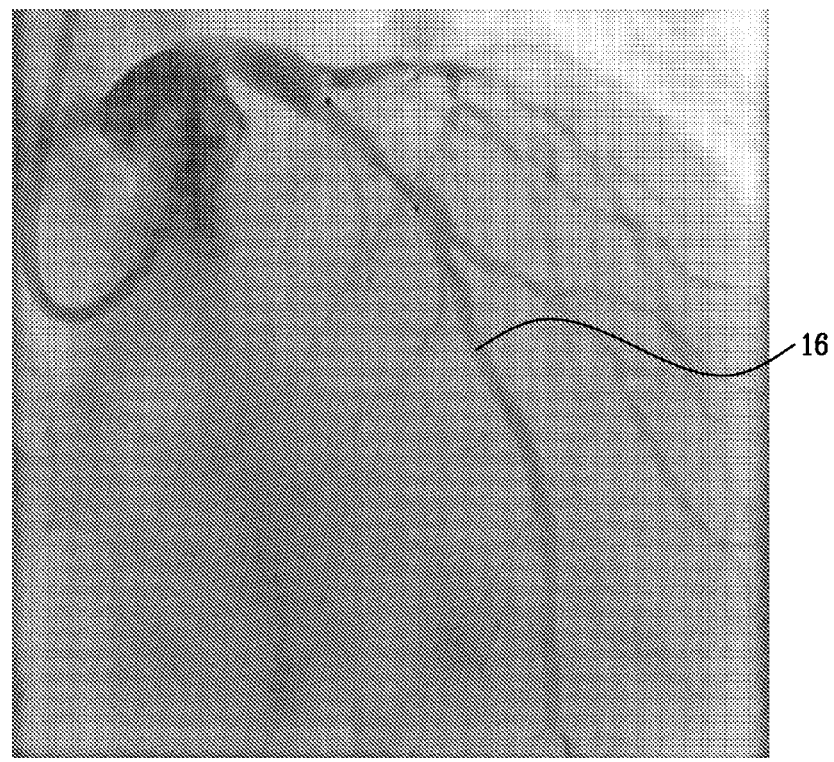
FIG. 4 shows an angiographic image (i.e., an angiogram) that was derived from a set of angiograms, some blood vessels appearing highlighted in the image, in accordance with some applications of the present invention.

Reference is now made to FIG. 4, which shows an angiographic image (i.e., an angiogram) that was derived from a set of angiograms, some blood vessels 16 appearing highlighted (i.e., demonstrated) in the image, in accordance with some applications of the present invention.

In Phase 6 of the automatic road map generation, designated vessels in the selected angiogram(s) are enhanced, typically automatically. For some applications, low-contrast vessels that are typically less observable in the non-enhanced image, and/or narrow vessels that are typically less observable in the non-enhanced image, are detected and enhanced. For some applications, non-vascular structures whose spatial and/or temporal characteristics differ from those of vascular structures are identified, and the visibility of such structures is reduced. For example, such spatial characteristics may include dimensions, relative location, gray level, texture, edge smoothness, or any combination thereof, and such temporal characteristics may include relative motion, absolute motion, and/or a change over time of any of any of the aforementioned spatial characteristics. For some applications, the enhancement is performed by means of a filter that detects and/or segments curvilinear structures. Alternatively or additionally, the enhancement is performed by means of a Frangi-filter, such that vessels and their local orientation are automatically detected by analyzing eigenvalues and eigenvectors of the Hessian matrix of a smoothed image.

In Phase 7 of the automatic road map generation, the darkest lines, or the center lines, or any other characterizing or representative lines corresponding to paths of one or more designated blood vessels are determined, typically automatically. For some applications, the points comprising such lines are determined by means of their relatively high value of vesselness. Alternatively or additionally, the points comprising such lines are determined by the extent to which their gradient is orthogonal to the eigenvector of the Hessian matrix corresponding to the highest eigenvalue. For some applications, such determination is assisted by a voting function applied to points that are adjacent to those points that are eventually determined to constitute the center line itself.

For some applications, thresholding is applied to image pixels by means of hysteresis. For example, pixels the vesselness value of which falls below the high threshold of the hysteresis, but yet above the low threshold of the hysteresis, are incorporated into a line if they are contiguous with pixels that fall at or above the high threshold of the hysteresis.

For some applications, the points which form the aforementioned lines are determined by means of morphological operations. For example, such morphological operations may include the skeletonization of a thresholded vesselness image. For some applications, the threshold applied is adaptive according to the specific region in the image.

Figure 5:
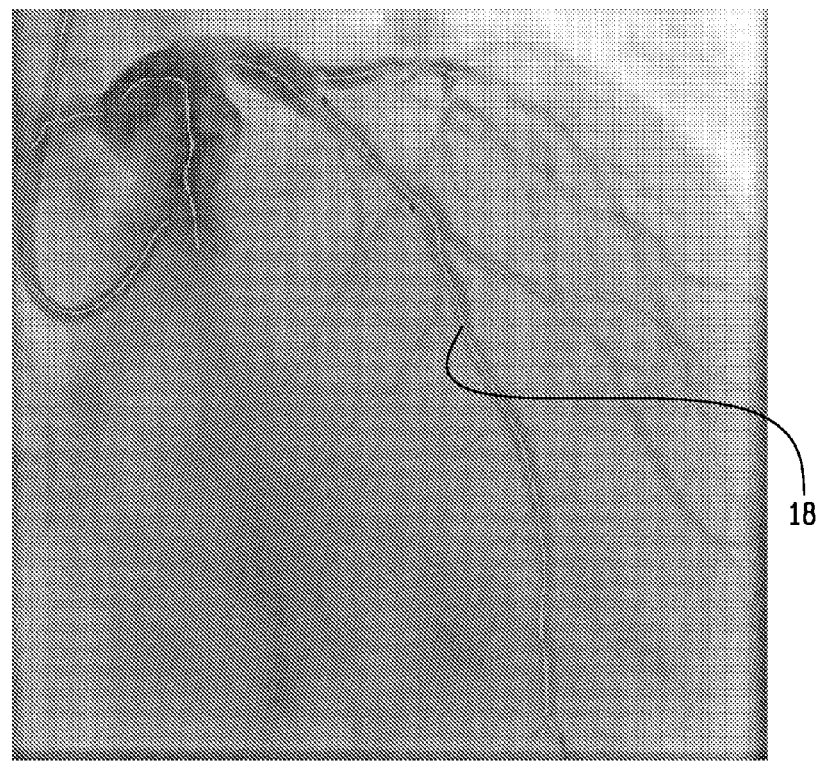
FIG. 5 shows center lines constructed automatically along a portion of the blood vessels, in accordance with some applications of the present invention.

Reference is now made to FIG. 5, which shows center lines 18 constructed automatically along a portion of the blood vessels, in accordance with some applications of the present invention. The center lines are shown overlaid upon the angiogram from which they were constructed.

Figure 6:
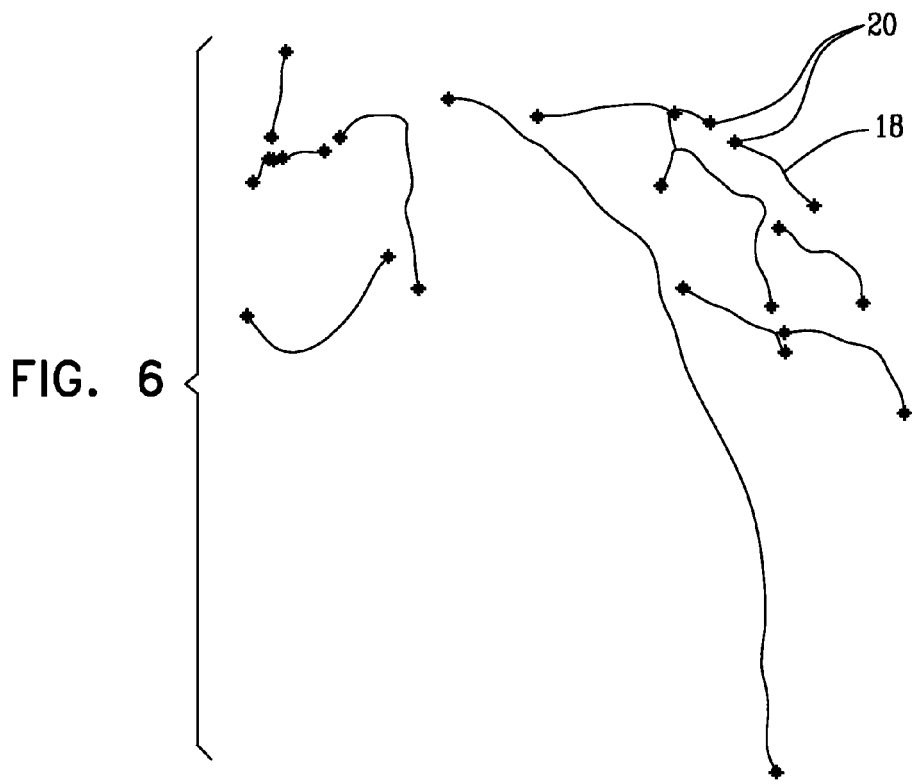
FIG. 6 shows end points at discontinuities in the center lines that were identified automatically, in accordance with some applications of the present invention.

Reference is now made to FIG. 6, which shows end points 20 (shown as stars) at discontinuities in center lines 18 that were identified automatically, in accordance with some applications of the present invention. In Phase 8 of the automatic road map generation, which is applicable in cases in which there are discontinuities within a center line (or any other characterizing or representative line) of a designated vessel, such discontinuities are bridged, typically automatically. For some applications, end points are identified automatically at both sides of a discontinuity. For some applications, bridging is performed across gaps between end points by means of a shortest-path algorithm, for example the shortest-path algorithm described in the article by Dijkstra, which is cited hereinabove, and which is incorporated herein by reference. For some applications, bridging is performed subsequent to the detection of edges (i.e., boundaries), corresponding to each already-determined segment of the center lines, i.e., subsequent to Phase 9 of the automatic road map generation, described hereinbelow.

For some applications, bridging is performed across gaps between end points by means of an algorithm that takes into account the directional vectors of the lines at both sides of the discontinuity. Alternatively or additionally, the bridging is performed with reference to known typical structures of the coronary tree. For example, bridging may be performed based upon what is typical at the corresponding section of a coronary tree.

For some applications, the bridging of gaps is performed with reference to known structures of the coronary tree of the particular subject who is being imaged. Typically, in such cases, gaps are bridged based upon what has been previously observed, by means of imaging a corresponding section of the subject's coronary tree. In accordance with respective applications, the imaging modality used to image the corresponding section of the subject's coronary tree is the same as the modality that is used to generate the angiograms, or is a different imaging modality (for example, pre-operative CT) from the imaging modality used to generate the angiograms (for example, fluoroscopy).

For some applications, the bridging of gaps is made while accounting for the specific viewing angle at which the images are generated.

Figure 7:
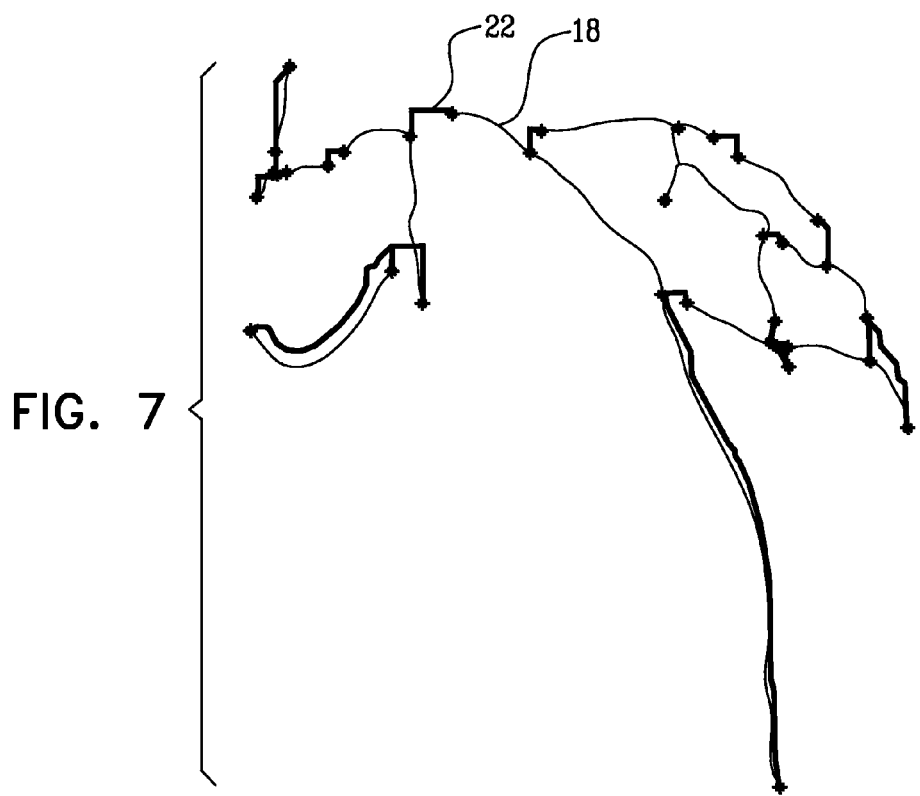
FIG. 7 shows gaps between end points in the center lines having been bridged automatically, in accordance with some applications of the present invention.

Reference is now made to FIG. 7, which shows bridges 22 in gaps between end points in center lines 18, the bridges having been generated automatically, in accordance with some applications of the present invention.

In Phase 9 of the automatic road map generation, the boundaries (i.e., edges or edge lines) of one or more designated vessels are determined, typically automatically. For some applications, such boundaries are determined by means of region-based adaptive thresholding of the vesselness image. Alternatively or additionally, such boundaries are determined by means of a region-growing algorithm. Further alternatively or additionally, such boundaries are determined by means of an edge detector, and/or by means of a morphological operation. For some applications, such boundaries are determined by means of a watershed technique, which splits an image into areas, based on the topology of the image. Alternatively or additionally, such boundaries are determined by means of a live contour, and/or by means of matching filters.

For some applications, the determination of boundaries is made with reference to known typical structures of the coronary tree. Typically, in such cases, boundaries are determined in certain vessel segments based upon what is typical at the corresponding section of a coronary tree.

For some applications, the determination of boundaries is made with reference to structures of the coronary tree of the specific subject. Typically, boundaries are generated based upon what has been previously observed, by means of imaging a corresponding section of the subject's coronary tree. In accordance with respective applications, the imaging modality used to image the corresponding section of the subject's coronary tree is the same as the modality that is used to generate the angiograms, or is a different imaging modality (for example, pre-operative CT) from the modality used to generate the angiograms (for example, fluoroscopy).

For some applications, the boundaries are determined by means of a dynamic programming approach, optimizing a penalty function. For example, the penalty function may be based upon image derivatives along directions perpendicular to the center line, and/or the distance from the center line.

For some applications, center lines are determined for the vessels identified in most of, or the entire, image frame, while boundaries are only determined for specific vessels or sections of vessels. For example, boundaries of specific vessels may be determined upon the user indicating, typically by means of an input device, a region of interest or a specific vessel of interest or a specific section of such vessel.

For some applications, the determination of boundaries is made while accounting for the specific viewing angle at which the images are generated.

Figure 8:
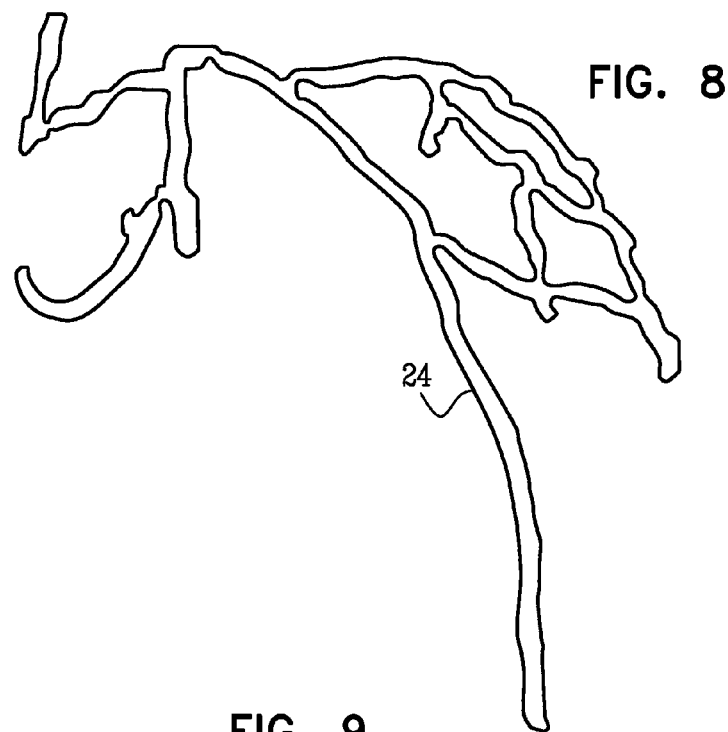
FIG. 8 shows edge-lines (i.e., boundaries) of the blood vessels, which were detected automatically, in accordance with some applications of the present invention.

Reference is now made to FIG. 8, which shows edge-lines 24 (i.e., boundaries) of blood vessels, which were detected automatically, in accordance with some applications of the present invention.

For some applications, the system automatically validates a point/segment as being part of the center line, and points/segments as being part of edge lines at sides of the center line, by cross-referencing the center line points/segments and edge line points/segments with respect to each other. For example, at each side of a potential center line, an edge the gradient of which is perpendicular, or almost perpendicular, to that of the center line is selected such that the two gradients are in opposite directions and leading away from the center line. Typically, such validation is used for the elimination of inappropriate center lines (or pixels attributed to such lines) and/or edge lines (or pixels attributed to such lines) and for the selection of those that are most appropriate.

For some applications, and typically subsequently to the aforementioned validation of matching between center lines and edge lines, missing points/sections in center lines are deduced and added. For some applications, vectors obtained from a Frangi-like filter are applied from known points at both sides of a gap in a center line and into the gap. Such vectors are local and typically are applied incrementally with each increment based upon a new local computation, until the gap is typically eliminated.

For some applications, and typically subsequently to the aforementioned validation of matching between center lines and edge lines, missing points/sections in edge lines are deduced and added. For some applications, sets of edge points are selected at both sides of a gap. A dynamic programming approach, optimizing a penalty function, is then applied to fill in the gap by proposing additional edge points, the distances from the center line of which edge points are typically similar to those of the adjacent, already-known edge points. The process is typically applied continuously until the gap in the edge line is bridged.

For some applications, the road map includes an image or contour of a tool that was situated within one of the blood vessels at the time of the angiogram. Alternatively or additionally, the road map includes markers, and/or a graphical representation of markers, of a tool that was situated, at the time of the angiogram, within one of the blood vessels. For example, the road map may include, in addition to the boundaries of the vessel, small circles indicating the positions of the markers of a coronary balloon while such balloon was situated within the vessel at the time the angiogram was taken.

Figure 9:
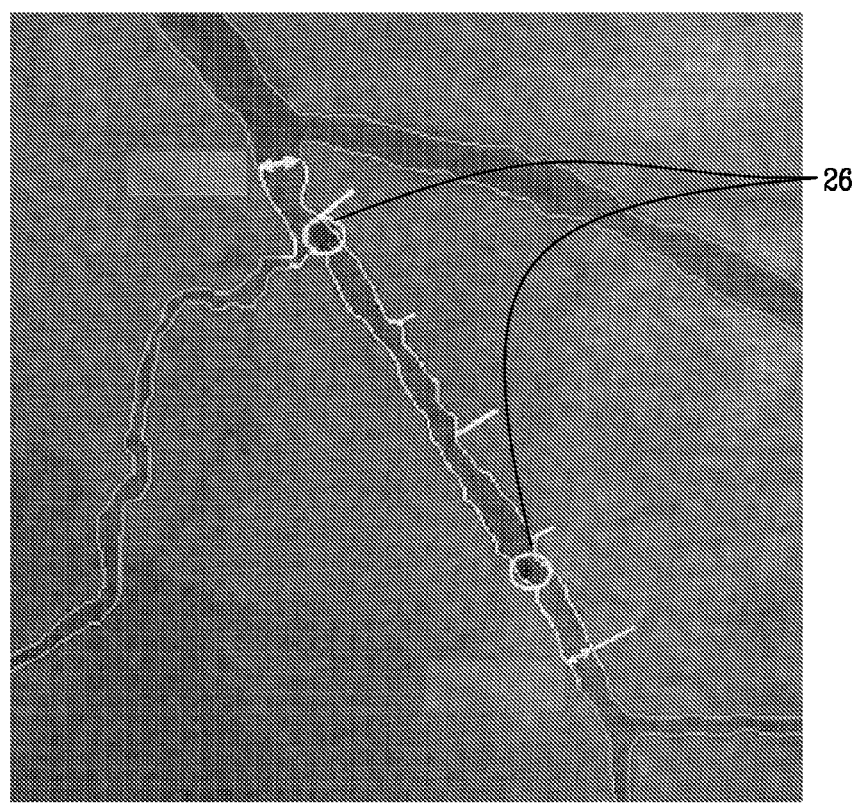
FIG. 9 shows a road map in which the markers of a balloon situated within an artery are visible, in accordance with some applications of the present invention.

Reference is now made to FIG. 9, which shows a road map in which markers 26 of a balloon situated within an artery are visible, in accordance with some applications of the present invention.

For some applications, generation of the road map is intra-procedural. For example, the road map may be automatically generated in real time, or in near real time relative to the end of the angiographic segment. Alternatively, the automatic generation of the road map is post-procedural.

It is noted that, for some applications, not all of the steps shown in FIG. 1 are performed for the automatic generation of the road map.

Generation of Distance Indicators

Figure 10:
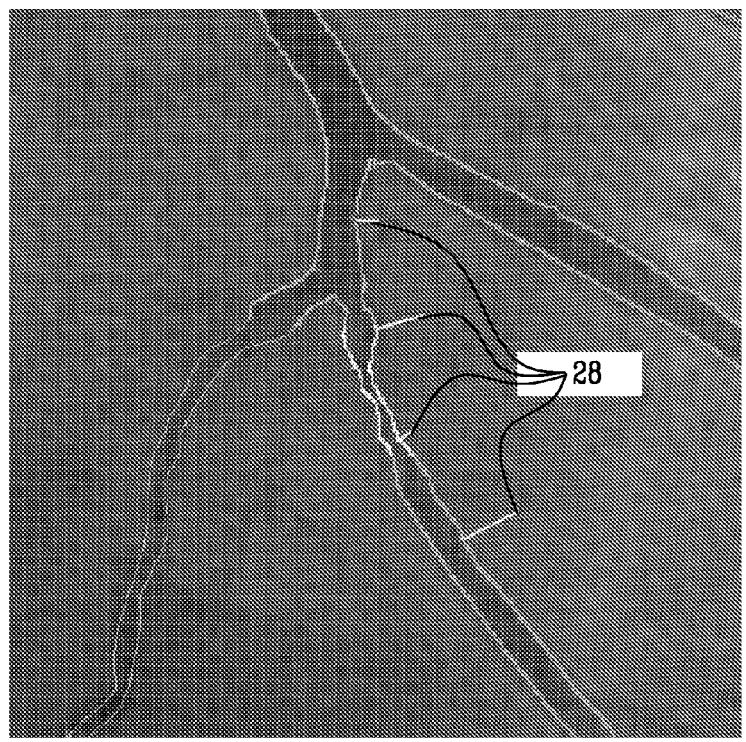
FIG. 10 shows distance indicators on a road map, in accordance with some applications of the present invention.

Reference is now made to FIG. 10, which shows distance indicators 28 on a road map, in accordance with some applications of the present invention. For some applications, a road map is generated that includes distance indicators (e.g., notches) placed along or across a designated vessel or a section thereof. For example, the indicators may be placed in order to show the length or the diameter of the vessel or section thereof. For some applications, the distance indicators are generated automatically.

For some applications, distance indicators are longitudinal, and are placed along a borderline, and/or along a center line (or any other characterizing or representative line) of a designated vessel. For some applications, segments of a designated vessel are marked in different colors corresponding to distances.

For some applications, the distances between the distance indicators are known. For example, the distances between the indicators may be determined based upon some known anatomical feature, or based upon a known dimension of another element that is, or has been, present in the image stream. For example, the known dimension may be the distance between radiopaque (or otherwise visible) markers or segments of a tool. For some applications, the tool is a balloon, a marker wire, a stent, an endoluminal measurement catheter (such as an FFR catheter), and/or an endoluminal imaging catheter (such as an MRI, OCT, IVUS, NIRS, and/or an ultrasound catheter).

For some applications, the known dimension is the length of an already-deployed stent, and/or the length of a radiopaque (or otherwise visible) segment of a tool (e.g., a guide wire). Alternatively or additionally, the known dimension is the diameter of a tool, such as a guiding catheter. For some applications, the diameter of the guiding catheter is indicated by the user. Alternatively or additionally, the diameter of the guiding catheter is a default value set in the system or otherwise determined by the system.

For some applications, the guiding catheter is indicated by the user, via an input device (e.g., by pointing to the catheter using the input device). Alternatively or additionally, the guiding catheter is identified automatically by the system, by means of image processing. For some applications, the user indicates the image region in which the guiding catheter is located, and then the guiding catheter is detected automatically. For example, the user may indicate (using an input device) a point anywhere in the region of the guiding catheter, and then the guiding catheter is detected automatically. Or, the user may indicate a point on the guiding catheter itself for its identification.

Figure 11:
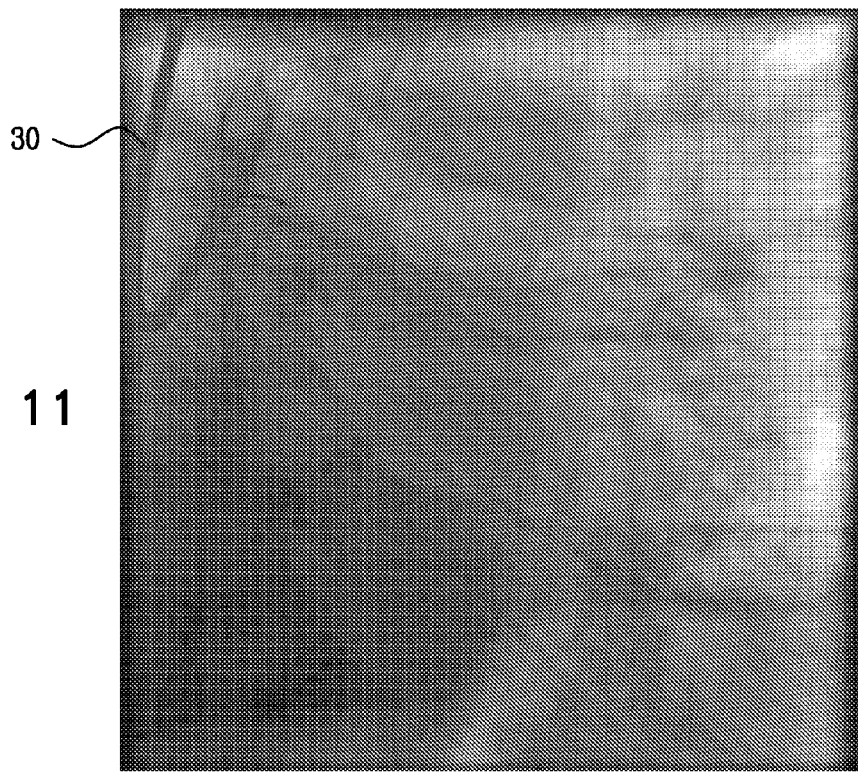
FIG. 11 shows an image in which a guiding catheter has been segmented, in accordance with some applications of the present invention.

Reference is now made to FIG. 11, which shows a fluoroscopic image in which a guiding catheter 30 has been segmented, in accordance with some applications of the present invention. For some applications, after the guiding catheter is detected, it is segmented automatically so that the portion of its lumen that is within the image frame is highlighted. (Although the image in FIG. 11 is black-and-white, typically the segmented catheter is highlighted in color.) For some applications, the guiding catheter is automatically detected and/or segmented using techniques similar to those described hereinabove for the automatic identification of vessels.

For some applications, distance indicators are placed, in the form of a grid, in the entire image frame, in a region of interest within the image frame, and/or in a segment of a vessel within the image frame.

For some applications, distance indicators are placed, in the form of concentric circles, in the entire image frame, in a region of interest within the image frame, and/or in a segment of a vessel within the image frame. For some applications, distance indicators are placed in the form of concentric circles, the center of which circles is at the current location of a cursor positioned by the user, or a location otherwise indicated by the user.

For some applications, the distance indicators are used for measurements, for example, quantitative vessel analysis (QVA) measurements, as described hereinbelow.

Displaying the Road Map and the Fluoroscopic Image Stream

For some applications, a road map (e.g., an automatically generated road map, as described hereinabove) is displayed in combination or conjunction with a stabilized image stream, for example, as described in WO 08/107,905 to Iddan, which is incorporated herein by reference. For example, the road map may be overlaid upon a stabilized or non-stabilized image stream, typically automatically. For some applications, the road map is overlaid on a current image stream in real time, or in near real time. Alternatively or additionally, the road map is overlaid on an image stream, in reloop mode (i.e., a mode in which an image stream, which is typically a recent sequence, is replayed in a loop). For example, the road map may be overlaid on a fluoroscopic image stream from which the road map was derived, while the fluoroscopic image stream is being replayed in a loop.

Figure 12:
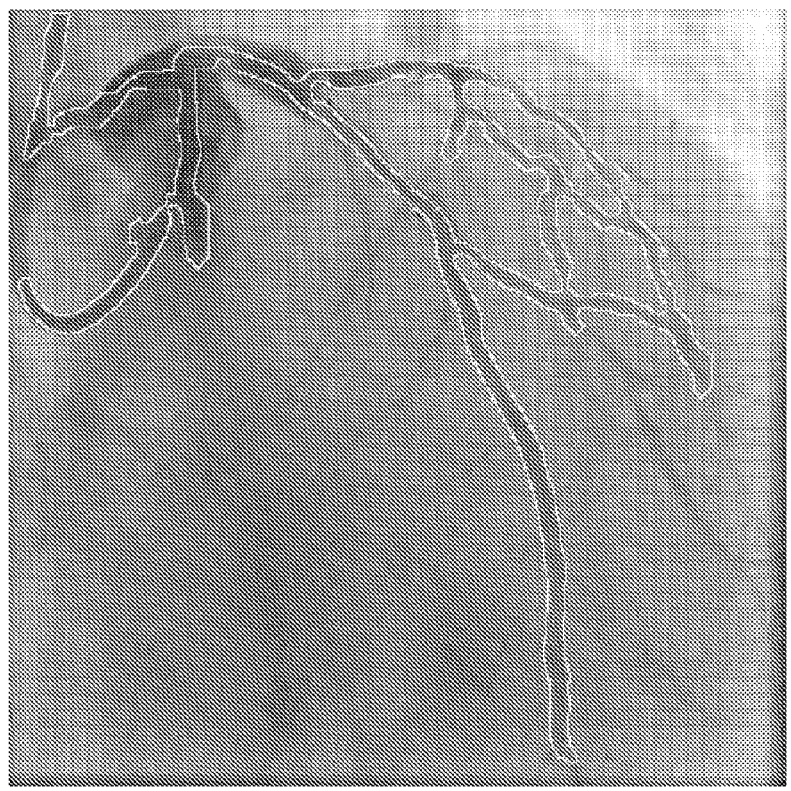
FIG. 12 shows an automatically-generated road map, overlaid upon the angiogram from which it was generated, in accordance with some applications of the present invention.

Reference is now made to FIG. 12, which shows an automatically-generated road map, overlaid upon the angiogram from which it was generated, in accordance with some applications of the present invention. For some applications, overlaying of the road map on the angiogram from which it was created is used to evaluate the accuracy and/or completeness of the road map. As shown, the road map is typically marked as a set of thin boundary lines (although the road map may be marked in a different manner).

Figure 13:
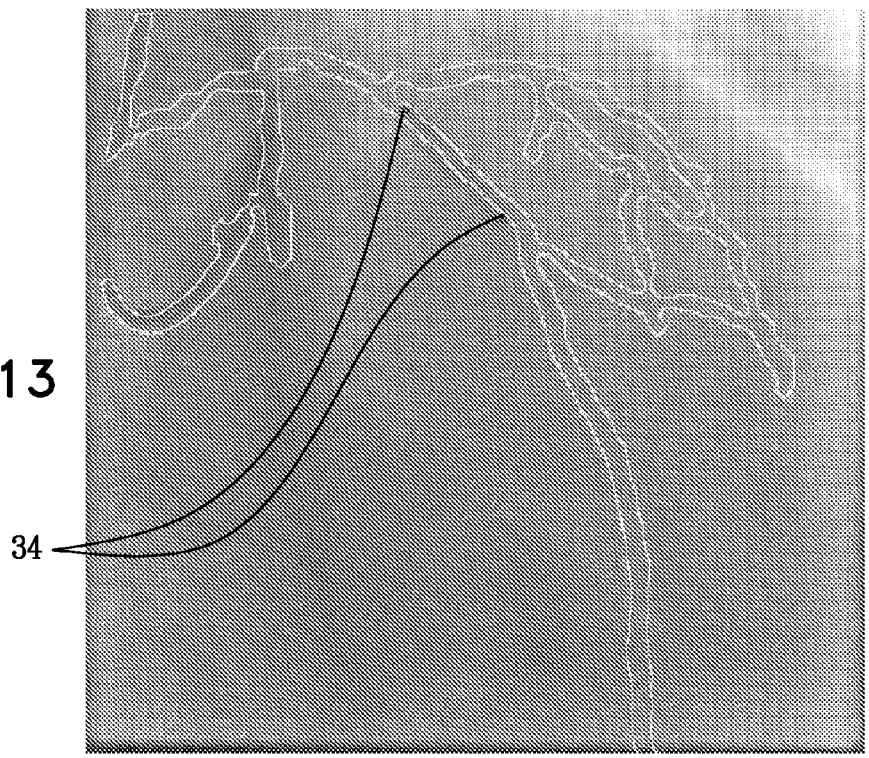
FIG. 13 shows an automatically-generated road map, overlaid upon an image frame belonging to a stabilized image stream, in accordance with some applications of the present invention.

Reference is now made to FIG. 13, which shows an automatically-generated road map, overlaid upon an image frame belonging to a stabilized image stream, in accordance with some applications of the present invention. As shown in FIG. 13, for some applications, the road map is overlaid upon a fluoroscopic image frame that is not an angiogram (that is, the road map is overlaid on an image frame that was generated in the absence of a contrast agent). As shown, the road map is marked as a lighter-colored boundary line (although the road map may be marked in a different manner). Thus, the layout of the vasculature is depicted even though the vasculature itself is invisible in the underlying fluoroscopic image. An inflated coronary balloon can be identified in the fluoroscopic image by its two dark markers 34. Thus, the location of the balloon within the road map is determined.

For some applications, using the techniques described herein facilitates further identification of the location of the balloon vis-à-vis the vessel in which it is placed, without requiring additional angiograms. Additional angiograms may necessitate irradiation of subject and/or staff, and/or the additional injection of a potentially-damaging contrast agent. Thus, by displaying the road map on top of the fluoroscopic image, irradiation of those involved in the procedure and the total dosage of contrast agent administered to the subject may be reduced. Alternatively or additionally, there are other advantages to displaying the road map on top of the fluoroscopic image.

Figure 14:
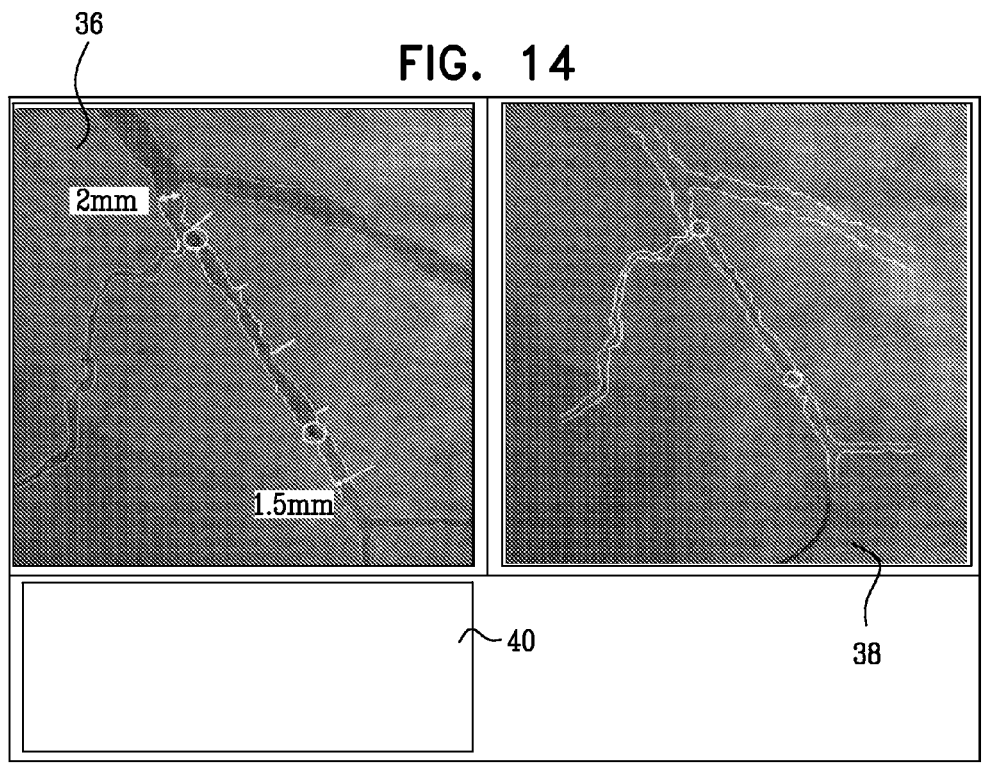
FIG. 14 shows a road map displayed side-by-side with a stabilized fluoroscopic image stream, edge lines of the roadmap also being overlaid upon the fluoroscopic image stream, in accordance with some applications of the present invention.

Reference is now made to FIG. 14, which shows a road map 36 displayed side-by-side with a stabilized fluoroscopic image stream 38, edge lines of the road-map also being overlaid upon the fluoroscopic image stream, in accordance with some applications of the present invention. For some applications, the road map is displayed side-by-side with the fluoroscopic image stream. In accordance with respective applications, the fluoroscopic image stream that is displayed next to the road map is the native stream, a gated stream, an image tracked stream, and/or an image stream that is both gated and image tracked. For some applications, a quantitative-vessel-analysis box 40 is displayed on the screen. Quantitative vessel analysis measurements and/or diagrams are displayed in box 40 as described hereinbelow.

For some applications, image tracking of the fluoroscopic image stream is performed with respect to the guiding catheter or with respect to a segment thereof, as described hereinbelow. Alternatively or additionally, image tracking is performed with respect to radiopaque markers or segments of a tool (e.g., a balloon, a stent, a valve, or a different tool), as described hereinbelow.

For some applications, the road map is generally displayed side-by-side with the fluoroscopic image stream, and from time to time is momentarily overlaid upon the fluoroscopic image stream. In accordance with respective applications, the fluoroscopic image stream is native, gated, image tracked, and/or stabilized. For some applications, such overlaying is preceded by registration of the road map to fluoroscopic images. Typically, the road map is registered automatically, on-line, to the fluoroscopic images. Further typically, fiducials are identified within the road map and within the fluoroscopic image stream, in order to facilitate the registration of the road map to the fluoroscopic image stream. Fiducials are typically chosen that are observable even in images of the fluoroscopic image stream that are generated in the absence of a contrast agent. For example, the registration may be performed by means of a portion(s) (e.g., a marker, or a radiopaque portion) of a tool that is observable both in the road map and in the fluoroscopic images. For some applications, a road map corresponding to a given phase of the subject's cardiac cycle is generated, and is overlaid on a fluoroscopic image stream that is gated with respect to the same phase.

Figure 15:
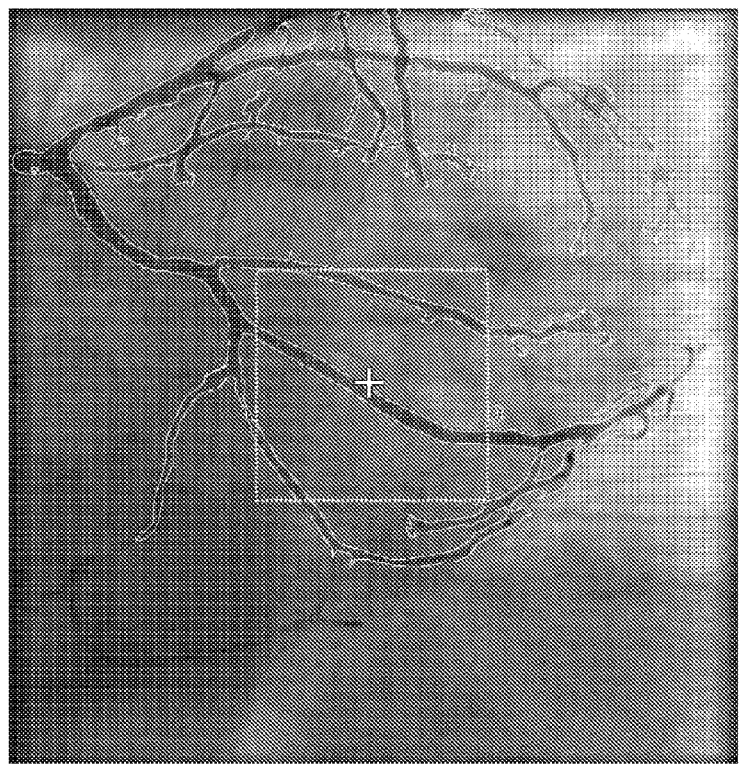
FIG. 15 shows a region of interest marked on a road map, in accordance with some applications of the present invention.

Reference is now made to FIG. 15 which shows a road map on which a region of interest (ROI) has been marked. For some applications, the road map that is displayed corresponds to a specific region of interest (ROI) within the angiogram(s) from which it was generated. For some applications, the ROI is automatically set to be the central region of the angiogram. Alternatively or additionally, the ROI is indicated by the user, such as by marking, using an input device, the center of the ROI, or a window encompassing the ROI. Further alternatively or additionally, the ROI is at first set automatically by the system and then modified by the user. For some applications, the size of the ROI that is displayed is pre-defined. For some applications, the zoom factor at which an image in the ROI is displayed may be changed by the user. In accordance with respective applications, the zoom factor at which a road map in the ROI is displayed is pre-defined, or may be changed by the user.

For some applications, the road map is toggled between the full view (i.e., on the entire angiogram(s) from which it was generated) and the zoom-in view (i.e., only the ROI). Alternatively or additionally, the road map switches automatically from the full view to the zoom-in view once a tool, such as a balloon, is identified by the system to have entered the ROI in a corresponding fluoroscopic image. For some applications, the balloon is identified as having entered the ROI based upon the presence of a radiopaque (or otherwise visible) marker(s) or segment, or some other identifiable portion, of the tool within the ROI. Similarly, for some applications, the road map switches automatically from the zoom-in view back to the full view once the aforementioned tool is identified by the system to have exited the ROI in a corresponding fluoroscopic image. For some applications, such switching, in either direction, is performed by the user. For some applications, the techniques described in the present paragraph are applied to the display of the fluoroscopic image stream.

For some applications, leafing (i.e., browsing) back and forth among multiple angiograms is enabled. Typically, leafing is performed among different images belonging to the same angiographic sequence. For example, the user may wish to observe the gradual spread of contrast agent along multiple angiograms belonging to the same angiographic sequence.

For some applications, leafing is performed among selected angiograms belonging to different angiographic sequences. For example, when determining the placement of a stent by means of an angiogram prior to its deployment, the user may wish to observe an angiogram belonging to a prior sequence in which balloon pre-dilatation was performed at the same lesion in order to ensure that the stent is placed at substantially the same location as the location at which pre-dilatation had been performed.

For some applications, the road map being displayed in conjunction with the fluoroscopic image stream comprises an image of the contrast agent itself, for example, as described in WO 08/107,905 to Iddan, which is incorporated herein by reference. For some applications, the road map comprises a synthesized background(s), enhancement(s), contour(s), pattern(s), texture(s), shade(s) and/or color(s) that was created based upon the visual information acquired from the injection and/or dissipation of contrast agent, using computer graphics and/or image processing techniques. Alternatively or additionally, the gray level of the road map is inversed, such that the road map appears light against a darkened background.

For some applications, the summation or combination of two road maps generated at different times in the procedure is displayed, for example, as described in WO 08/107,905 to Iddan, which is incorporated herein by reference. Typically, a road map generated during a given phase of a first cardiac cycle is summed with a road map generated during a same phase of a second (typically immediately subsequent) cardiac cycle, to create a combined road map that displays more coronary vessels and/or displays coronary vessels with greater clarity. For some applications, such as in the case of a total or partial occlusion in a coronary vessel, the combined road map may comprise the summation or combination of a road map created from an injection of a contrast agent proximally to the occlusion, and a second road map created from an injection of a contrast agent distally to the occlusion, such as via a collateral vessel and/or in a retrograde direction. For some applications, such road maps, which are based on the proximally- and distally-injected contrast agent, are created in the same phase of one or more cardiac cycles, which are not necessarily adjacent cardiac cycles.

For some applications, a three-dimensional road map is constructed by combining two or more two-dimensional road maps recorded from viewing angles that are typically different by 30 degrees or more, for example, as described in WO 08/107,905 to Iddan, which is incorporated herein by reference. For some applications, the two two-dimensional road maps (from which a three-dimensional road map is constructed) are recorded concurrently from two different viewing angles, such as by means of a bi-plane fluoroscopy system. Alternatively or additionally, a three-dimensional road map is created from CT angiography images, typically pre-procedural ones, and then correlated with the real time two-dimensional road map created from intra-procedural angiography. Further alternatively or additionally, a three-dimensional road map is constructed from two or more different images taken from the same viewing angle but during different phases in the cardiac cycle.

For some applications, the images displayed in conjunction with the road map and the stabilized image stream also comprise medical tools or probes. For example, images (or contours) of such tools may be overlaid or projected upon or within the road map. Alternatively or additionally, the markers or radiopaque segments of such tools (or graphical indications of such markers or segments) are overlaid or projected upon or within the road map. For some applications, the segment of the road map that is generally closer or closest to a designated tool is highlighted or indicated in some graphical manner.

For some applications, the road map is corrected, typically automatically, with respect to a designated vessel, based upon the layout of a tool situated in that vessel. For example, the road map may be corrected, typically automatically, with respect to a designated vessel, based upon the detected location of markers or radiopaque segments of a tool situated in that vessel. For some applications, if the tools (or markers or radiopaque segments thereof) are detected to be outside of the road map, then the road map is redrawn or reshaped so that such tools (or markers or radiopaque segments thereof) consequently appear to be within the road map.

For some applications, the medical tools or probes displayed in conjunction with the road map are activated or deployed in synchronization with a specific phase of a physiological signal or process, for example, as described in WO 08/107,905 to Iddan, which is incorporated herein by reference. For some applications, the road map is displayed in conjunction with an image stream that is stabilized with respect to that same phase.

For some applications, and in the case of images pertaining to a cyclically-moving organ, different road maps are displayed, typically in a cyclical manner, in conjunction with the then-current phase of the organ's motion cycle. For example, a dynamic road map as described may be correlated to the cardiac cycle, and/or the respiratory cycle.

Performing Measurements

For some applications, measurements are performed, typically automatically, based upon the determined boundaries of given vessels. For example, measurements may be performed based upon boundaries generated by means of the boundary generation techniques described hereinabove for most or all vessels within an image. Or, measurements may be performed on a specific vessel or segment of a vessel, the boundaries of which have been generated in accordance with the techniques described hereinabove.

Such measurements typically include lesion dimensions, reference artery dimensions, and quantitative vessel analysis (QVA), for estimating the extent of occlusion at a designated lesion. (QVA as used herein refers to the performance of the measurement techniques associated with a technique that is known as quantitative coronary angiography (QCA), but includes performing the measurement techniques (a) on any blood vessel of the subject, and not, specifically, a coronary artery, and (b) on any image of the blood vessel, and not, specifically, on an image of the blood vessel acquired using contrast agent. When performed with respect to coronary arteries, QVA is generally similar to QCA.)

For some applications, performing QVA using the techniques described herein facilitates the performance of measurements without requiring a manual process of constructing the center line and deriving the vessel edges. Typically, QVA is performed automatically or almost automatically, necessitating little to no user intervention or interaction, by using the aforementioned techniques described hereinabove for the automatic generation of center lines and edge lines.

For some applications, center lines and edge lines are validated by cross-referencing the lines, as described hereinabove. Subsequently, missing points/sections in edge lines are deduced and added, as described hereinabove, to support the aforementioned automatic or nearly automatic QVA. For example, sets of edge points may be selected at both sides of the gap, and a dynamic programming approach, optimizing a penalty function, is then applied to fill in the gap by proposing additional edge points whose distances from the center line are typically similar to those of the adjacent, already-known edge points. The process is typically applied continuously until the gap in the edge line is bridged.

Figure 16:
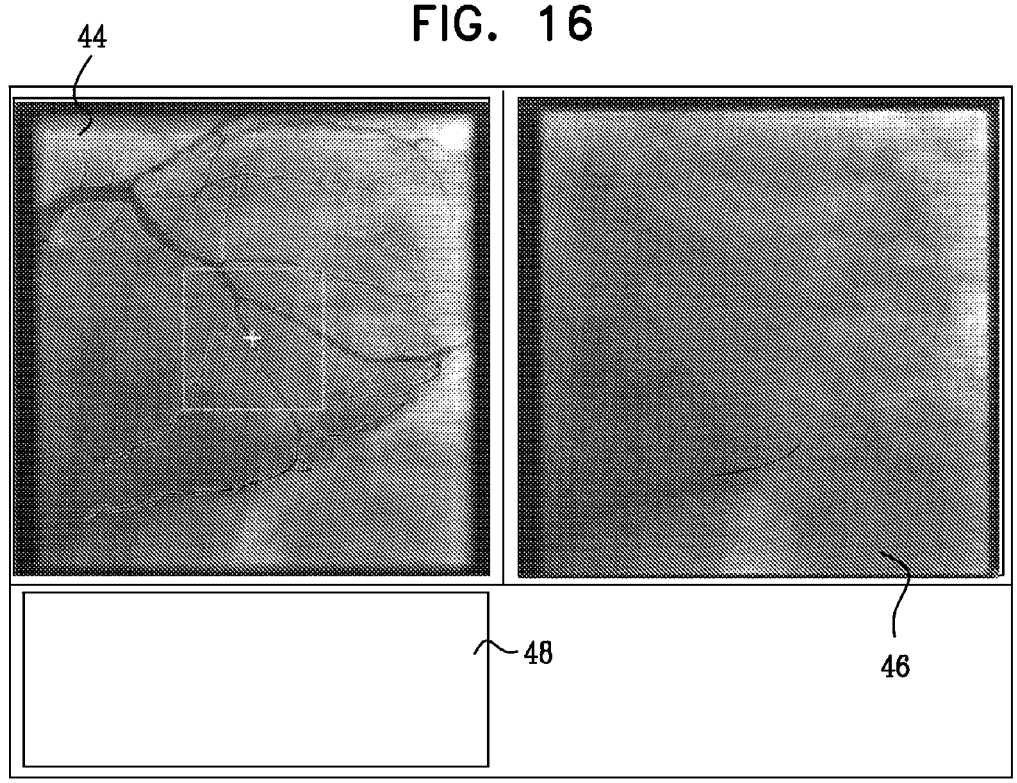
FIG. 16 is a schematic illustration of a screen on which quantitative vessel analysis (QVA) is displayed with respect to a segment of a vessel that is part of a road map, in accordance with some applications of the present invention.
Figure 18:
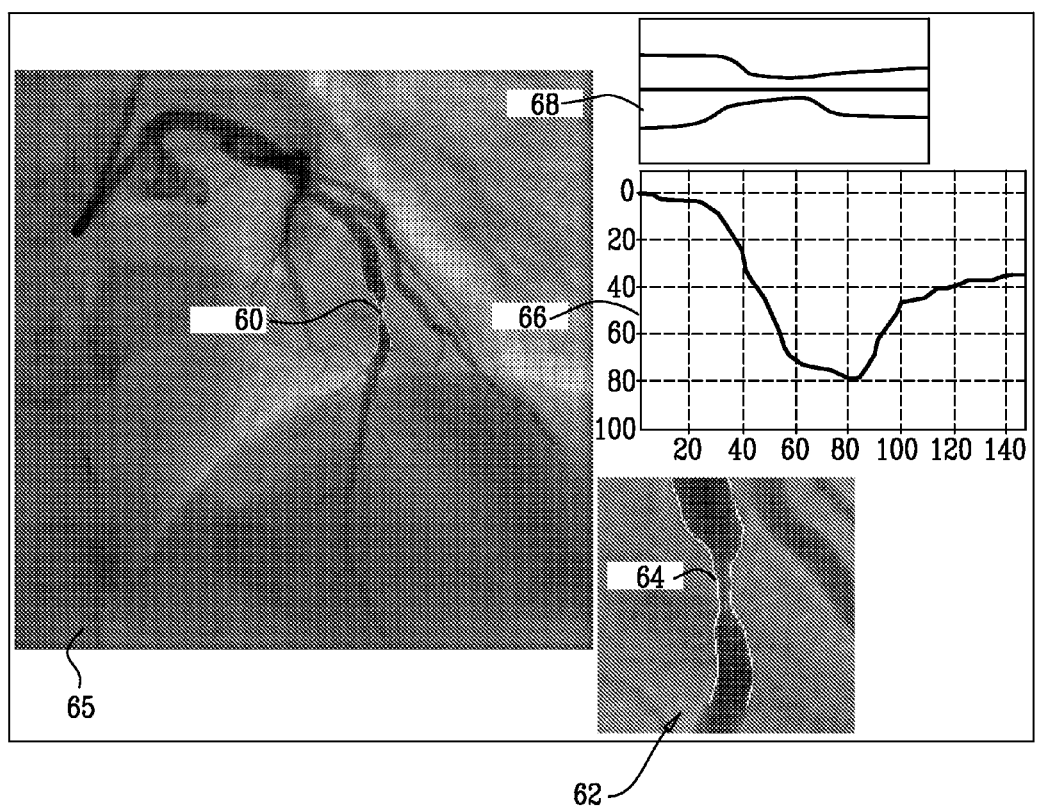
FIG. 18 shows QVA diameter diagrams, in accordance with some applications of the present invention.
Figure 19:
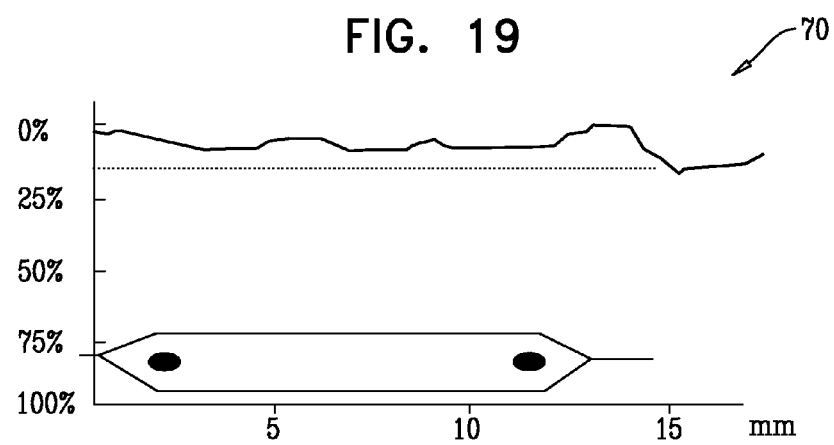
FIG. 19 shows a QVA diagram, comprising a representation of a tool at its relative location within the lesion on which QVA has been performed, in accordance with some applications of the present invention.

Reference is now made to FIGS. 16 and 19, which show, respectively, (a) a QVA box 48 which typically displays a QVA diagram with respect to a segment of a vessel that is part of a road map 44, and (b) a QVA diagram 70, in accordance with some applications of the present invention. As shown in FIG. 19, the horizontal axis of the QVA diagram represents the longitudinal dimension of an occlusion, with distance indicators, while the vertical axis represents the extent (such as percentage relative to the reference artery) of the occlusion. For some applications (typically, when a reference dimension, such as the diameter of the guiding catheter, has not yet been determined), the horizontal axis does not include distance indicators, but represents the longitudinal dimension of the occlusion. Typically, as shown in FIG. 16, and as shown on other figures which are described hereinbelow, the QVA diagram is displayed on the same screen as a road map, an angiogram, and/or a fluoroscopic image of the vessel that is occluded. (Although it is shown as a box in FIG. 16, box 48 typically appears like one of the QVA diagrams shown in FIGS. 18 and 19.)

For some applications, an ROI is indicated and then measurements referring to one or more vessels within the ROI are performed and displayed automatically. In accordance with respective applications, the ROI is determined automatically (for example, by designating the central area of the image frame as the ROI), or is determined by the user. For some applications, road map 44 is displayed alongside a fluoroscopic image stream 46, such as a live fluoroscopic image stream.

Figure 17A:
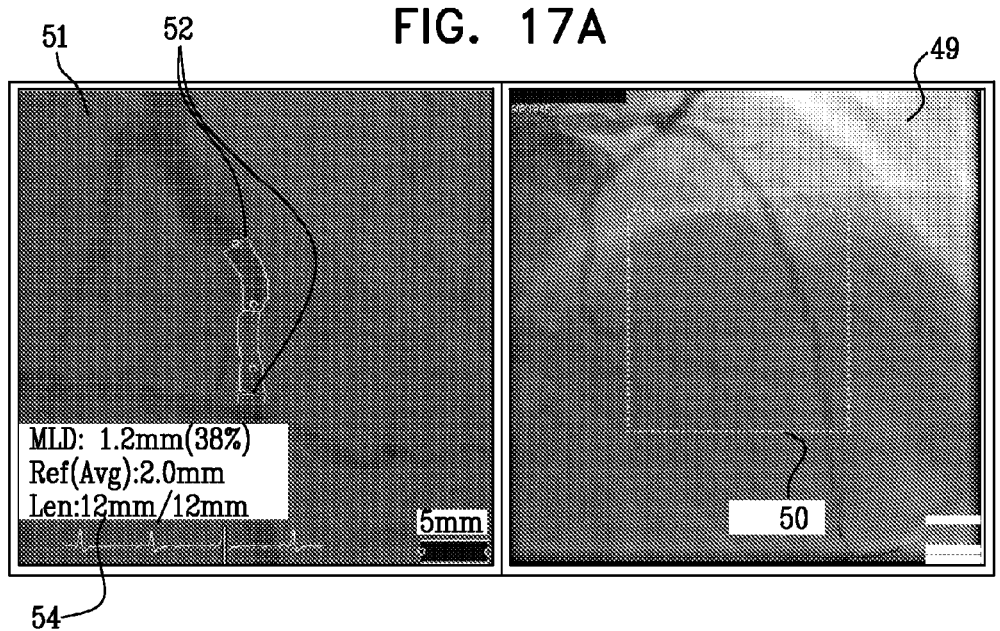
FIGS. 17A-B are schematic illustrations of a screen displaying QVA data with respect to a segment of a vessel that is part a selected angiographic image, in accordance with some applications of the present invention.

Reference is now made to FIG. 17A, which shows displayed on a screen (a) an angiogram 49, an ROI 50 having been identified in the angiogram, (b) an enlargement 51 of the ROI, in which a segment of a vessel (including edges and ends 52) is marked, and (c) QVA measurements 54 of the segment, in accordance with some applications of the present invention. For some applications, as an alternative, or in addition to, displaying a QVA diagram, QVA measurements are displayed, as shown in FIG. 17A.

Figure 17B:
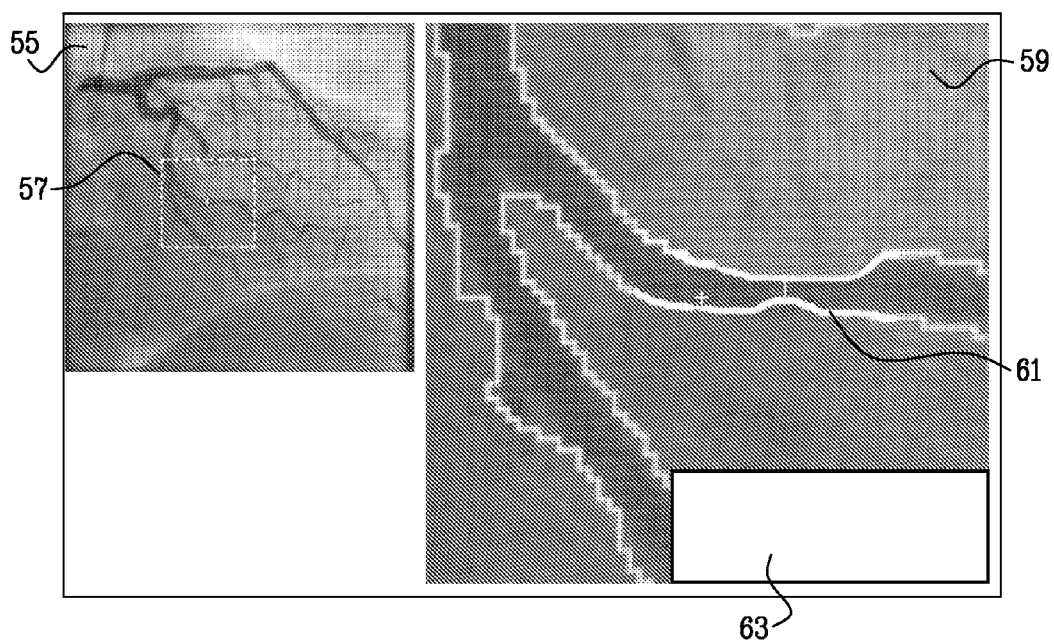

Reference is also made to FIG. 17B, which shows displayed on a screen (a) an angiogram 55, an ROI 57 having been identified in the angiogram, (b) an enlarged roadmap 59 of the ROI, in which a segment 61 of a vessel is marked, and (c) a QVA box 63 of the segment, in accordance with some applications of the present invention. (Although it is shown as a box in FIG. 17B, QVA box 63 typically appears like one of the QVA diagrams shown in FIGS. 18 and 19.)

For some applications, a user designates a single location in an image that is at or near a given location of a given blood vessel in the image. For example, using an input device, the user may click at or near the given location. For some applications, in response to the user designating the single location, the system automatically detects a lesion in the vicinity. For example, the system may identify edge lines and the reference diameters of the lesion. The reference diameters of a lesion are typically the diameters of the vessel at the longitudinal extremities of the lesion (the longitudinal extremities also being known as "healthy shoulders" to those skilled in the art). For some applications, the reference diameters are the broadest location within the section of the blood vessel that is analyzed. In response to detecting the lesion, QVA is performed with respect to the lesion. For some applications, the lesion is graphically indicated, for example, by highlighting or coloring the section of the vessel that is determined to be the lesion.

For some applications, a lesion is automatically detected in accordance with the following procedure. Scan lines are generated perpendicular to the centerline of a segment of the vessel that is sampled. The image is resampled along the scan lines. Corresponding gray-level values are stored as columns of a rectangular matrix M, thereby resampling the segment of the vessel as a straightened vessel segment. For the straightened vessel segment, optimum upper and lower paths are determined (with respect to the middle row of M), which connect the first and last columns of M. The optimization criterion takes into account the changes in gray-level along columns of M, and the paths' slopes. The vessel edge lines are obtained via back projection of upper and lower optimal paths on the original image.

A shortest path algorithm (such as that described by Dijkstra) is used in order to avoid irregularities, such as small gaps and loops, in the edge lines. For some applications, the centerline is corrected based upon the detected edge lines, and new scan lines are constructed. For each new scan line, vessel diameter is defined as a distance between the two points where the scan line intersects vessel boundaries.

For some applications, the technique described for the automatic identification of a lesion is used to automatically identify a guiding catheter. Typically, based on the known diameter (or another known dimension) of the catheter, image units (i.e., pixels) are converted to absolute units (e.g., millimeters or French units). Thus, for some applications, measurements are provided in absolute units, such as, lesion length, the diameter of the vessel at each point along the centerline, and/or minimum lumen diameter (which is also known as the MLD). For some applications, the level of occlusion (which is typically provided as a percentage) at the minimum lumen diameter is determined by comparing the diameter of the vessel at that point, to the diameter of the vessel at reference points of the vessel.

For some applications, in response to the user designating the single location (as described hereinabove), edge detection and QVA are automatically performed up until proximal and distal locations that are at suitable distances along the vessel in, respectively, proximal and distal directions. For some applications, QVA is performed at distances along the vessel from the location that are equal in both proximal (i.e., typically upstream) and distal (i.e., typically downstream) directions along the vessel. Alternatively, the proximal distance is greater than the distal distance. For example, in some cases it may be planned for a stent to be deployed at a lesion within the blood vessel, such that the majority of the stent is deployed proximal of the center of the lesion. Therefore, in response to the user designating the center of the lesion, the QVA is performed up to a distance along the blood vessel in the proximal direction that is greater than the distance along the blood vessel along which the QVA is performed in the distal direction. Further alternatively, the proximal distance is less than the distal distance (for example, in cases in which the center of a stent is to be deployed at a location that is distal with respect to the center of a lesion).

For some applications, the maximum total distance along the blood vessel along which QVA is performed typically automatically, is equal to the length of the longest balloon or stent that is used with the system. For some applications, the total distance along the blood vessel along which QVA is performed is equal to the length of the stent most likely to be used. In accordance with respective applications of the invention, such distances are preset, or are indicated by the user.

For some applications, the narrowest location within the region with respect to which the QVA is performed is marked, and/or the minimal lumen diameter at that location is indicated at that location. As described hereinabove, for some applications, the system automatically detects the reference diameters of a lesion. For some applications, the diameter of the lumen at the healthy shoulders is displayed. As described hereinabove, for some applications, the system automatically performs QVA along a given distance along the vessel. For some applications, the system automatically detects reference diameters of a lesion within that distance, and (optionally) displays the diameter of the lumen at the healthy shoulders of the lesion. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user moves a cursor (i.e., a manually controlled indicator on a computer screen) along (i.e., through, on, beside, over, or parallel to the length or direction of) the designated vessel in the image, and interactively receives an indication of the vessel's diameter at the current location of the cursor. Alternatively or additionally, the user receives an indication of the minimum lumen diameter, or of reference diameters of a lesion in the vicinity of the current location of the cursor. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user designates a first location with the cursor. Subsequently, the user moves the cursor along the blood vessel and receives an indication of the average diameter, the minimum diameter, and/or another quantitative measure of the blood vessel between the first location and the current location of the cursor. Alternatively or additionally, the user moves a cursor along the designated vessel and interactively receives an indication of the longitudinal distance between the current location of the cursor and the first location, the proximal end, and/or the distal end, of the vessel. Further alternatively or additionally, the user receives an indication of the minimum lumen diameter, or of reference diameters of a lesion in the vicinity of the current location of the cursor. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user moves a cursor along the designated vessel and interactively receives an indication of the longitudinal distance between the current location of the cursor and the proximal location of the vessel described hereinabove. Alternatively or additionally, the user moves a cursor along the designated vessel and interactively receives an indication of the longitudinal distance between the current location of the cursor and the distal location of the vessel described hereinabove. Typically, the aforementioned longitudinal distances are calculated along the vessel's center line. Further typically, the distances are determined based upon some known anatomical feature, or based upon a known dimension of another element that is, or has been, present in the image stream, as described hereinabove.

For some applications, the interactive QVA techniques described in the previous paragraph are used to replace virtual stenting. For example, instead of determining which stent should be placed at a lesion by graphically generating a virtual stent at the lesion, QVA is performed with respect to the lesion. Based upon the QVA, it is determined which stent should be placed at the lesion, and/or specific dimensions of a stent that should be placed at the lesion.

For some applications, as the user moves the cursor over the vessel, the portion of the vessel over which the cursor has moved is graphically indicated, for example, by highlighting or coloring the section of the vessel over which the cursor has moved. For some applications, in this manner, the user generates a graphical indication of a lesion. For some applications, such graphical indication of the lesion is used to replace virtual stenting.

For some applications, in response to an input from the user, the processor only allows movement of the cursor on the screen along (i.e., through, on, beside, over, or parallel to the length or direction of) paths of the blood vessels. For example, the cursor may be allowed to move along center lines, or other lines within the blood vessels. Or, the cursor may be allowed to move alongside the blood vessels but in a direction that is parallel to paths (for example, center lines) of the blood vessels.

Reference is now made to FIG. 18, which shows QVA diameter diagrams 66 and 68, in accordance with some applications of the present invention. As described hereinabove, for some applications, an ROI 62 is identified (for example, an ROI in an angiogram 65 is identified, as shown in FIG. 18). For some applications, a user identifies and designates the location of the center of a lesion 64, for example, by clicking on the center of the lesion in the angiographic image, or in the enlarged image of the ROI. For some applications, QVA diagram 68 of the lesion is generated, in which both edges of the vessel are illustrated at their original shape in the form of a diameter diagram. In diagram 68, the vessel's edges are aligned and depicted along and at both sides of the vessel's straightened center line, such that the center line serves as the horizontal axis of the diagram. Alternatively or additionally, QVA diagram 66 is generated. QVA diagram 66 is a graph which plots the diameter, or the level (e.g., percentage) of occlusion of the blood vessel (on the y-axis) against the longitudinal distance along the blood vessel on the x-axis. Thus, using diagram 66, the cumulative narrowing at any given point along the vessel may be observed. For some applications, generating diagram 66 facilitates identification of the narrowest location within the occlusion and the extent of narrowing at that location.

For some applications, a sequence of endoluminal cross-sectional images is generated by an endoluminal imaging catheter. Respective cross-sectional images of the blood vessel are assigned as corresponding to regions of an extraluminal image of the blood vessel (for example, by registering the endoluminal images to the extraluminal image). QVA diagrams or measurements are generated for regions of the extraluminal image. Respective cross-sectional images of the blood vessel are displayed together with (e.g., alongside) the corresponding QVA diagram and/or measurements. For some applications, the endoluminal images (with or without the corresponding QVA diagrams and/or measurements) are displayed as stacked and aligned along a straightened center line of the blood vessel. For some applications, the endoluminal images are generated by the imaging catheter during its pullback. In accordance with respective applications, the endoluminal imaging catheter may be, for example, an IVUS catheter, an OCT catheter, a NIRS catheter, an MRI catheter, or any combination thereof.

For some applications, QVA is performed in response to the user clicking at or near two locations along a vessel, the locations indicating the proximal and distal edges of the lesion. For some applications, a graphical window appears on the screen, and the two locations are designated based on how the user positions the edges of the window and/or sizes the window, with respect to the designated vessel. For some applications, the size of the window changes automatically until the user clicks to indicate that the then-current size is to be selected.

Reference is now made to FIG. 19, which shows a QVA diagram 70 comprising a representation of a tool at its relative location within the lesion on which QVA has been performed, in accordance with some applications of the present invention. For some applications, when a tool such as a balloon and/or stent is present at the occlusion at the time a QVA diagram is generated, a representation of the tool, or of radiopaque markers or segments thereof, is incorporated into the QVA diagram with the position of the tool indicated relative to the occlusion, as shown. Typically, the tool representation is displayed within the lesion on the QVA diagram, at a location that corresponds to the actual location of the tool within the lesion. For some applications, the location of the tool relative to the lesion is determined automatically. For some applications, QVA is performed automatically, upon the identification of the aforementioned radiopaque markers or radiopaque segments within a vessel. For example, QVA may be performed on a segment of the vessel between the two markers, or along a pre-defined distance along the vessel from a site that is a given distance beyond one of the markers, or between two sites that are at respective given distances beyond respective markers.

For some applications, the distance indicators in a road map described hereinabove are used for measurements (e.g., automatic measurements). For example, measurements may be performed of (a) the dimensions of an artery, such as the length and/or diameter of the artery, and or (b) the dimensions of a lesion, such as the length and/or diameter of the lesion. For some applications, the diameter of a reference point of the artery (or of a different artery), at one or both sides of an occlusion, is measured. In accordance with respective applications, the reference point of the artery is indicated by the user, or is identified, typically automatically, by means of image processing due to its larger diameter relatively to that of the occlusion. For some applications, the reference point of the artery is assumed by the system to be at a set distance from the center of the occlusion, or at a set distance from the center of an ROI.

Figure 20:
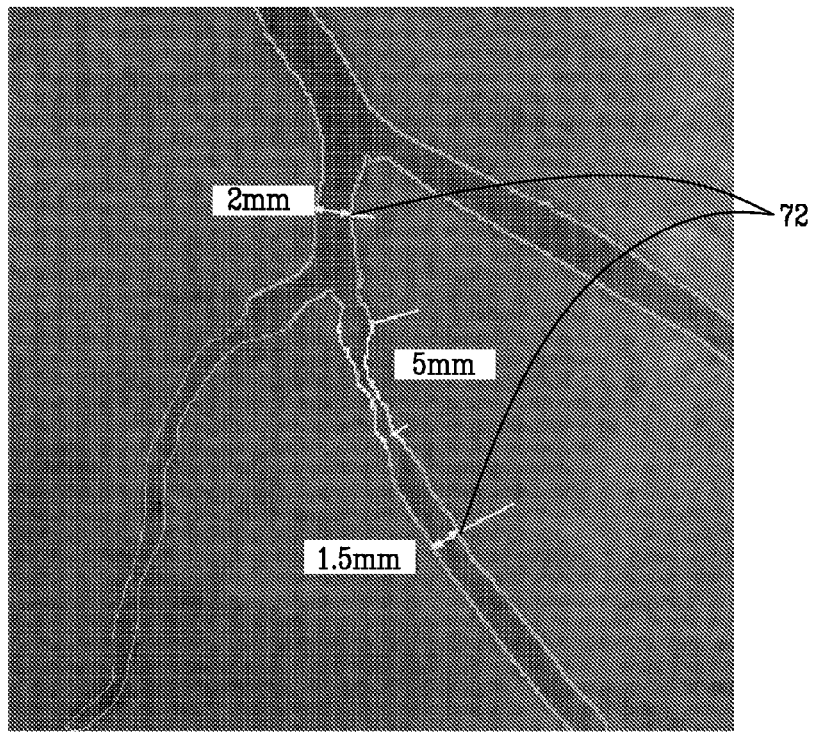
FIG. 20 shows a road map that displays measurements of the diameter of the reference artery at both sides of an occlusion, in accordance with some applications of the present invention.

Reference is now made to FIG. 20, which shows a road map upon which are displayed measurements 72 of the diameter of reference points of an artery on both sides of an occlusion, in accordance with some applications of the present invention.

For some applications, the measurements are used in the selection of a medical tool (e.g., a balloon, and/or a stent) to be deployed at the occlusion.

Image Tracking and Tool Positioning

For some applications, a virtual tool is positioned upon the road map, and/or upon the stabilized images. Typically, the positioning of a virtual tool is an intermediate step leading to the selection and positioning of a corresponding actual tool. For some applications, techniques for the generation and positioning of a virtual tool described in WO 08/107,905 to Iddan, which is incorporated herein by reference, are used in combination with techniques described herein.

For some applications, image tracking is applied to a stream of image frames to facilitate the positioning of a tool, deployment of a tool, the deployment of an already-deployed tool (such as by post-dilatation of a balloon within an already-deployed stent), post-deployment analysis of a deployed tool, general observations, or any combination thereof.

For some applications, image tracking is performed with respect to a radiopaque (or otherwise visible) segment or marker(s) of the tool, which is/are visible in most or all image frames and are identified automatically by means of image processing. The tool is aligned in image frames of the image stream, based on the identified markers or segment of the tool. For example, the image frames may be aligned such that markers in at least most of the image frames are aligned. The aligned image frames are displayed as an image stream. For some applications, image frames are tracked in the aforementioned manner, but with respect to a portion of the subject's anatomy, for example, vascular calcification of the subject.

For some applications, the tool with respect to which image frames are tracked is a balloon, a marker wire, a guide wire, a stent, an endoluminal imaging catheter (e.g., a catheter that uses an imaging modality that is MRI, OCT, IVUS, NIRS, ultrasound, or any combination thereof), and/or an endoluminal measurement catheter (e.g., an FFR catheter).

The identification of the markers or radiopaque segments is typically performed automatically by the system. For some applications, the identification is performed within one or more entire image frames. Alternatively, the identification is performed within an ROI which was previously set by the system and/or the user. Further alternatively, the ROI is automatically set by the system to include regions in which the markers are more likely to appear, and to exclude regions in which the markers are less likely to appear. For some applications, the ROI is indicated graphically, overlaid upon the image stream.

For some applications, markers are identified by the user designating a region within the image in which the markers are more likely to appear, followed by the system automatically identifying the markers within that region. For some applications, the user is subsequently prompted to confirm the identification selection of markers by the system. In accordance with respective applications, the region is designated by the user within a dynamic image stream, or within a static image frame taken from within the image stream. Alternatively, the user clicks on (or otherwise indicates) the device or the vicinity of the device, and, in response, the image tracking with respect to the device markers or segments commences.

Once the markers have been identified in one or more image frames, then the system typically continues to identify (i.e., detect) those markers automatically in the subsequent image frames along the image stream or a segment thereof, and displays a tracked image stream. Typically, in order to detect the markers, the system accounts for phenomena such as the following:

(1) In some image frames, contrast agent may hide, or partially hide the markers. Typically, if the markers are not visible due to the contrast agent in a given frame, then that frame is skipped and is not used in the image-tracked image stream. For some applications, the system identifies markers in image frames in which the markers are partially hidden by the contrast agent, and the image frames are used in the image-tracked image stream.

(2) A fluoroscopic image is typically a two-dimensional projection of the three-dimensional portion of the subject's body that is being imaged. This may result in darkened regions, which appear similar to markers, but which are not markers. For example, regions of the image in which vessels (particularly vessels that contain contrast agent) are projected onto the two-dimensional image such that they appear to be crossing each other, may appear as a dark circle. Similarly, regions in which a tool crosses a vessel, two tools cross each other, a tool crosses the edge of a rib, or a vessel crosses the edge of a rib, may appear similar to a marker. Examples of such tools include a wire (such as a CABG wire, or a guide wire), a CABG clip, an electrode, a lead, and/or a catheter lumen.

(3) In a dynamic image stream, markers may be blurred due to the rapid movement of blood vessels.

For some applications, image frames in which the markers are not identified are automatically skipped. For some applications, blending is performed among tracked image frames which may further stabilize the tracked image frames. When image frames of the original image stream are skipped (e.g., due to non-identification of a marker), then the transition between the adjacent image frames to the skipped image frame is typically performed with blending.

For some applications, a mask is applied to the tracked image stream such that the areas more remote from the tracked markers, which typically have greater motion in the tracked image stream, are blurred, hidden, or partially hidden. Such a masked image stream may be easier for a user to observe, because of the reduction in distractions in the tracked image stream. Alternatively or additionally, the periphery of the image (e.g., the anatomy outside the vascular system) is blurred, hidden, or partially hidden.

For some applications, the automatic identification of markers comprises some or all of the following phases, which are typically performed in real time:

a. Pre-processing: Individual image frames (or an ROI within such frames) along the image sequence are pre-processed in order to facilitate the subsequent identification of markers. Such pre-processing typically comprises the reduction of static and/or dynamic noise, background removal, or a combination thereof. For some applications, a median filter, a Mexican hat filter, a directional Mexican hat filter, and/or a low-pass filter is applied to the individual image frames. For some applications, the preprocessing includes the detection and removal from the image frames of CABG wires, wires and/or electrodes of implanted tools such as pacemakers or defibrillators, and/or wires and/or electrodes of external devices such as an ECG monitor, and/or an external defibrillator.

b. Filtering of non-marker-like features: Individual image frames (or an ROI within such frames) along the image sequence are processed to filter out remaining features that are clearly not markers. For some applications, the filtering includes the application to the image frames of a median filter, a Mexican hat filter, a directional Mexican hat filter, a maximal stable external regions (MSER) filter, an MSER-like filter, a Hessian filter, or a combination thereof.

For some applications, Hessian eigenvalues are calculated for each pixel in each image frame, or for all pixels within an ROI of the image frame. Typically, local clusters of pixels with high minimal eigenvalues represent a "paraboloid-like" area in the image and are identified as a potential radiopaque marker.

c. Scoring: Remaining features in individual image frames (or an ROI within such frames) along the image sequence are assigned a "fitness" score (i.e., a "markerness" score, or a "dotness" score in the case of the most common markers), describing the likelihood that they are markers. For some applications, the score is calculated from the abovementioned filtering.

d. Matching: Remaining features in individual image frames (or an ROI within such frames) are analyzed for matching with one another. For example, in the case of aiming to detect the two radiopaque markers of a coronary balloon, pair matching is performed. Such matching is typically performed based upon relative location, distance, orientation, visual similarity, and/or other factors.

e. Detection: For some applications, once a pair of clusters (with such two clusters being strong candidates to be tool markers) has been identified at a similar distance from one another and/or relative angle to one another in several consecutive image frames, the pair of clusters is determined to be the two markers of a tool.

f. Tracking: Typically, image tracking, as described hereinabove is performed with respect to the two markers for the purposes of image stabilization and/or enhancement.

It should be noted that while using a pair of radiopaque markers as a primary example, the techniques disclosed above (or a derivation thereof) may be applied to other radiopaque (or otherwise visible) segment(s) or marker(s) or feature(s) of a tool, or feature(s) of the anatomy, which are visible in most or all image frames.

For some applications, for the purpose of image tracking, the identified segment or marker(s) of the tool is aligned automatically in most, or all, image frames such that it remains at a similar or same relative position throughout the image stream. Further typically, this results in the tool being aligned automatically in most, or all, image frames such that it remains at a similar or same relative position throughout the image stream.

For some applications, a virtual line that connects the markers is aligned such that it remains at the same or a similar relative position throughout the image stream. For example, the alignment may include translating individual image frames such that the markers (or the virtual line connecting the markers) remain at a same or similar location within the image frames throughout the tracked image stream. Alternatively or additionally, the alignment includes rotating individual image frames such that the angle of the virtual line connecting the markers is same or similar throughout the tracked image stream. Further alternatively or additionally, the alignment includes scaling of individual image frames such that the distance between the markers is the same throughout the tracked image stream. For some applications, the alignment is performed with respect to a virtual feature calculated from the individual locations of the markers. For example, the virtual feature may be an average between the locations of the individual markers, or a weighted average of the locations of the individual markers.

For some applications, image tracking on markers, or on a virtual feature derived from the markers, continues for as long as certain parameters pertaining to such markers are observed at similar values in at least most of the image frames (or in a ROI within such frames). For example, the parameters may include the markers' location, distance from one another, angle relative to one another, linear velocity between consecutive frames, angular velocity between consecutive frames, sizes, "markerness" score, x-ray intensity, surrounding intensity gradients, or any combination thereof.

Typically, the aforementioned image tracking results in the tool being displayed as relatively stable, while the surrounding anatomy is displayed as moving relative to the generally-stable tool in the course of the organ's motion cycle.

For some applications, visibility of image elements surrounding the tool is reduced in the displayed, tracked image stream, in order to reduce visual distractions. Typically, such reduction in visibility facilitates observation of the tool and the vicinity of the tool within the tracked image stream. For some applications, the reduction in visibility is achieved by applying a mask to the images, such that the visibility of regions of the displayed tracked images that are relatively remote from the tool is reduced. For some applications, the visibility of the image elements is reduced gradually, such that there is a typically inverse relationship between the distance of an image element from the tool and the visibility of such image element in the displayed, tracked images.

For some applications, in the region of the tool, pixels are displayed that are not averaged. Pixels that are distant from the tool are averaged with pixels from other image frames that are in a corresponding location to those pixels, for example, as described hereinbelow. For some applications, there is a direct relationship between the extent to which pixels are averaged, and the distance of the pixels from the tool.

Image tracking with respect to a portion of the tool typically effects a visual separation between two elements of the motion of the tool positioned within a vessel attached to the heart. The motion of the tool together with the vessel is typically hidden, while the motion of the tool relative to the vessel typically remains visible. For some applications, such separation of motion elements typically facilitates the ability of the user to determine the extent of the motion of the tool relative to the vessel (e.g., cyclic longitudinal motion within the blood vessel) in the course of the heart's motion cycle. That, in turn, typically enables the user to determine the importance of deploying the tool at a specific phase in the motion cycle, and if so, at which specific phase, and location.

For example, when placing a balloon (or a balloon carrying a stent) relative to a designated lesion within a coronary artery, image tracking is performed on the radiopaque marker(s) of the balloon. Consequently, the motion of the balloon together with the artery, in the course of the heart's motion cycle, is typically hidden. At the same time, the motion of the balloon relative to the artery, in the course of the heart's motion cycle, typically remains visible. Consequently, the user can observe (typically while being demonstrated by contrast agent) the location of the balloon prior to its inflation, and/or the stent prior to its deployment, at a systolic or end-systolic phase versus a diastolic or end-diastolic phase. Based on the observed locations of the balloon or the stent, deployment of the balloon or the stent at a desired location is timed to the phase in the cardiac cycle at which the pre-deployment position is at the desired location.

In accordance with respective applications, the user observes the balloon in the described manner, in real time, in near real time, or in reloop mode.

For some applications, the extent of the motion of the balloon relative to the artery is quantified automatically. For example, the location of the tool's markers or radiopaque segments relative to a known anatomical feature (such as an occlusion, a bifurcation, an ostium) is automatically determined over the course of a cardiac cycle.

For some applications, image tracking is performed with respect to the radiopaque segment(s) of a tool configured to penetrate an occlusion. The inventors hypothesize that such image tracking facilitates determination by a user of the orientation of the tool relative to the vessel at any given moment, and thus assists the operator in determining when to push forward and/or activate the tool.

For some applications, identification of the end-diastolic and end-systolic points within a cardiac cycle is determined from an ECG signal, and/or by means of image processing. For example, such means of image processing may include the identification of a reversal of the direction in which a tool's radiopaque segment(s) moves.

For some applications, the possibly-varying location of the tool vis-à-vis the vessel in the course of the heart's motion cycle is further highlighted by graphical means. For example, portions (such as the radiopaque segment(s) or marker(s)) of the tool may be presented in different colors, shapes, textures and/or sizes at a systolic or end-systolic phase versus a diastolic or end-diastolic phase. Alternatively or additionally, other elements in the image frames change their appearance according to the phase in the motion cycle. Further alternatively or additionally, sounds are used to denote a selected phase in the motion cycle.

Figure 21:
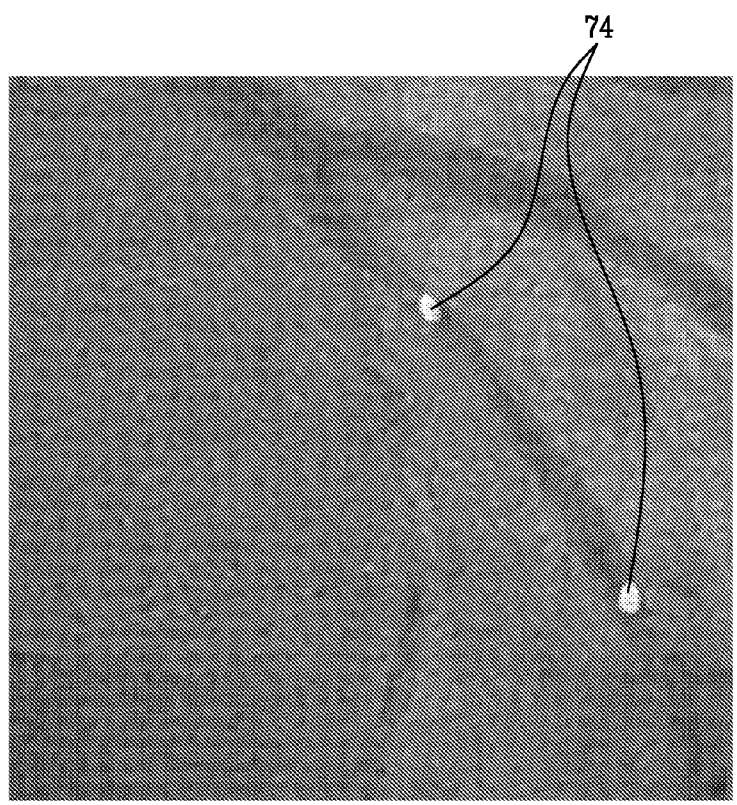
FIG. 21 shows markers of a balloon that are highlighted during at least one given phase of the cardiac cycle, in accordance with some applications of the present invention.

Reference is now made to FIG. 21, which shows markers 74 of a balloon within a vessel in an angiogram. For some applications, the markers are artificially colored a first color in one phase of the cardiac cycle (e.g., the end-systolic phase), and are colored a different color in a different phase of the cardiac cycle (e.g., the end-diastolic phase).

Figure 22:
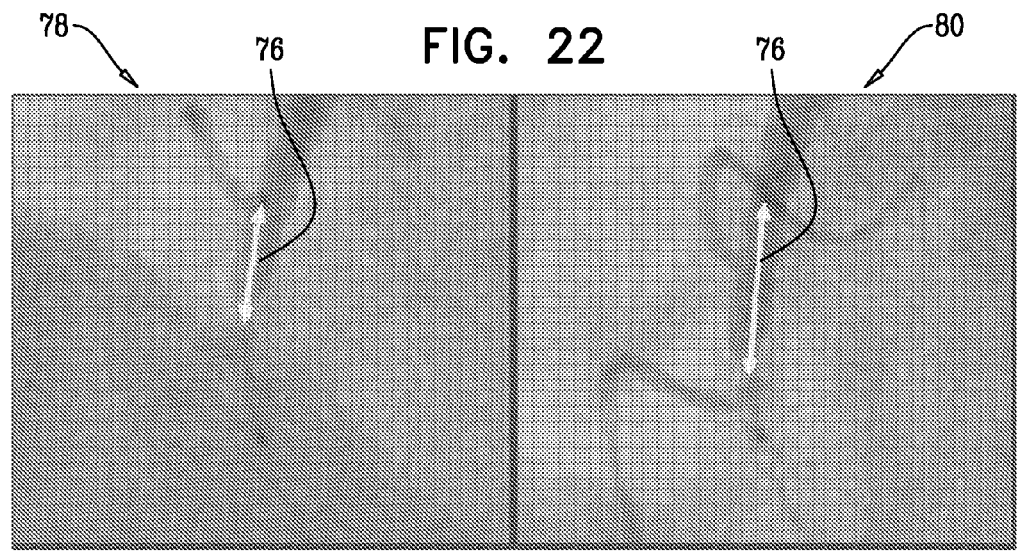
FIG. 22 shows two stabilized images of markers of a balloon inside an artery, at respective phases of the cardiac cycle, in accordance with some applications of the present invention.

Reference is also made to FIG. 22, which shows images 78 and 80 of markers of a balloon situated within a coronary artery, at respective phases of the subject's cardiac cycle. Arrow 76 in each of the figures denotes the distance of the upper marker from the beginning of an occlusion of the coronary artery. It may be observed that the pre-deployment position of the marker relative to the artery is substantially different at different phases of the cardiac cycle, indicating to the inventors that proper deployment at a desired location should to be timed to the phase in the cardiac cycle at which the pre-deployment position is at the desired location.

For some applications, techniques are provided for facilitating the determination of the location of a tool, such as a balloon or a balloon carrying a stent, with respect to an artery, during image sequences for which a contrast agent has not been administered to the subject. For some applications, the current locations of radiopaque markers or radiopaque segments of the tool are determined with respect to a road map that was generated from a previously-acquired angiogram. Typically, the procedure includes some or all of the following phases, and is typically performed in real time:

a. A road map is generated, typically automatically, for example, according to techniques described hereinabove. Typically, the road map is updated automatically during the procedure, in response to the system detecting that a new angiographic sequence has commenced, as described hereinabove. For some applications, commencement of the new angiographic sequence is detected even when the angiographic sequence is performed under fluoro mode. For some applications, the shape of a vessel through which tools are inserted changes in the course of the procedure due to occlusions being reduced, the tool itself straightening the artery, and/or other reasons, and the road map is updated in order to account for these changes.

b. Features residing within the vessel at a relatively fixed location are identified, such features being observable even in images generated in the absence of contrast agent. Such features may include a distal portion of the guiding catheter through which the tool is inserted, a radiopaque portion of the guide wire upon which the tool is inserted, and/or other features. For some applications, the identification of such features is automatic, or semi-automatic (i.e., requiring some user interaction but less than would be required without using the techniques described herein), for example, in accordance with techniques described hereinabove. For some applications, the entire length of the guide wire (or of the catheter carrying the tool) is identified, for example using techniques similar to the ones described hereinabove for the automatic identification of center lines.

c. A current image stream of the tool inside the blood vessel is generated. The markers or radiopaque segments of the tool that is currently inserted into the blood vessel are identified in the image stream, typically automatically and typically in real time, according to techniques described hereinabove. The markers or radiopaque segments are identified even in current images generated in the absence of contrast agent (and in which the artery itself is not visible). The location of the markers with respect to the observable features is determined based upon the current image stream.

d. The tool markers or radiopaque segments are projected, typically automatically and typically in real time, upon the previously-generated road map. Typically, the current location for marker projection within the road map is calculated relative to the aforementioned observable features described in step b. For example, the current distance(s) of the markers from the observable feature(s) (as determined in step c) may be applied along the applicable vessel in the road map in order to determine the location on the road map at which the markers will be projected. For some applications, the angiogram from which the road map is generated is gated to a specific phase in the cardiac cycle (e.g., the end-diastolic phase), and the location of the markers with respect to the observable features is determined in a current image frame that is also gated to that phase.

In an alternative application, the road map is projected (continuously or in a gated manner) upon the image stream that contains the markers or radiopaque segments (as opposed to the image stream being projected upon the road map).

Synchronized Tool Deployment

For some applications, once the location of the tool is suspected to or has been determined to vary in the course of the organ's motion cycle, actuation of the tool is synchronized to a selected phase in the motion cycle of the organ. For some applications, the synchronized actuation of the tool is performed in accordance with techniques described in WO 08/107,905 to Iddan, which is incorporated herein by reference.

For example, when inflating a balloon (or, for example, a balloon carrying a stent) relative to a designated lesion within a coronary artery, and if the pre-deployment position of the balloon relative to the artery varies considerably over the course of the heart's motion cycle, then the user may place the balloon such that its location relative to the lesion is correct at a specific phase of the cardiac cycle, and then inflate the balloon in synchronization to that phase. For some applications, such synchronized inflation is performed by means of apparatus for facilitating synchronized inflation described in WO 08/107,905 to Iddan, which is incorporated herein by reference.

For some applications, inflation is synchronized specifically to a selected phase in the subject's ECG signal. The ECG signal is typically received from an ECG monitor, or from a cardiac rhythm management (CRM) device, such as a pacer, or a defibrillator. For some applications, the processor identifies the selected phase of the ECG signal. Alternatively, the selected phase (e.g., the R wave of the ECG signal) is identified by the ECG monitor. Further alternatively, the selected phase (e.g., the R wave of the ECG signal) is identified by the CRM device.

For some applications, the aforementioned synchronization (and/or the synchronization of the actuation, deployment, and/or movement of other tools described herein) accounts for the delay in the generation of the ECG signal by the ECG monitor. For example, the delay may be determined in the following manner: A cardiac signal is generated by an electronic patient simulator. That signal is then fed as an input signal to the ECG monitor. The time difference between that input signal and the corresponding ECG signal produced by the ECG monitor is measured with an oscilloscope. If the delay D1 is measured in milliseconds and the heart rate (HR) is measured in beats per second, then, in order to actuate the tool in synchronization with a given phase of the ECG signal (e.g., the R-wave), a signal to actuate the tool is applied ((1000/HR)−D1) milliseconds after the given phase of the ECG cycle is detected.

For some applications, the value of HR as applied to the aforementioned synchronization is set according to the subject's most current heart rate. Alternatively, the value of HR is set according to the subject's average heart rate along a selected number of most recent cardiac cycles.

Figure 23A:
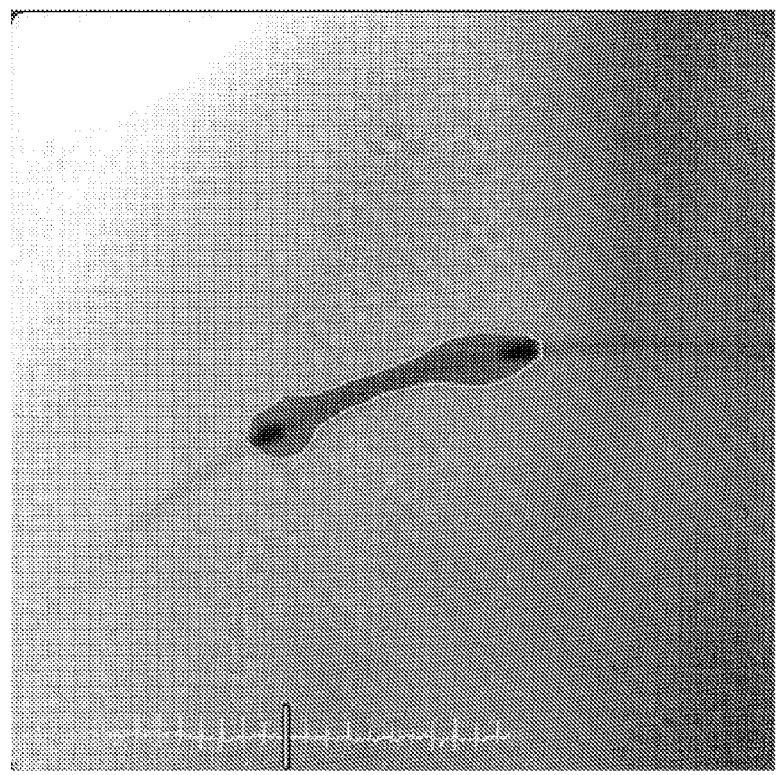
FIG. 23A shows a balloon being inflated inside a stent, there being overhanging regions at ends of the balloon that are inflated in synchronization with the subject's cardiac cycle, in accordance with some applications of the present invention.

Reference is now made to FIG. 23A, which shows an image of a balloon being inflated inside a stent. In FIG. 23A, edge lines have been added manually to the balloon, although, in accordance with some applications of the present invention, edge lines are added automatically. In the course of the deployment of certain tools within a vessel, a balloon is inflated within the tool, in order to expand the tool such that the tool comes into contact with an inner surface of the vessel. For example, a balloon may be inflated inside a stent such that the stent is brought into contact with an arterial wall. Alternatively, a balloon may be inflated inside a prosthetic valve, in order to deploy the valve adjacent to the remains of a natural valve. Further alternatively, a balloon may be inflated inside a graft, in order to deploy the graft.

Typically, the tool is shorter than the balloon, therefore, the balloon has overhanging portions at each end of the balloon. In such cases, one or both of the overhanging portions of the balloon typically initially expands before the remainder of the balloon expands. The overhanging portion becomes attached to the inner surface of the vessel, and, at that point, the longitudinal position of the balloon (and the tool) relative to the vessel typically becomes fixed, such that there is no longitudinal motion of the balloon relative the vessel. Subsequently, inflation pressure is further raised so that the tool itself attaches to the inner surface of the vessel.

For some applications, synchronization is applied such that the inflation is performed in a stepwise manner, in phase with a selected phase of the cardiac cycle, throughout the entire inflation procedure. Alternatively, synchronization is applied only during certain segment(s) of the inflation process, while inflation during earlier or later segment(s) of the process remains continuous.

For some applications, when deploying a tool (e.g., a stent) using the balloon, synchronization is applied in one or more steps to the inflation of one or more of the overhanging portions of the balloon, until the overhanging portion has become attached to the inner surface of the vessel and the longitudinal position of the balloon relative to the vessel has been fixed. Subsequently, the remainder of the inflation process, is continuous (and typically not synchronized) until the stent itself has become attached to the inner surface of the blood vessel.

Alternatively, inflation of the balloon is at first continuous until sufficient pressure has been applied to unfold the balloon. Subsequently, synchronization is applied in one or more steps to the inflation of one or more of the overhanging portions of the balloon, until the overhanging portion has become attached to the endoluminal wall and the longitudinal position of the balloon relative to the vessel has been fixed. Subsequently thereto, the remainder of the inflation process is continuous (and not synchronized) until the stent itself has become attached to the inner surface of the blood vessel.

For some applications, timing of the aforementioned one or more synchronized steps, relative to the detected desired phase in the vessel's motion cycle, takes into account parameters which affect the time delay D2 milliseconds between the activation of an inflation step by the aforementioned device for facilitating synchronized inflation and the corresponding increase in the diameter of the balloon and/or stent being inflated. For some applications, parameters that affect D2 include catheter parameters (e.g., length, inner diameter), balloon and tool (e.g., stent) parameters (e.g., length, diameter, nominal pressure), inflation fluid parameters (e.g., viscosity, relative portions of saline and contrast agent), or any combination thereof.

Typically, an additional parameter which affects the aforementioned time delay D2 is the amount of air trapped within the catheter carrying the balloon and/or stent. For some applications, activation of the apparatus for facilitating synchronized inflation is preceded by suction of trapped air out of the catheter. For example, such suction may be performed manually by the operator, such as by means of a syringe connected to the proximal end of the catheter. Alternatively, the suction may be performed by an electromechanical apparatus. For some applications, the electromechanical apparatus is coupled with the apparatus facilitating synchronized inflation.

For some applications, delay D2 is measured in milliseconds, and the heart rate is measured in beats per second. In such cases, subsequent to detecting the desired phase of the subject's ECG (or other) signal, the actuation signal for actuating the tool is generated after ((1000/HR)−D2) milliseconds.

For some applications, in order to account for the aforementioned ECG-related delay D1 and inflation-related delay D2, and where the heart rate is calculated as HR beats per second, the actuation signal is delayed by ((1000/HR)−D1−D2) milliseconds, after detecting the desired phase of the subject's ECG signal.

For some applications, synchronization is applied to the deployment of a stent that is not balloon-inflatable but rather is self-expanding. For some applications, a delay of D3 milliseconds between the activation of the self-expansion mechanism and the stent actually expanding to the lumen's internal diameter is determined by means of ex-vivo experimentation with the stent. Alternatively or additionally, D3 is determined by means of performing measurements, under intra-procedural imaging, of in-vivo stent deployments.

For some applications, delay D3 is measured in milliseconds, and the heart rate is measured in beats per second. In such cases, subsequent to detecting the desired phase of the subject's ECG (or other) signal, the actuation signal for actuating the tool is generated after ((1000/HR)−D3) milliseconds.

For some applications, when accounting for the aforementioned ECG-related delay D1 and expansion-related delay D3, and where the heart rate is calculated as HR beats per second, the actuation signal is generated ((1000/HR)−D1−D3) milliseconds, after detecting the desired phase of the subject's ECG signal.

In further applications, the aforementioned synchronization is applied to the gated (for example, stepwise) motion and/or activation of a tool used for penetrating an occlusion within the vessel, and/or to a different tool.

Reference is now made to FIGS. 23B and 23C, which are schematic illustrations of apparatus for use with an inflation device 82, including a reusable portion 84, and a single-use portion 86, in accordance with some applications of the present invention. The reusable portion may be coupled and decoupled with respect to the single-use portion, as shown, respectively, in FIG. 23B and FIG. 23C. As described in WO 08/107,905 to Iddan, which is incorporated herein by reference, some portions of the apparatus for facilitating a synchronized inflation of a balloon and/or stent may be reusable, while other portions may be intended for single use. For some applications, the reusable portions are ones which do not come in contact, during the inflation process, with the inflation substance (such as a fluid), and the portions intended for single use are ones which come in contact, during the inflation process, with the inflation substance (such as a fluid). Alternatively or additionally, the reusable portions are ones which do not come in contact, during the inflation process, with the tool being inflated (such as a catheter carrying a balloon, a stent, and/or a valve), and the portions intended for single use are ones which come in contact, during the inflation process, with the tool being inflated (such as a catheter carrying a balloon, a stent, and/or a valve).

Enhancement of an Image

For some applications, the image of the tool within the stabilized image stream is enhanced in real time or near real time. For some applications enhancement of the image of the tool is performed in combination with the techniques described in WO 08/107,905 to Iddan, which is incorporated herein by reference.

For some applications, enhancement is performed automatically upon frames that have been image-tracked such that the tool is displayed in a same or similar relative location throughout most or all frames, as described hereinabove. For some applications, enhancement is performed by means of temporal filtering of the image-tracked frames. Typically, enhancement is performed in real time, or in near real time.

For some applications, the temporal filtering applies a weighted averaging function to the value of each pixel, as defined by its relative locations in a series of consecutive frames, and displays the resulting image. Alternatively or additionally, the temporal filtering applies a median function to the value of each pixel, as defined by its relative locations in a series of consecutive frames, and displays the resulting image. Further alternatively or additionally, the temporal filtering applies a mode function to the value of each pixel, as defined by its relative locations in a series of consecutive frames, and displays the resulting image.

For some applications, in addition to the application of a temporal filter, a spatial filter is applied to increase the contrast in the enhanced image. For example, the spatial filter may be a leveling filter. For some applications, contrast is increased by histogram stretching, and/or by gamma correction.

In accordance with respective applications, contrast enhancement is specifically applied to the edges of a tool, such as a balloon, or to the struts of a tool, such as a stent.

For some applications, only the final image, representing the outcome of the enhancement process, is displayed. Alternatively, intermediate frames, reflecting gradual enhancement, are also displayed on-line.

For some applications, enhancement is performed upon a number of typically-consecutive gated image frames. When using gated images, the enhancement is typically applied to fewer image frames than when the enhancement is applied to non-gated image frames, which may degrade the outcome of the enhancement process. However, such gated frames are often already aligned to a substantial extent, which may improve the outcome of the enhancement process.

For some applications, the enhancement is performed with respect to an image of an anatomical structure. For example, the anatomical structure may be a valve or a portion thereof, and/or a section of a vessel. For some applications, the structure is a lesion, which is typically visualized during contrast injection. For some applications, the lesion is identified by the user, for example, as part of the automated QVA process described hereinabove. For some applications, enhancement is applied, in particular, to the edges of the structure, which are made visible by means of contrast agent, or which are visible even without contrast agent due to a physiological phenomenon. For example, calcification is typically visible even without contrast agent.

For some applications, enhancement is performed utilizing only stabilized (e.g., image tracked, and/or gated) image frames. Alternatively, the enhancement utilizes non-stabilized image frames. For example, in the case of a calcified anatomical structure, such structure is typically more rigid than its environment and therefore motion during the cardiac cycle is typically reduced. Therefore, for some applications, non-stabilized images of the calcified structure are used for the enhancement.

For some applications, for the purpose of enhancing an anatomical structure, the shape and/or orientation of which structure varies during its motion cycle, some or all of the following steps are performed:
  a. The anatomical structure in a selected image frame is identified. For some applications, the identification is automatic (for example, the most significant occlusion along an imaged vessel is automatically identified). Alternatively, the identification of the feature is manual (for example, by the user clicking on the occlusion or in the vicinity of the occlusion in order to initiate the automated QVA disclosed hereinabove).
  b. The same anatomical feature is identified, typically by means of image processing, in additional image frames which are typically part of the same image sequence to which the frame in the preceding step belongs. For some applications, such means of image processing include pattern matching, and/or non-rigid object tracking techniques. For some applications, the image processing includes QVA techniques.
  c. Image frames are realigned, typically automatically, such that the orientation of the anatomical feature in at least most of them is similar.
  d. The aligned image frames are then displayed, according to techniques disclosed hereinabove, in the form of a stabilized image stream or an image stream that is both stabilized and enhanced.
  e. The shape of the aforementioned anatomical feature may vary over the organ's motion cycle. For example, in the area of the occlusion, an occluded vessel may be straight in some phases and twisted in others. For some applications, a baseline image frame is identified, in which the feature is in a shape that is designated as a baseline shape. The anatomical feature is identified in image frames in which the feature does not have the baseline shape, and, in such image frames, the feature is deformed, such that its shape becomes more similar to the baseline shape. The image frames in which the feature has been deformed are displayed in an image stream, together with the baseline image frame. Typically, this results in an image stream in which the shape of the feature is more similar along the image stream, than if the feature had not been deformed in some of the image frames. The deformation of the feature is typically performed automatically.

The deformation described in step (e) above typically facilitates the generation of an enhanced composite image, or enhanced image stream, which is of higher clarity (with respect to the anatomy of the feature) compared with the pre-deformation enhanced image or movie. For some applications, the visibility of the feature in an image stream is increased by deforming the feature as described above, but without applying other image enhancement techniques.

For some applications, the enhancement of images of vessels facilitates the demonstration of such vessels not by pure contrast agent (as is typically done without applications of the current invention), but rather with a mixture of contrast agent with a dilutive agent such as saline. Using a lower total quantity of contrast agent typically reduces risks to the subject's health that may be associated with such an agent. For some applications, mixing of the contrast agent with the dilutive agent is performed by means of a faucet device to which reservoirs of the agents are connected.

For some applications, image enhancement is performed during the positioning of a tool, during the deployment of the tool, and/or upon the completion of the deployment of the tool. For example, an enhanced image or image stream may be used to evaluate whether a tool has been fully deployed.

For some applications, the edges of the enhanced tool are automatically emphasized. Alternatively or additionally, measurements of the enhanced tool are automatically generated and displayed. Such emphasis of edges and addition of measurements may be useful, for example, to evaluate whether the tool has been fully deployed.

For some applications, enhancement is generated from fluoro (i.e., low dose) images as opposed to cine (i.e., high dose) images, despite the typically-lower quality of such images in comparison to cine images. Alternatively, enhancement is generated from cine images.

For some applications, a sequence of endoluminal cross-sectional images generated by an imaging catheter along a vessel segment is displayed together (such as side-by-side) with the enhanced image of that segment and/or of a tool positioned (for example, a balloon) or deployed (for example, a stent) within that segment. For example, the imaging catheter may be an IVUS catheter, an OCT catheter, a NIRS catheter, and MRI catheter, or any combination thereof.

For some applications, enhancement is performed continuously and on-line in the form of a tracked and enhanced image stream. For example, such enhancement may be performed upon a determined number of recent frames, the determined number being set automatically by the system, or set and/or adjusted by the user.

For some applications, enhancement is performed by generating exponential moving average images. For some applications, enhancement is performed by averaging sets of two or more image frames that have been image tracked, in order to generate a plurality of averaged image frames. Thus, moving components in the image frames are, at least to some extent, averaged out, whereas components that appear to be stationary (e.g., the region of the image frames with respect to which the frames are tracked) remain. Subsequently, the averaged image frames are typically displayed as an image stream. For some applications, a moving-average image frame is generated, and an image frame (typically, the most recently acquired image frame) is averaged with the moving-average image frame, in order to generate a new moving-average image frame. Typically, the moving average image frame is an average (or a weighted average) of all of the previously acquired image frames of a given sequence. Alternatively, the moving average image frame is an average (or a weighted average) of a given number of most-recently acquired image frames. This process is repeated in order to generate further moving-average image frames. For some applications, the moving average image frame and the image frame that is averaged therewith, are assigned different weightings. Typically, successive moving-average image frames are displayed as an image stream.

For some applications, the aforementioned tracked and continuously-enhanced on-line image stream is displayed side by side with the native image stream, or the video-tracked image stream, or the gated image stream, or an image sequence of a typically-recent contrast injection, or a typically-recent static angiographic image frame, or a typically-recent static angiographic image frame with the markers or radiopaque segments of a tool displayed thereon, or any combination thereof.

For some applications, a mask is applied to the tracked and continuously-enhanced image stream such that the areas more remote from the tracked markers or radiopaque segments, which typically have greater motion, are blurred, hidden, or partially hidden. Typically, an image stream that is masked in this manner is easier for a user to observe.

Reference is now made to FIG. 24, which shows an enhanced image of an inflated coronary balloon, in accordance with some applications of the present invention. As shown, edges have been emphasized with a line and dimensions have been provided, in accordance with some applications of the present invention. Typically, the edges are emphasized, and/or the dimensions are provided, automatically.

Figure 25:
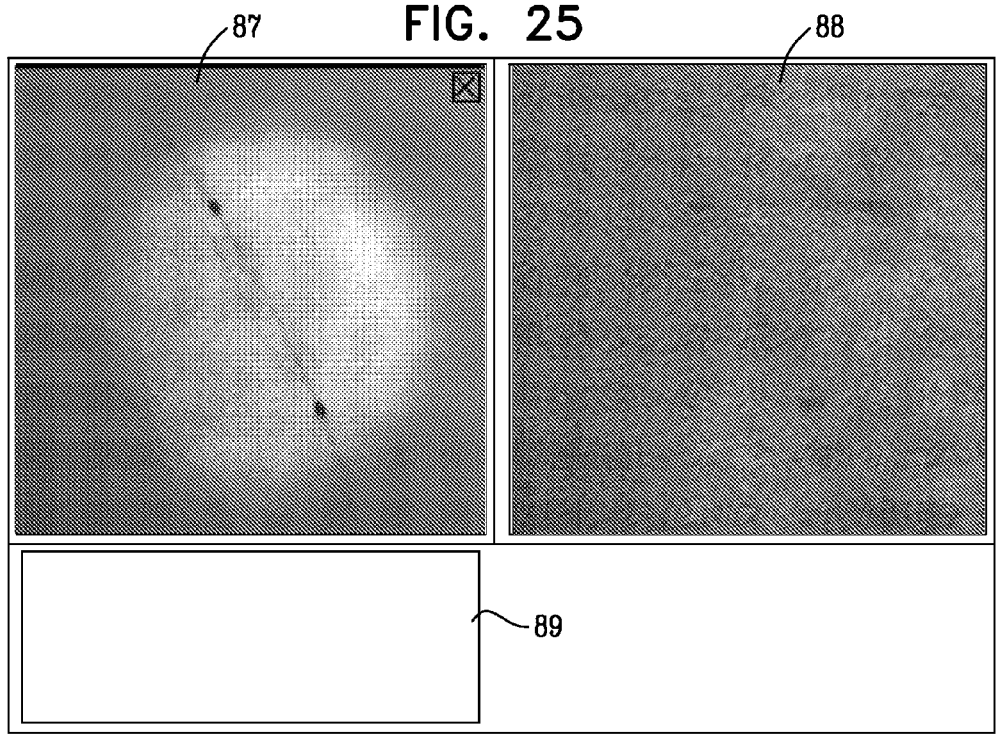
FIG. 25 shows an image of a deployed coronary stent that was automatically enhanced, alongside a raw image of the stent, in accordance with some applications of the present invention.

Reference is now made to FIG. 25, which shows an automatically-enhanced image frame 87 of a deployed coronary stent that was generated, in accordance with some applications of the present invention. The enhanced image was generated from fluoro (i.e., as opposed to cine) images, which typically renders such enhancement more difficult to perform. The enhanced image is shown alongside a native image frame 88 of the image stream from which the enhanced image was generated. For some applications, QVA measurements, and/or a QVA diagram are displayed on the screen, for example in a QVA box 89.

Figure 26:
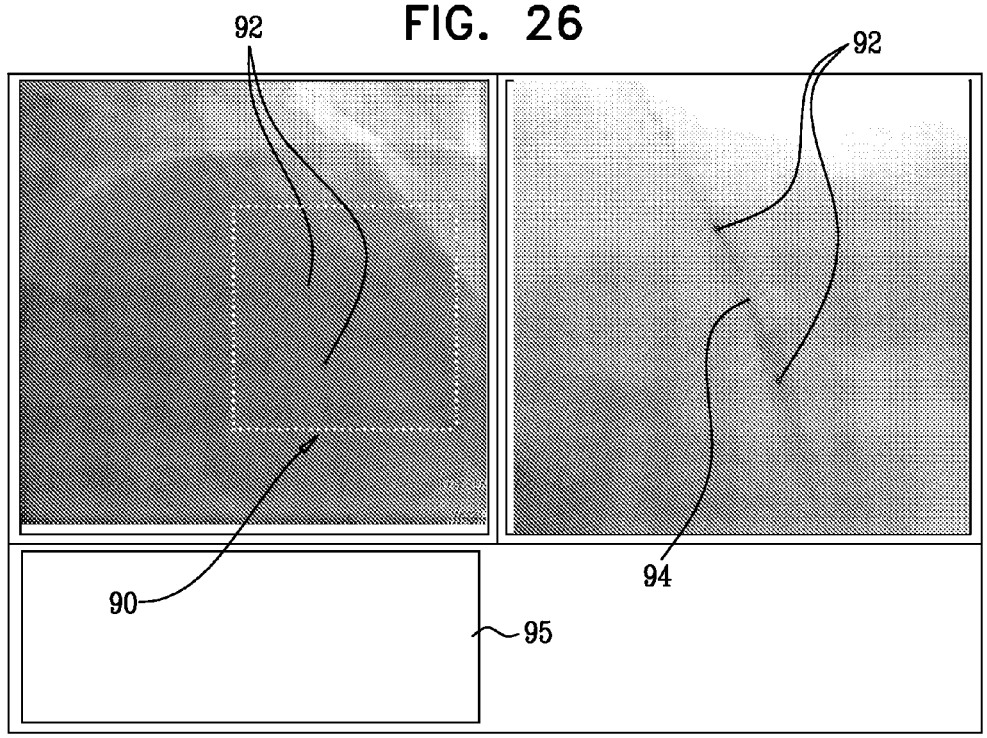
FIG. 26 shows an image stream that was tracked and enhanced, displayed side by side with a native image stream, in accordance with some applications of the present invention.

Reference is now made to FIG. 26, which shows a frame of a tracked and enhanced image stream (on the right) displayed side by side with a frame of the native image stream, in accordance with some applications of the present invention. An ROI 90 is indicated in the native image stream, within which a stent having markers 92 is located. For some applications, only the ROI is displayed in the tracked and enhanced image stream. It may be observed that in the tracked and enhanced image frame, markers 92 and struts 94 of the stent are more visible than in the native image frame. The struts are more visible due to the vicinity of the struts to the markers, the image frames having been tracked and enhanced with respect to the markers. For some applications, QVA measurements, and/or a QVA diagram are displayed on the screen, for example in a QVA box 95.

Figure 27:
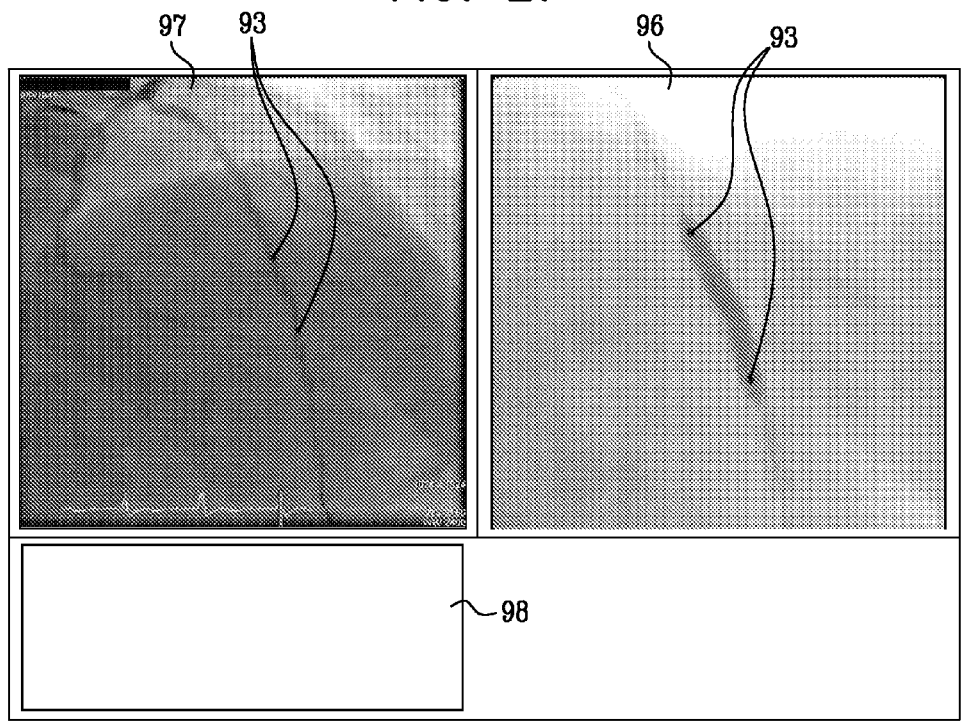
FIG. 27 shows an image stream that was tracked and enhanced, displayed side by side with a recent angiographic image frame, in accordance with some applications of the present invention.

Reference is now made to FIG. 27, which shows a frame 96 of a tracked and enhanced image stream (on the right) displayed side by side with a recent angiographic image frame 97, in accordance with some applications of the present invention. Markers 93 of an inflated balloon may be observed in both of the images. For some applications, QVA measurements, and/or a QVA diagram are displayed on the screen, for example in a QVA box 98.

For some applications, an image stream is enhanced with respect to a tool, such as an inflated balloon, or a deployed stent. An analysis similar to the QVA analysis, which was described hereinabove with respect to vessel edges, is performed and displayed for the edges of a boosted tool.

Additional Techniques for Image Improvement

Images of the heart and its vicinity often comprise additional elements that are not part of the heart itself and/or its vascular structure. Some of these elements are natural ones, such as the rib cage or spine. Some of these elements are artificial elements that were placed within the subject's body in the course of a previously-performed coronary bypass surgery, or that are currently placed on or within the subject's body. For example, the elements may include wires (e.g., CABG wires, or guide wires), electrodes, leads, and/or clips (e.g., CABG clips). Such elements typically appear within a fluoroscopic image as particularly dark (or particularly light in an inverted image).

Such elements, and in particular the latter, artificial ones, may increase the burden placed upon the physician observing the images, as they often divert the physician's visual attention from the heart and the vascular structure. Such diversion of attention may be caused by the additional elements moving at a different frequency and/or magnitude from the heart and its vasculature. In addition, such diversion of attention may be caused by the additional elements being of a different color or gray level from the heart and its vasculature.

For some applications, such additional elements are removed, in full or in part, from a stabilized (e.g., an image tracked) image stream. For example, such elements may be identified automatically, and the gray level of such elements may be changed such that they become more similar to the general background of the cardiac image. For some applications, such elements are identified and then removed from the stabilized image stream by means of a temporal or spatial filter, utilizing the fact that their motion may differ in time and/or relative location from the motion of the heart itself.

For some applications, elements are removed from the stabilized image stream, and the resulting gap is bridged by means of image processing. For example, bridging may be performed by means of gradually changing the gray level (or color) from its value at one side of the gap to its value at the other side of the gap.

For some applications, such elements automatically become less visible in the stabilized image stream, compared with their visibility in the native image stream. Typically this is because the images are not tracked with respect to such elements. Therefore, the relative position of such elements within the image frame typically changes in successive image-tracked image frames. For some applications, as described hereinabove, the image-tracked image frames are averaged, which typically further reduces the visibility of such elements.

For some applications, such elements are removed from the stabilized image stream by means of applying a mask, the mask having been derived from a road map that is generated automatically, as described hereinabove. For example, based upon the road map, a mask is applied to the image stream such that (a) the visibility of portions of the image stream that lie within the road map, and within a given distance from the road map, is not reduced, but (b) the visibility of other portions of the image stream is reduced.

In another example, based upon the road map, a mask is applied to the image stream such that (a) the visibility of portions of the image stream that lie within the road map have the smallest amount of reduction (if any), and (b) the visibility of other portions of the image stream is reduced, such that portions of the image stream further from the road map tend to be reduced more than portions of the image stream closer to the road map.

For some applications, a set of masks are generated, each of the masks corresponding to a respective phase of the cardiac cycle. When the image stream is displayed, masks are applied to image frames of the image stream in sequence, such that when an image frame showing blood vessels during a given phase of the cardiac cycle is displayed, the corresponding mask is applied to the image frame. Alternatively, a mask is generated corresponding to a given phase of the cardiac cycle. The image stream is gated to the same phase of the cardiac cycle, and the mask is applied to the gated image stream.

Example 1 of a Coronary Procedure

Figure 28:
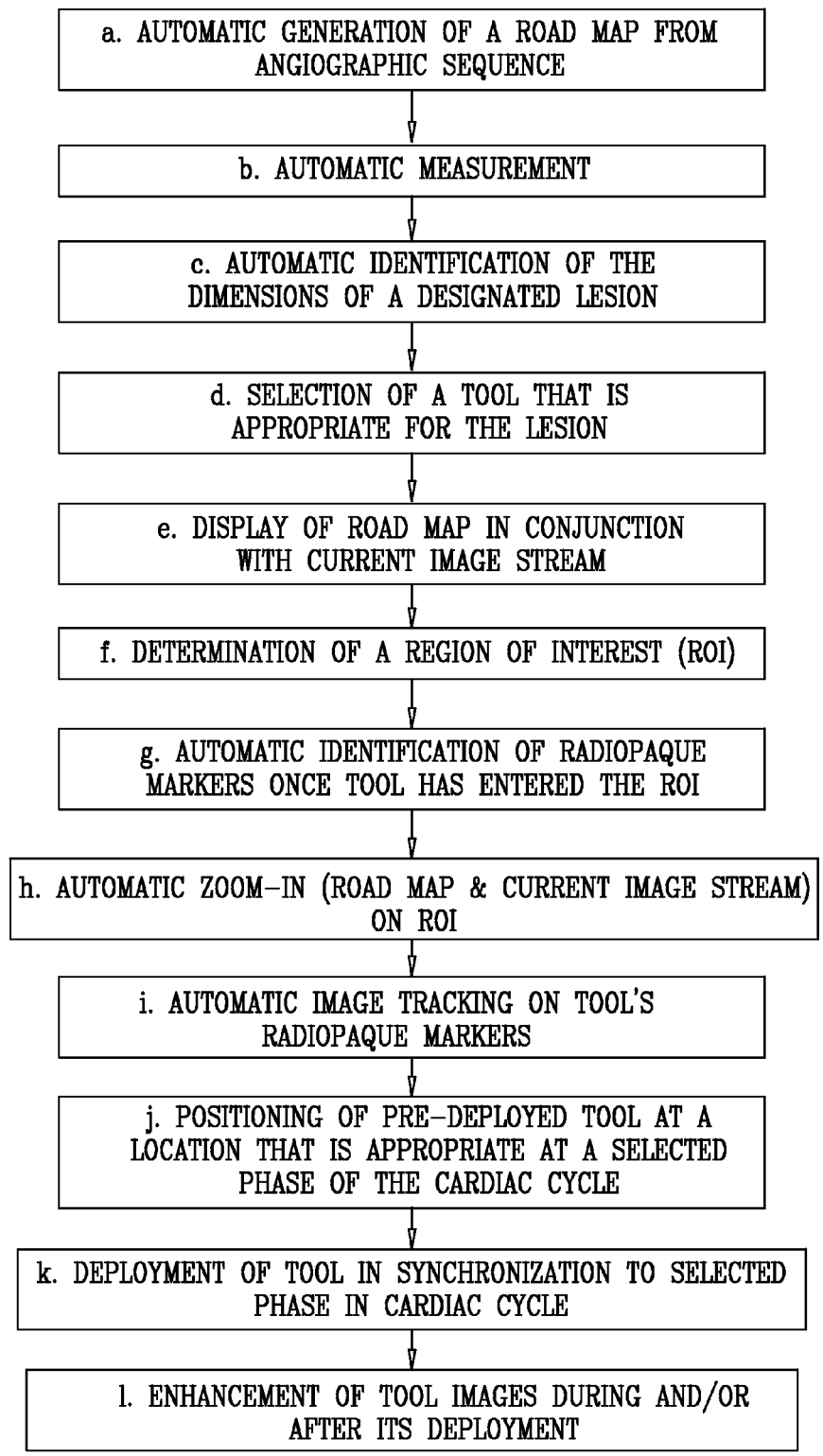
FIG. 28 is a flow chart of a sequence of steps, one or more of which may be performed in a coronary angioplasty procedure, in accordance with some applications of the present invention.

Reference is now made to FIG. 28, which is a flow chart of a sequence of steps, one or more of which may be performed in a coronary angioplasty procedure, in accordance with some applications of the present invention. For some applications, the steps of the procedure are not performed in the order in which they are shown in FIG. 28. Typically, the procedure includes one or more of the following steps:

a. During the diagnosis of the coronary tree by means of angiography, a road map is automatically generated upon each angiographic sequence.
 b. For each road map, measurements are generated automatically or mostly automatically, typically relatively to some known reference dimension.
 c. Lesion and/or artery dimensions, or distance indicators for such dimensions, are identified automatically or mostly automatically, typically relatively to some known reference dimension.
 d. Tools (e.g., balloons and stents of specific dimensions) are selected based upon those measurements.
 e. A road map is presented side-by-side with, and (optionally) is occasionally overlaid upon, the current fluoroscopic image stream. The fluoroscopic image stream may be native or stabilized.
 f. An ROI is determined automatically or indicated by the user.
 g. Once a tool has entered the ROI, its radiopaque segment(s)/markers(s) are automatically identified by the system. For some applications, the user clicks on the tool or in the vicinity of the tool, at which point automatic identification of the segment(s)/marker(s) commences. For some applications, in response to determining the position of the radiopaque segment(s)/markers(s), the shape of the road map is adjusted.
 h. The fluoroscopic image stream and/or the road map is automatically zoomed into the ROI.
 i. Image tracking commences automatically on the radiopaque tool segment(s)/markers(s). A tracked image stream is generated and displayed. Motion of the tool over the course of the heart's motion cycle, relative to the vessel and, specifically, relative to a designated lesion, is observed and (optionally) highlighted by graphical means.
 j. The pre-deployed tool is positioned such that its location is appropriate, relative to the designated lesion, at a selected phase of the cardiac cycle.
 k. Tool deployment is performed such that it is synchronized, during some or all of the deployment process, to the selected phase in the cardiac cycle.
 l. Tool images are enhanced, both during the deployment and upon its completion, to assess the properness of the deployment. For some applications, such enhancement is performed and displayed continuously and on-line in the course of tool positioning, deployment and post-deployment. For some applications, image tracking, and/or image enhancement, before, during, and/or after the deployment of the tool is performed with respect to the lesion.

Example 2 of a Coronary Procedure

Figure 29:
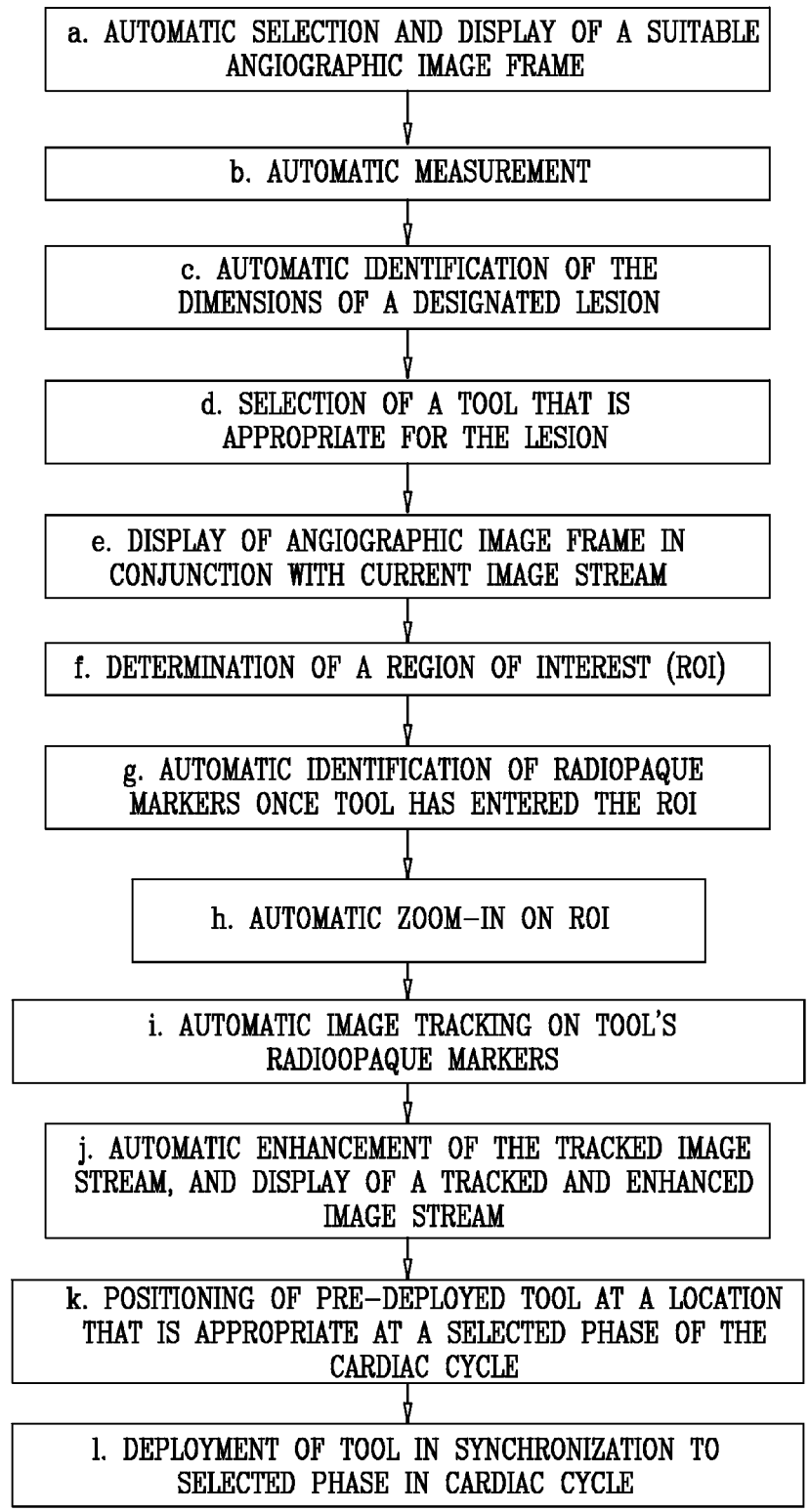
FIG. 29 is a flow chart of a sequence of steps, one or more of which may be performed in a coronary angioplasty procedure, in accordance with some applications of the present invention.

Reference is now made to FIG. 29, which is a flow chart of a sequence of steps, one or more of which may be performed in a coronary angioplasty procedure, in accordance with some applications of the present invention. For some applications, the steps of the procedure are not performed in the order in which they are shown in FIG. 29. Typically, the procedure includes one or more of the following steps:

a. During the diagnosis of the coronary tree by means of angiography, an angiographic image frame suitable for a road map is derived, typically automatically. For some applications, the sequence leading to such derivation is the one described with reference to steps 1 through 5 of FIG. 1. The derived angiographic image frame is displayed, typically without displaying a road map. Steps a and b of the present flow chart may be repeated for multiple viewing angles and/or different sections of the coronary tree.
 b. For each derived angiographic image frame, measurements are generated automatically or mostly automatically, typically relatively to some known reference dimension.
 c. Lesion and/or artery dimensions, or distance indicators for such dimensions, are identified automatically or mostly automatically, typically relatively to some known reference dimension.
 d. Tools (e.g., balloons and stents of specific dimensions) are selected based upon those measurements.
 e. A suitable angiographic image frame is presented side-by-side to the fluoroscopic image stream. The fluoroscopic image stream may be native or stabilized. The frames may be presented side-by-side in real time, near real time, or in reloop mode.
 f. An ROI is determined automatically or indicated by the user in either the angiographic image frame, or, as is typically the case, in the current fluoroscopic image stream.
 g. Once a tool has entered the ROI, its radiopaque segment(s)/markers(s) are automatically identified by the system. For some applications, the user clicks on the tool or in the vicinity of the tool, at which point automatic identification of the segment(s)/marker(s) commences.
 h. The fluoroscopic image stream, and/or the angiographic image frame is automatically zoomed into the ROI, according to some predetermined zoom factor, or according to a zoom factor that is input by the user.

i. Image tracking of the fluoroscopic image stream commences automatically with respect to the radiopaque tool segment(s)/markers(s). A tracked image stream is generated and (optionally) displayed. Motion of the tool over the course of the heart's motion cycle, relative to the vessel and, specifically, relative to a designated lesion, may be observed and (optionally) highlighted by graphical means.

j. An image stream that is both tracked and enhanced is displayed. In accordance with respective applications, enhancement is performed with respect to a vessel highlighted by contrast agent, a balloon being inflated, a deployed stent, or any combination thereof.

k. The pre-deployed tool is positioned such that its location is appropriate, relative to the designated lesion, at a selected phase of the cardiac cycle.

l. Tool deployment is performed such that it is synchronized, during some or all of the deployment process, to the selected phase in the cardiac cycle.

Percutaneous Valve Replacement and/or Repair

Although some applications are described herein with respect to the diagnosis and treatment of the coronary arteries in the context of coronary angiography and/or angioplasty, the scope of the present invention includes applying the apparatus and methods described herein to other medical procedures. For example, the apparatus and methods described herein may be applied to percutaneous valvuloplasty, and/or replacement and/or repair of a valve (also known as percutaneous valve procedure), such as an aortic valve, a mitral valve, a pulmonary valve, or a tricuspid valve. For some applications, the percutaneous approach is transvascular (such as transfemoral). Alternatively, the percutaneous approach is via an incision (such as transapical). For some applications, using the techniques described herein facilitates accurate deployment of the valve, relative to the surrounding anatomy, even within a beating heart, or a moving vessel.

Figure 30:
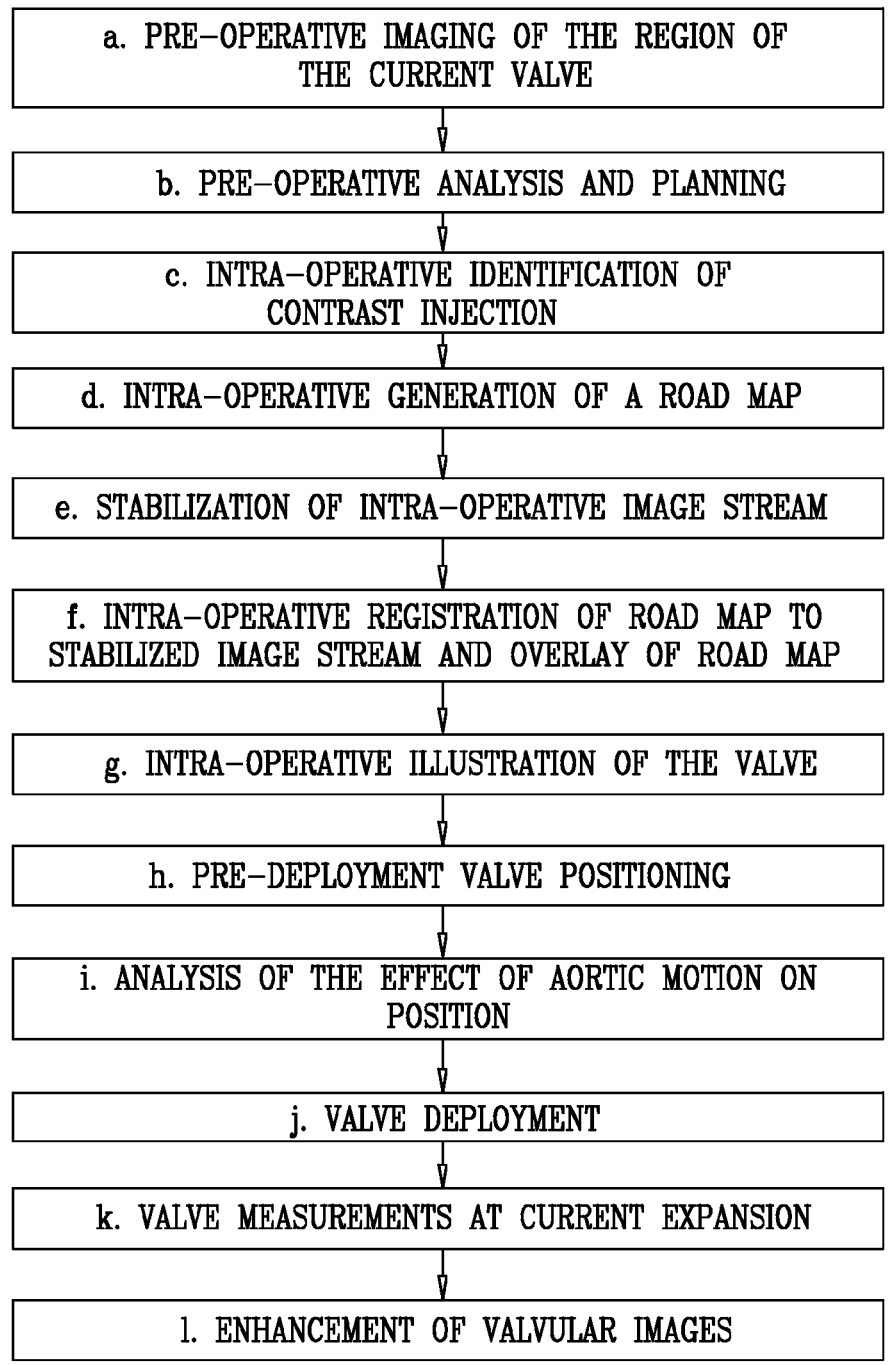
FIG. 30 is a flow chart of a sequence of steps of a percutaneous aortic valve replacement (PAVR) procedure, in accordance with some applications of the current invention.
Figure 31:
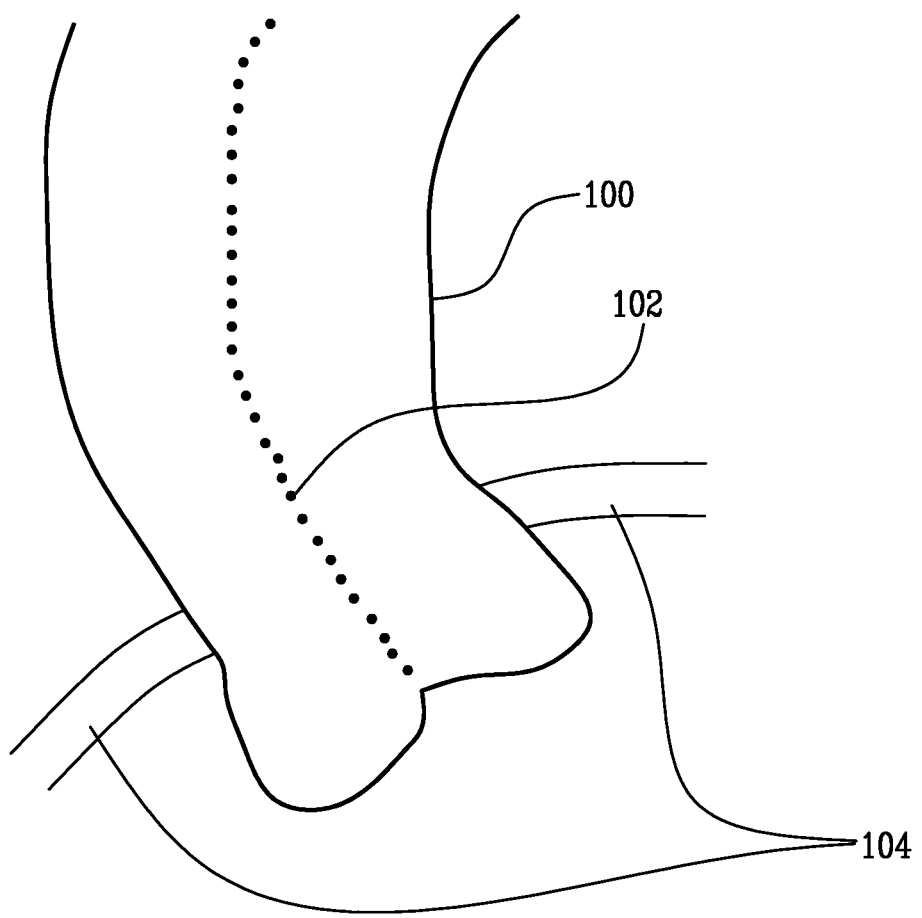
FIG. 31 shows a road map of the ascending aorta, in accordance with some applications of the present invention.

Reference is now made to FIG. 30, which is a flow chart of a sequence of steps, one or more of which may be performed in a percutaneous valve procedure, in accordance with some applications of the present invention. For some applications, the steps of the procedure are not performed in the order in which they are shown in FIG. 30. The procedure is described herein using percutaneous aortic valve replacement (PAVR) as an example. However, the scope of the present invention includes applying the procedure described hereinbelow to any percutaneous valve procedure, applied to any valve, using any suitable equipment, and performed via any percutaneous access route. Typically, the procedure includes one or more of the following steps:

a. The region of the current valve (e.g., the native valve, or a previously-placed replacement valve) is imaged pre-operatively, such as by CT, ultrasound, or using a different imaging modality.

b. The pre-operative images are analyzed to determine the desired location, position and dimensions of the new aortic valve. For some applications, target lines pertaining to the desired location and/or angle of the positioned valve are added. Alternatively or additionally, virtual valves are deployed using some of the techniques described hereinabove. Optionally, such pre-operative images are later registered to, and displayed in conjunction with, the intra-operative image stream. For some applications, intra-operative images generated by rotational angiography or CT-like cross-sectional angiography, typically at the beginning of the procedure, are later registered to, and displayed in conjunction with, the intra-operative image stream.

c. An intra-operative injection of contrast agent under fluoroscopic imaging into the ascending aorta is detected, typically automatically, using the techniques described hereinabove. This step is typically performed on multiple occasions in the course of the procedure, upon a contrast agent being administered to the subject.

d. Reference is now made to FIG. 31, which shows a road map of the ascending aorta 100, in accordance with some applications of the present invention. Typically, the road map is generated automatically, in accordance with the techniques described herein. Typically, one or multiple image frames of the contrast agent are utilized for generating a road map of the ascending aorta (or a portion thereof such as the lower portion adjacent to the location of the native valve), typically automatically, and typically on-line, using techniques described hereinabove. For some applications, the road map includes a center line 102 which may later be useful for leading the valve into position and/or placing the valve at a desired orientation relative to the native anatomy. Alternatively or additionally, the road map includes target lines pertaining to the desired location and/or angle of the valve after it will be positioned. Further alternatively or additionally, the road map includes segments 104 of the coronary arteries, which may later be useful for ensuring that the new valve is positioned so that it does not block any of the coronary arteries. For some applications, the road map also includes calcified portions of the anatomy (such as calcifications in the existing valve, in the aorta, in sections of the coronary arteries connecting to the aorta, or in other portions of the subject's body). Alternatively or additionally, the road map includes a radiopaque portion (such as a ring) of a previously-placed replacement valve which may later be used as a reference for positioning a new replacement valve.

e. Image tracking is applied to the intra-operative image stream, typically automatically. For example, one or more observable features are tracked, such as radiopaque segments or markers of the valve delivery device, of one or more sections of the valve itself which may be radiopaque by design or become radiopaque due to the presence of contrast agent within it, or one or more sections of a previously-placed replacement valve. For some applications, one of the techniques for image tracking and stabilization described hereinabove are applied to the PAVR procedure. Thus, for some applications, a stabilized image stream is displayed in real time or near real time. For some applications, the image stream that is displayed is gated to a selected phase in the cardiac cycle, and (optionally) gap filling among the gated image frames is applied.

f. The road map is registered, typically automatically, and typically on-line, to the fluoroscopic image stream of the corresponding anatomy. In accordance with respective applications, the road map is registered to the fluoroscopic image stream that has or has not been stabilized (for example, via image tracking). Typically, based on the registration of the road map to the fluoroscopic image stream the road map is overlaid on the fluoroscopic image stream. Further typically, fiducials are identified within the road map and within the fluoroscopic image stream, in order to facilitate the registration of the road map to the fluoroscopic image stream. For some applications, registration fiducials include the edges of the ascending aorta, the new valve's delivery mechanism, radiopaque sections of the new valve, calcified portions (which may typically be observed under fluoroscopy) of the original valve, a radiopaque portion (such as a ring) of a previously-placed replacement valve, and/or a radiopaque portion of a pigtail catheter.

Figure 32:
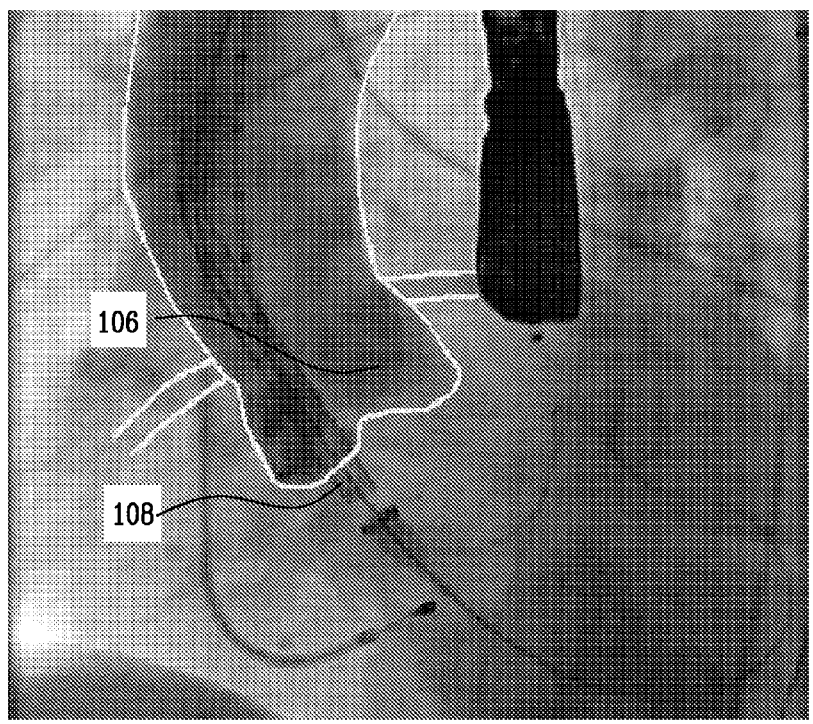
FIG. 32 shows the road map of the ascending aorta overlaid upon a fluoroscopic image stream of the corresponding anatomy, in accordance with some applications of the present invention.

Reference is now made to FIG. 32, which shows a road map of the ascending aorta 106 overlaid upon a fluoroscopic image stream of the corresponding anatomy. For some applications, the observable feature(s) used for the aforementioned image tracking are not the same as the fiducial(s) used for the aforementioned registration of the road map to the image stream. For example, a valve or a valve delivery device 108 may be used for image tracking, while a pigtail catheter, which is generally stable relative to the aorta, may be used for the registration (including dynamic registration) of the road map.

Figure 33A:
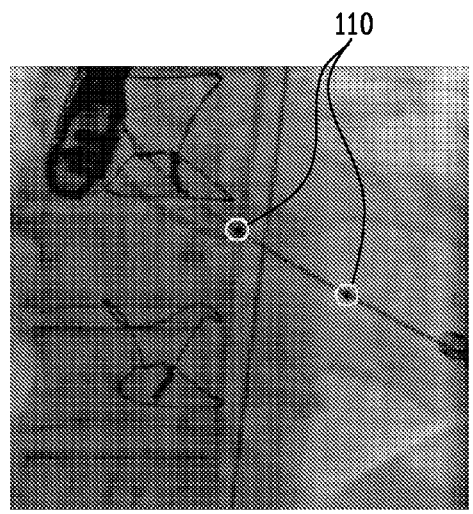
FIGS. 33A and 33B show radiopaque markers of a transapical valve delivery device and of a transfemoral pigtail catheter, which are automatically identified, in accordance with some applications of the present invention.
Figure 33B:
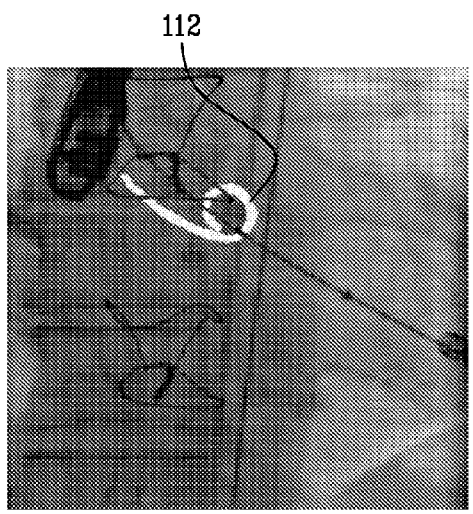

Reference is now made to FIG. 33A, which shows an image in which radiopaque markers 110 of a transapical valve delivery device have been identified for the purpose of image tracking. The markers are typically identified automatically, as described hereinabove. The markers are highlighted in the image. Reference is also made to FIG. 33B, which shows an image in which a transfemoral pigtail catheter 112 has been identified for the purpose of registering the image to a road map. The pigtail catheter is typically identified automatically, using techniques similar to those described hereinabove (e.g., using pattern matching). The catheter is highlighted in the image.

For some applications, the aforementioned valve and the aforementioned pigtail catheter are inserted via similar routes of access (such as transfemoral). Alternatively, the valve and the pigtail catheter are inserted via different routes of access (for example, the valve may be inserted transapically, while the pigtail catheter is inserted transfemorally).

g. For some applications (for example, if the valve itself is not sufficiently radiopaque to be clearly visible in the fluoroscopic image stream), a graphic of a valve is generated, based on a known geometrical location of the valve relative to the radiopaque valve delivery device, or to a feature (e.g., a stent) to which the valve is fixed. Typically, most of the replacement valve is illustrated graphically. However, for some applications, only the distal edge of the valve is graphically illustrated, but the remainder of the valve is imaged.

Figure 34:
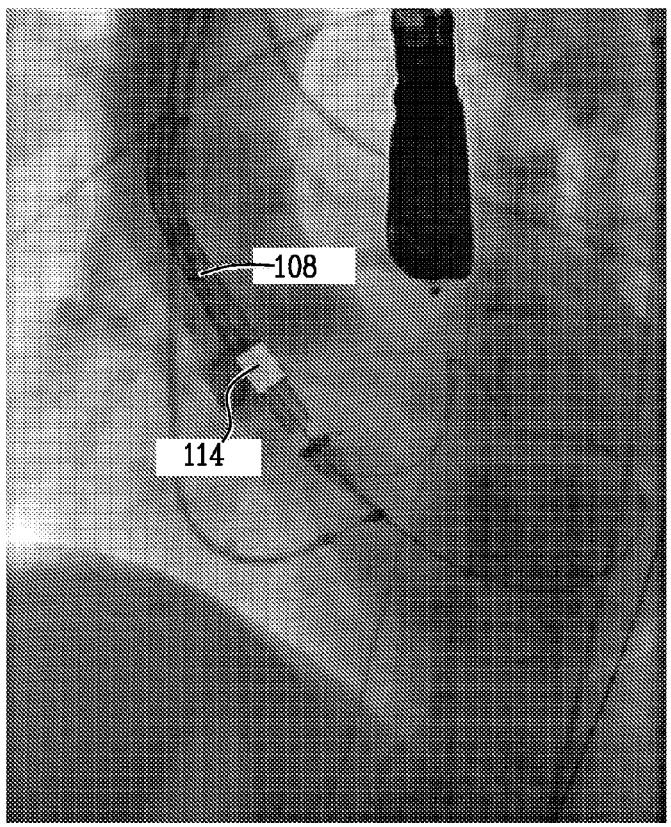
FIG. 34 shows a valve, which is graphically illustrated based on its known location relative to a radiopaque valve delivery device, in accordance with some applications of the present invention.
Figure 35:
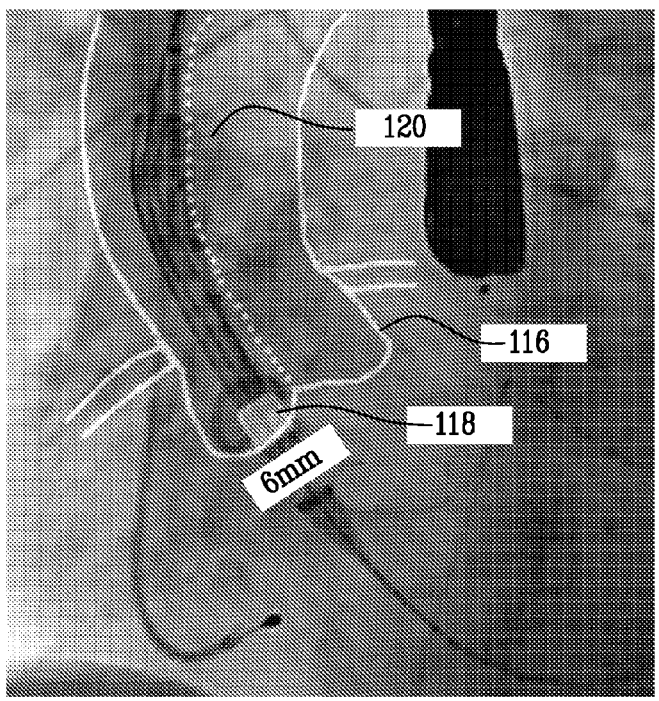
FIG. 35 shows an image of a pre-deployed graphically illustrated valve positioned upon a stabilized image stream on which a road map has been overlaid, in accordance with some applications of the present invention.

Reference is now made to FIG. 34, which shows a valve 114 that has been graphically illustrated. Typically, the valve is graphically illustrated based on its known relative location to radiopaque valve delivery device 108.

h. The valve delivery device is positioned, optionally using the road map, such that the location of the pre-deployed valve (or of the aforementioned illustrated valve) in the typically stabilized image stream is appropriate, relative to an implantation location of the valve. For example, a line marking the distal edge (or any other known section) of the new valve may be guided toward a target line in the road map till the two significantly overlap. Alternatively or additionally, a line marking the longitudinal orientation of the new valve is guided toward a longitudinal target line in the road map till the two significantly overlap. Reference is now made to FIG. 35, which shows a pre-deployed graphically illustrated valve 118 positioned upon a stabilized image stream of the aorta 120 on which a road map 116 has been overlaid.

i. In the prior art, certain replacement valves are typically deployed under rapid pacing in order to momentarily neutralize the aortic blood flow (which is typically very forceful). For some applications, techniques are provided to account for cases of "valve shift," i.e., cases in which once rapid pacing is stopped and the forceful flow of blood along the aorta resumes, the implanted valve shifts distally relative to its original position of deployment. For example, the valve may shift due to a "sail in the wind" effect of the blood flow on the valve. Thus, for some applications, the positions of the pre-deployed valve are determined at different phases in the cardiac cycle, such as systole and diastole, during the subject's normal heart beat, and not during rapid pacing. Determination of the valve's positions is typically facilitated by observing an image stream that has been stabilized by means of image-tracking the pre-deployed valve, according to techniques described hereinabove. For some applications, it is determined that the pre-deployed valve shifts by a distance D mm along the vessel over the course of the cardiac cycle. Therefore, the valve is aimed and deployed at a distance from its designated implantation location in the ascending aorta that is determined based upon the observed shift of the valve of D mm. For example, the valve may be deployed at the distance of D mm from its designated implantation location. For some applications, the non-deployed valve shifts by a smaller distance than the deployed valve, due to blood flow having a greater sail in the wind effect on the deployed valve than the non-deployed valve. Therefore, the valve is deployed at a distance that is greater than D mm from its designated implantation location. Alternatively, the non-deployed valve shifts by a greater distance than the deployed valve, for example, due to greater resistance of the vessel walls on the deployed valve than on the non-deployed valve. Therefore, the valve is deployed at a distance that is less than D mm from its designated implantation location.

Typically, the final position of the deployed valve, after rapid pacing has been stopped and "valve shift" has occurred, is closer to the designated implantation location of the valve compared with deployment of the valve when the shift of the valve is not measured and accounted for, ceteris paribus. Furthermore, accurate determination of the valve shift is typically facilitated by the use of a stabilized image stream for determining the shift of the pre-deployed valve over the course of the subject's cardiac cycle. For example, an image stream may be stabilized by image tracking the image stream with respect to the valve delivery device, the pigtail catheter, and/or a portion of the subject's anatomy that is visible even in the absence of contrast agent (e.g., calcification around the native valve). The valve shift is determined by observing the shift of the valve relative to the vessel in which it is to be deployed, using the image tracked image stream.

Figure 36:
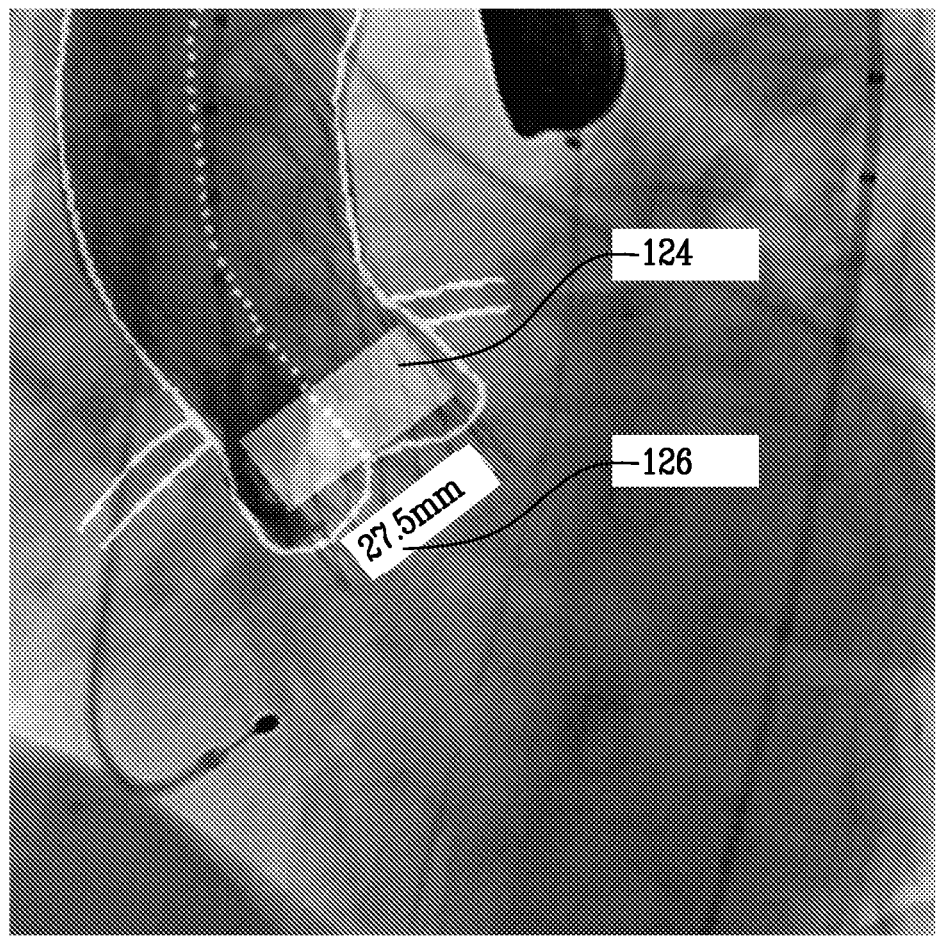
FIG. 36 shows a graphically illustrated expanded valve deployed within the ascending aorta, in accordance with some applications of the present invention.

For some applications, similar techniques to those described with respect to valve shift are applied to account for similar shifting of other tools, such as a stent, or a graft.

j. The valve is deployed. Optionally, deployment is synchronized, in one or more steps, to a selected phase in the cardiac cycle. For some applications, synchronization is performed by a synchronizing device that is connected to the valve delivery device and times its actuation in a gated (e.g., stepwise) manner to a selected phase in the cardiac cycle. For some applications, the synchronization reduces or eliminates the need for rapid pacing during a deployment of a valve that otherwise would have required such pacing. For some applications, deployment of the valve is synchronized to the same phase with respect to which the stabilized intra-operative image stream is gated. For some applications, the synchronization is also applied to a preceding pre-dilatation step, in which the original valve is dilated, such as by means of a balloon, in order to overcome typically-rigid calcified sections and create a space into which to place the new valve. Reference is now made to FIG. 36, which shows a graphically-generated image 124 of a valve being deployed within the ascending aorta. The current outer diameter 126 of the valve is displayed on the image, in accordance with some applications of the present invention.

For some applications, the original (i.e., native) valve is not replaced but rather it is repaired. For example, such repair may include the further coupling, such as via suturing or clipping, of leaves of the native valve to one another. For some applications, pertaining to valve repair (such as mitral valve repair), synchronization is applied to suturing and/or clipping of the cyclically-moving leaflets of the valve. Typically, the synchronization of these procedures facilitates the performance of these procedures because the leaflets shift rapidly back and forth (typically, according to the heart beat). Typically, the synchronization is such that the joining tool is actuated at the phase of the cardiac cycle during which the leaves are closest to one another.

Figure 37A:
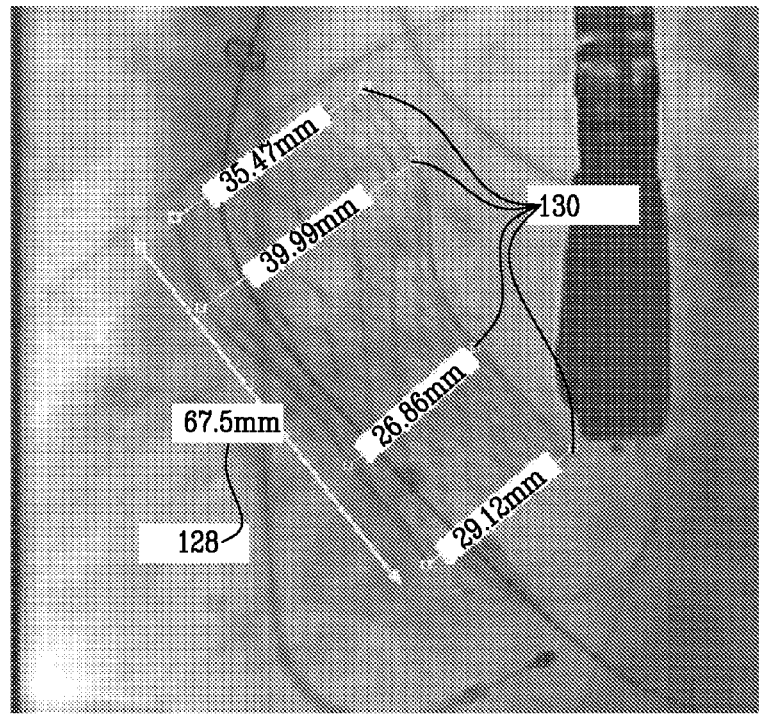
FIGS. 37A and 37B show measurements performed upon a valve deployed in the ascending aorta, in accordance with some applications of the present invention.
Figure 37B:
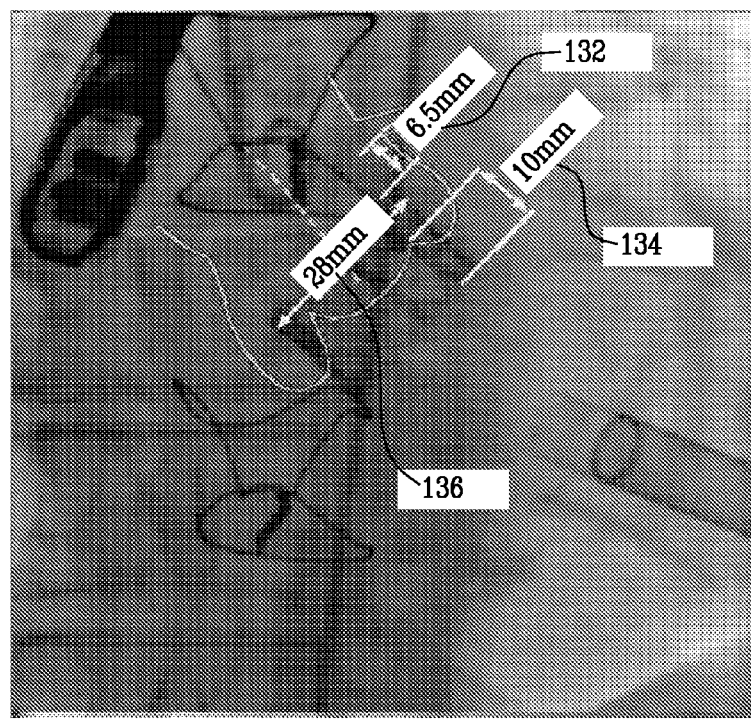

For some applications, synchronization is applied to the deployment of a stent-less valve (i.e., a prosthetic valve typically lacking any rigid supporting structure, such as the Direct Flow valve), which is deployed by being inflated at its designated implantation location. Typically, synchronization is applied to the inflation of sections of the structure of the new valve.

k. At any phase along the process and for any road map, measurements may be generated, automatically or mostly automatically, using techniques described hereinabove. Typically, measurements are performed relative to some known reference dimension such as the diameter of the valve delivery device or the distance between radiopaque elements of the valve itself. For some applications, the measurements include the current size (such as length and/or outer diameter) of the valve while it is being expanded in position, the diameter of the aorta, the space available for deployment of the replacement valve, the distance between the original valve and the aortic ostia of the coronary arteries, the distance between the replacement valve and the aortic ostia of the coronary arteries, the distance between the lower edge of the replacement valve and the aortic annular line, the inner diameter of the replacement valve, the outer diameter of the replacement valve, or any combination thereof. For some applications, measurements are displayed in conjunction with the road map, and/or a fluoroscopic image of the valve. Reference is now made to FIG. 37A which shows, displayed on a fluoroscopic image of a valve deployed in the ascending aorta, measurements of a current length 128, and current outer diameters 130 of respective portions of a valve. Reference is also made to FIG. 37B, which shows, displayed on a fluoroscopic image of a valve deployed in the ascending aorta, measurements of (a) a distance 132 of the valve to the coronary ostium, (b) a distance 134 of the valve to the annular line, and (c) a current outer diameter 136 of the valve.

l. Tool images are enhanced using some of the techniques described hereinabove, both during the deployment, and upon its completion, to assess the properness of the deployment. For some applications, such enhancement is performed and displayed continuously and on-line in the course of valve positioning, deployment and post-deployment.

As used hereinabove, the term "valve delivery device" refers both to insertion elements that are retrieved subsequent to valve deployment, and to fixation elements (such as a stent-like feature) that remain inside the aorta together with the new valve.

Examples of Additional Medical Procedures

Although many of the applications of the present invention are described with reference to the diagnosis and treatment of the coronary arteries in the context of coronary angiography and/or angioplasty, the scope of the present invention includes applying the apparatus and methods described herein to other medical interventions. The scope of the present invention includes applying the techniques described herein to any bodily lumen or cavity on which diagnosis and/or treatment may be performed, including but not limited to the vascular system, the heart's chambers, the bronchial tract, the gastro-intestinal tract, or any combination thereof, and using any form of imaging and any applicable medical tool. For example, the techniques described hereinabove can be applied to any of the following additional procedures, or to any combination thereof. (For some applications, the techniques described hereinabove are applied to the following procedures in combination with techniques described in WO 08/107,905 to Iddan, which is incorporated herein by reference.)

Percutaneous placement, replacement or repair of a valve as disclosed hereinabove. It is noted that the applications described herein pertaining to the suturing of a valve include the suturing of a native or a replacement valve to a lumen of the subject's body, and/or the suturing of leaflets of a valve to each other.

Catheterization of pulmonary arteries, applying the tools and techniques (e.g., guide wire, balloon, stent, occlusion-opening tools) previously described in the context of the coronary arteries. For some applications, such a procedure is performed in conjunction with stabilized imaging as described hereinabove. For example, an image stream of the procedure is stabilized by means of image tracking the observable feature(s) of one or more tools applied in the course of the procedure, in accordance with the techniques described hereinabove. For some applications, the image stream is stabilized with respect to a given phase of the cardiac cycle. Alternatively or additionally, the procedure is performed in synchronization with the cardiac cycle, so as to achieve improved deployment of a balloon or a stent, or better penetration of an occlusion. Typically, the phase during which a tool is deployed is the same as the phase at which the pre-deployed tool has been observed to be properly positioned in the stabilized image stream.

Closure of holes in the septal wall, such as in the treatment of patent foramen ovale (PFO), ventricular septal defect (VSD) and atrial septal defect (ASD), within the cyclically-moving heart. In accordance with techniques described herein, a carrier carrying a closure tool is led to, and positioned at, a desired anatomical location (such as the site of the hole in the septum) while both the carrier and the heart anatomy are viewed in an image stream that is typically stabilized. For some applications, the image stream is stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the closure tool is deployed at the desired anatomical location at a given phase of the cardiac cycle. (Deployment of the tool includes its positioning, assembly, expansion, and/or release from the carrier.) The phase during which the tool is deployed is typically the same as the phase at which the pre-deployed tool has been observed to be properly positioned in the stabilized image stream. For some applications, the closure tool is deployed by expanding the closure tool at the given phase during a single cycle. Alternatively, the closure tool is deployed by expanding the closure tool in a step-wise manner, at the selected phase, during more than one cycle.

Placement of a stent graft within the cyclically-moving aorta to treat abdominal aortic aneurysms. In accordance with techniques described herein, a carrier carrying a stent graft is led to, and positioned at, a desired anatomical location (such as the site of the aneurysm) while both carrier and aortic anatomy are viewed in an image stream that is typically stabilized. For some applications, the image stream is stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the stent graft is deployed at the desired anatomical location at a given phase of the cardiac cycle. (Deployment of the stent graft includes its assembly, expansion and/or release from the carrier.) The phase during which the tool is deployed is typically the same as the phase at which the pre-deployed tool has been observed to be properly positioned in the stabilized image stream. For some applications, the graft is deployed at the desired anatomical location at a given phase of the cardiac cycle (such as when the corresponding section of the target vessel is at its peak dimensions), without observing stabilized images. For some applications, the stent is a self-expansible stent.

Trans-catheter placement of a bypass graft to a cyclically-moving vessel. In accordance with techniques described herein, a catheter carrying a bypass graft (or any other form of a bypass) is led to, and positioned at, a desired anatomical location (such as proximally to the site of a total occlusion) while both carrier and occlusion are viewed in an image stream that is typically stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the bypass graft is deployed at the desired anatomical location at a given phase of the cardiac cycle, the deployment typically including departure from the native vessel proximally to the site of the occlusion and re-entry to the native vessel distally to the site of the occlusion. (Deployment of the graft includes its assembly, expansion and/or release from the carrier.) The phase during which the graft is deployed is typically the same as the phase at which the pre-deployed graft has been observed to be properly positioned in the stabilized image stream. For some applications, the graft is deployed at the desired anatomical location at a given phase of the cardiac cycle (such as when the corresponding section of the target vessel is at its peak dimensions), without observing stabilized images.

Localized energy application to a tissue, such as within the heart (e.g., cardiac ablation performed by means of radio frequency ablation, cryoablation, laser, electrocautery, or ultrasound, to treat cardiac arrhythmia). For some applications, the present invention facilitates the ablation of endocardial tissue in a desired pattern, such as a continuous line or a series of lines, for example, to apply a Maze procedure to the tissue. For some applications, movement of the ablation tool is performed in synchronization with a given phase in the cardiac cycle. Alternatively or additionally, delivery of energy is performed in synchronization with a given phase in the cardiac cycle. For some applications, the endocardial tissue is observed via an image stream that is stabilized with respect to a given phase of the cardiac cycle, and/or movement and/or actuation of energy delivery of the tool is synchronized to the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Percutaneous myocardial revascularization, such as via creating holes in the heart muscle in a desired pattern and by means of an energy delivery or mechanical penetration tool. For some applications, movement of the tool is performed in synchronization with a given phase of the cardiac cycle. For some applications, the tool is actuated (for example, to deliver energy or drill a hole) in synchronization with a given phase of the cardiac cycle. For some applications, the endocardial tissue is observed via an image stream that is stabilized with respect to a given phase of the subject's cardiac cycle, and/or movement and/or activation of the tool is synchronized with the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Delivering any material or substance, such as, for example, gene therapy or stem cells, to specific locations in the heart muscle. For some applications of the present invention, a substance is injected into the heart muscle in a desired pattern, such as a series of points spread across a surface area. For some applications, movement of the tool is performed in synchronization with a given phase of the cardiac cycle. Alternatively or additionally, delivery of the substance is performed in synchronization with the given phase of the cardiac cycle. For some applications, the endocardial tissue is observed via an image stream that is stabilized with respect to a given phase of the cardiac cycle, and/or movement of the tool and/or delivery of the substance is synchronized with the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Repairing tissue in a cyclically-moving portion of a subject's body, such as in a bypass or a valve or a graft, for example, by clipping, suturing, gluing, and/or another technique. For some applications, movement of the repair tool is performed in synchronization with a selected phase in the cardiac cycle. Alternatively or additionally, the repair (e.g., the suturing) is performed in synchronization with a selected phase in the cardiac cycle. For some applications, the endocardial tissue is observed via an image stream that is stabilized with respect to a given phase of the cardiac cycle, and/or movement of the tool and/or the repair (e.g., the suturing) is synchronized to the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Trans Thoracic Needle Aspiration (TTNA), such as when a cyclically-moving lesion within the lungs needs to be biopsied. Typically, the techniques described herein facilitate the prevention of penetration of life-critical organs, during such a procedure. For some applications of the present invention, an aspiration needle is led to, and positioned at, a desired anatomical location in the thorax (such as a lung lesion) while both the tool and thoracic anatomy are viewed in an image stream (such as CT images) that is typically stabilized with respect to a given phase of the respiratory and/or cardiac cycle. Alternatively or additionally, the image stream is stabilized by means of image tracking the observable feature(s) of one or more tools applied in the course of the procedure, in accordance with the techniques described hereinabove. Subsequently, aspiration is performed at the desired anatomical location in synchronization with a given phase of the cardiac and/or respiratory cycle, which is typically the phase, with respect to which the image stream was stabilized.

Trans Bronchial Needle Aspiration (TBNA), such as when a cyclically-moving lesion within the lungs needs to be biopsied. Typically, the techniques described herein facilitate the prevention of penetration of life-critical organs, during such a procedure.

Neural stimulation in the brain, its activation being synchronized with an EEG signal.

Attaching or placing a tool at a desired location, on or within a cyclically-moving organ.

Moving or directing a tool to a desired location, on or within a cyclically-moving organ.

It is noted that although section headers are used in various portions of the present patent application, the techniques described with respect to one of the sections are typically applicable in combination with techniques described in others of the sections. The use of headers is simply intended to help the reader.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with an image of blood vessels of a subject, comprising:
using at least one processor:
in response to a user designating a single point on the image:
automatically identifying a target portion of a blood vessel in a vicinity of the designated point;
performing quantitative vessel analysis on the target portion of the blood vessel;
and generating an output based upon the quantitative vessel analysis,
wherein identifying the target portion comprises designating a longitudinal portion of the blood vessel having a proximal end that is at a first distance from the point in a proximal direction, and having a distal end that is at a second distance from the point in a distal direction.

2. The method according to claim 1, wherein the blood vessel includes a coronary artery, and wherein performing the quantitative vessel analysis with respect to the blood vessel comprises performing quantitative coronary angiography.

3. The method according to claim 1, wherein performing quantitative vessel analysis with respect to the longitudinal portion comprises determining a minimum diameter of the blood vessel within the longitudinal portion.

4. The method according to claim 1, wherein identifying the target portion comprises identifying a portion of the blood vessel that corresponds to a lesion.

5. The method according to claim 4, wherein identifying the portion of the blood vessel that corresponds to the lesion comprises identifying edge lines of the blood vessel.

6. The method according to claim 4, wherein designating the longitudinal portion having the proximal and distal ends comprises identifying proximal and distal longitudinal locations of the blood vessel at which the lesion ends.

7. Apparatus, comprising:
a display configured to display an image of blood vessels of a subject;
an input device; and
at least one processor, configured:
in response to a user designating a single point on the image, using the input device, to automatically identify a target portion of a blood vessel in a vicinity of the designated point;
to perform quantitative vessel analysis on the target portion of the blood vessel; and
to drive the display to display an output in response to the quantitative vessel analysis,
wherein the processor is configured to identify the target portion of the blood vessel by designating a longitudinal portion of the blood vessel having a proximal end that is at a first distance from the point in a proximal direction, and having a distal end that is at a second distance from the point in a distal direction.

8. The apparatus according to claim 7, wherein the blood vessel includes a coronary artery, and wherein the processor is configured to perform quantitative coronary angiography.

9. The apparatus according to claim 7, wherein the processor is configured to determine a minimum diameter of the blood vessel within the longitudinal portion.

10. The apparatus according to claim 7, wherein the processor is configured to identify the target portion of the blood vessel by identifying a portion of the blood vessel that corresponds to a lesion.

11. The apparatus according to claim 10, wherein the processor is configured to identify the portion of the blood vessel that corresponds to the lesion by identifying edge lines of the blood vessel.

12. The apparatus according to claim 10, wherein the processor is configured to designate the longitudinal portion having the proximal and distal ends by identifying proximal and distal longitudinal locations of the blood vessel at which the lesion ends.

13. A method for use with an image of blood vessels of a subject, comprising:
   using at least one processor, in response to a user designating a single point on the image:
      automatically identifying a portion of a blood vessel in a vicinity of the designated point that corresponds to a lesion, by:
         automatically determining a location of edge lines of the blood vessel, and
         automatically determining longitudinal locations along the blood vessel that correspond to ends of the lesion; and
      generating an output in response to the identification of the portion that corresponds to the lesion.

14. The method according to claim 13, further comprising performing quantitative vessel analysis with respect to the portion.

15. Apparatus, comprising:
   a display configured to display an image of blood vessels of a subject;
   an input device; and
   at least one processor, configured:
      in response to a user designating a single point on the image, using the input device, to identify a portion of a blood vessel in a vicinity of the designated point that corresponds to a lesion, by:
         automatically determining a location of edge lines of the blood vessel, and
         automatically determining longitudinal locations along the blood vessel that correspond to ends of the lesion; and
      to drive the display to display an output in response to the identification of the portion that corresponds to the lesion.

16. The apparatus according to claim 15, wherein the processor is further configured to perform quantitative vessel analysis on the identified portion.

17. A method for use with an image of blood vessels of a subject, comprising:
   using at least one processor, in response to a user designating a first longitudinal location of a blood vessel, and subsequently designating a plurality of additional longitudinal locations of the blood vessel,
   automatically determining a parameter of the blood vessel at each of the additional locations, the parameter being selected from the group consisting of:
      a diameter of the blood vessel associated with the additional location,
      a level of occlusion of the blood vessel associated with the additional location, and
      a longitudinal distance along the blood vessel associated with the additional location; and
   generating an output in response to the determined parameter at each of the locations.

18. Apparatus, comprising:
   a display configured to display an image of blood vessels of a subject;
   an input device; and
   at least one processor, configured:
      in response to a user designating a first longitudinal location of a blood vessel, and subsequently designating a plurality of additional longitudinal locations of the blood vessel, to automatically determine a parameter of the blood vessel at each of the additional locations, the parameter being selected from the group consisting of:
         a diameter of the blood vessel associated with the additional location,
         a level of occlusion of the blood vessel associated with the additional location, and
         a longitudinal distance along the blood vessel associated with the additional location; and
      to drive the display to display an output in response to the determined parameter.

* * * * *